(12) United States Patent
Thedieck et al.

(10) Patent No.: US 10,910,084 B2
(45) Date of Patent: Feb. 2, 2021

(54) METHOD FOR MODELLING, OPTIMIZING, PARAMETERIZING, TESTING AND VALIDATING A DYNAMIC NETWORK WITH NETWORK PERTURBATIONS

(75) Inventors: Kathrin Thedieck, Lörrach (DE); Annika Sonntag, Freiburg (DE); Daryl Shanley, Gateshead (GB); Piero Dalle Pezze, Newcastle upon Tyne (GB)

(73) Assignees: Albert-Ludwigs-Universität Freiburg, Freiburg (DE); Northern Institute for Cancer Research, Newcastle upon Tyne (GB)

( * ) Notice: Subject to any disclaimer, the term of this patent is extended or adjusted under 35 U.S.C. 154(b) by 947 days.

(21) Appl. No.: 14/123,252

(22) PCT Filed: Mar. 21, 2012
(Under 37 CFR 1.47)

(86) PCT No.: PCT/EP2012/001236
§ 371 (c)(1),
(2), (4) Date: Feb. 26, 2014

(87) PCT Pub. No.: WO2012/163440
PCT Pub. Date: Dec. 6, 2012

(65) Prior Publication Data
US 2014/0188450 A1    Jul. 3, 2014

(30) Foreign Application Priority Data

Jun. 1, 2011  (EP) .................................. 11004471
Jun. 8, 2011  (EP) .................................. 11004474

(51) Int. Cl.
G16B 5/00    (2019.01)
(52) U.S. Cl.
CPC ..................... G16B 5/00 (2019.02)

(58) Field of Classification Search
None
See application file for complete search history.

(56) References Cited

U.S. PATENT DOCUMENTS

2011/0264420 A1* 10/2011 Sander ................. G06F 19/12
703/2

FOREIGN PATENT DOCUMENTS

FR       2858446      2/2005
WO    WO 2005/111905  11/2005

OTHER PUBLICATIONS

Meric-Bernstam et al. (J. Clin. Oncology (2009) vol. 27:2278-2287).*
Tao et al. in Biochemistry (2010) vol. 49:8488-8498.*
Iadevaia et al. in Cancer Research (2010) vol. 70(17):6704-6714.*
International Search Report dated Nov. 23, 2012 From the International Searching Authority Re. Application No. PCT/EP2012/001236.
Nyman et al. "Mechanistic Explanations for Counter-Intuitive Phosphorylation Dynamics of the Insulin Receptor and Insulin Receptor Substrate-1 in Response to Insulin in Murine Adipocytes", The FEBS Journal, XP055043904, 279(6): 987-999, Feb. 15, 2012.
Ruths et al. "The Signaling Petri Net-Based Simulator: A Non-Parametric Strategy for Characterizing the Dynamics of Cell-Specific Signaling Networks", PLoS Computational Biology, XP055043916, 4(2): e1000005-1-e1000005-15, Feb. 29, 2008.

* cited by examiner

Primary Examiner — Lori A. Clow

(57) ABSTRACT

The present invention relates to a method for predicting the response of a structure, or a group of structures and/or a network profile, to a perturbation, in particular a perturbation caused by an agent or a combination of agents through modeling, optimizing, parameterizing, testing and/or validating of a dynamic network or of network perturbations.

6 Claims, 38 Drawing Sheets

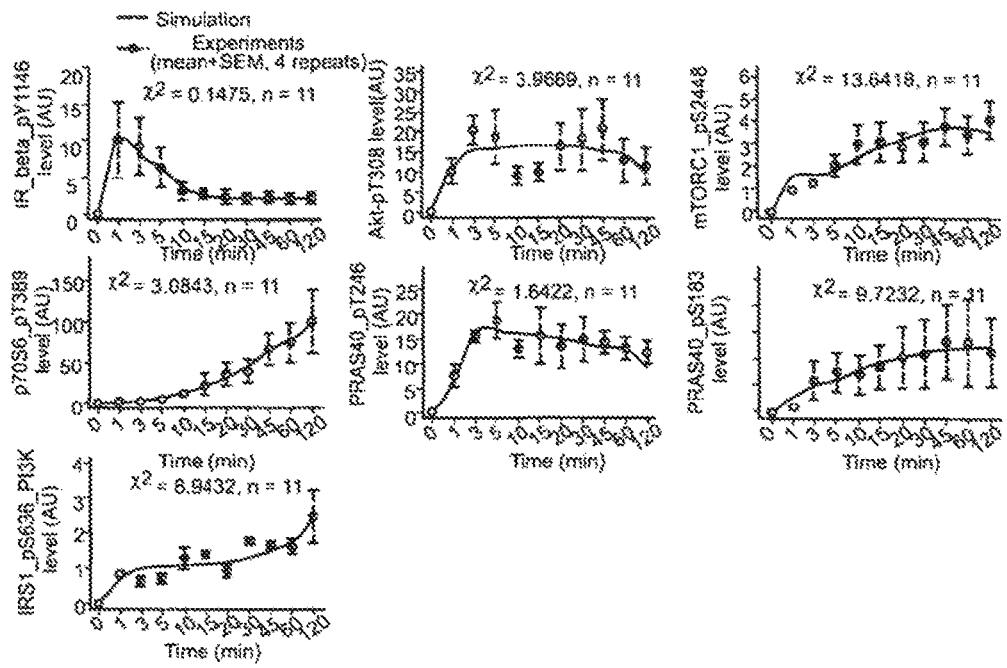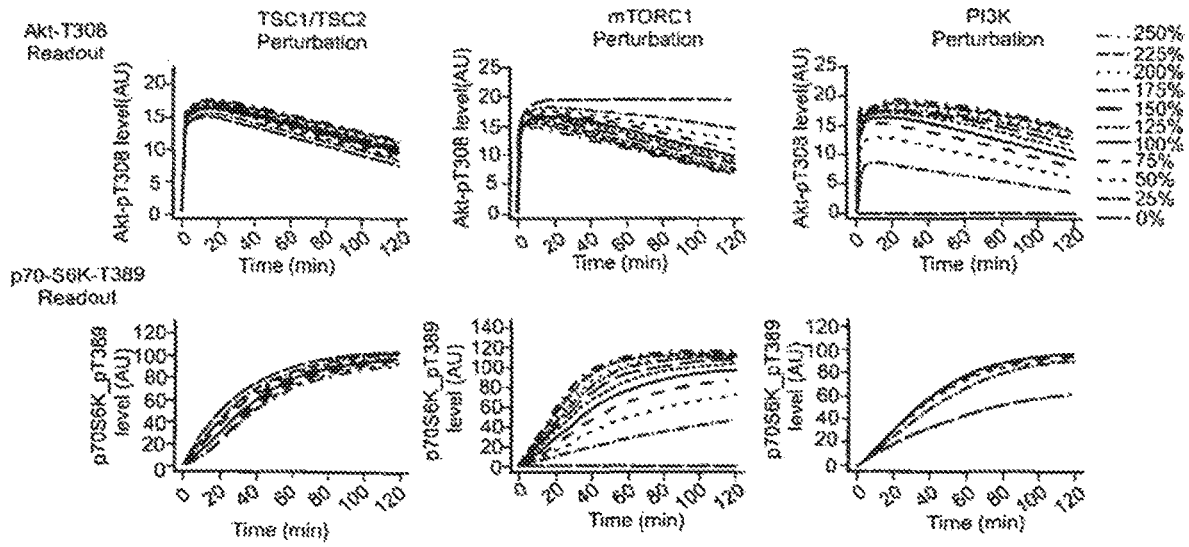
Fig. 26

A

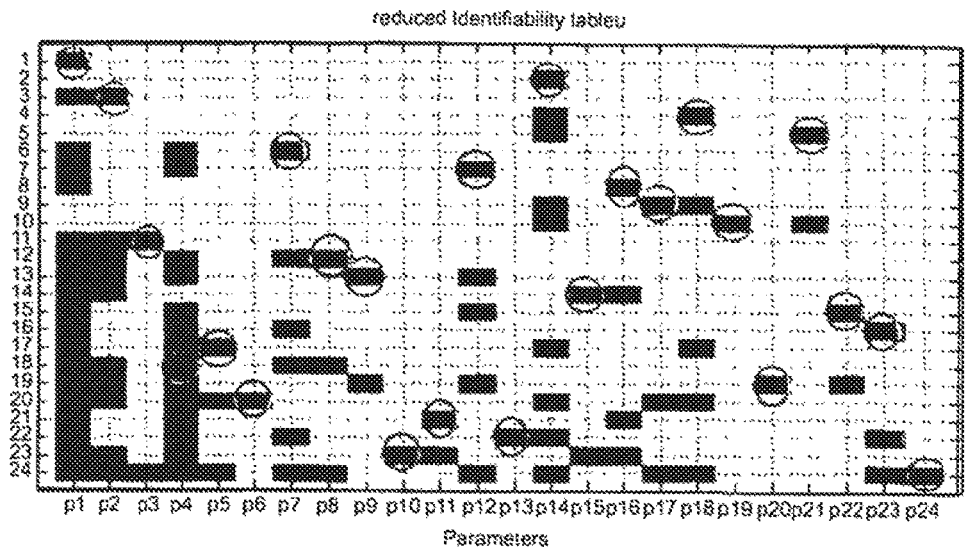

B

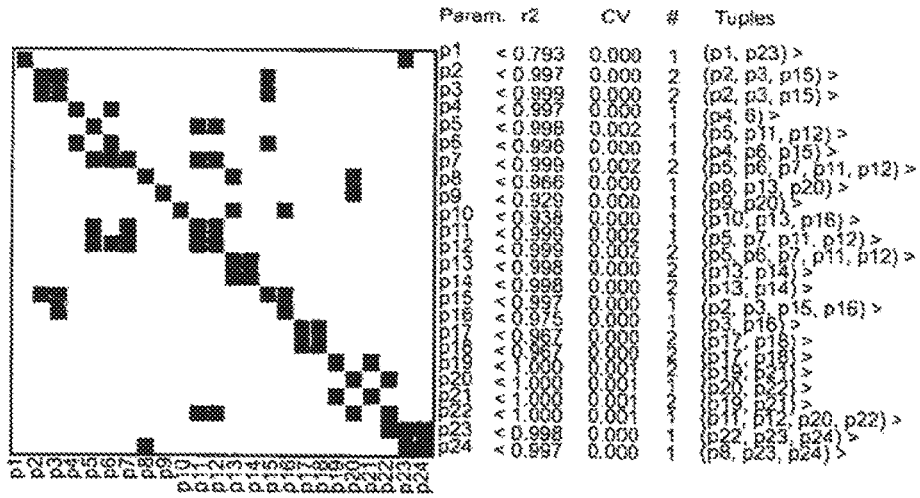

Parameters Legend:

p1 = IR_beta_phosphorylation_by_Insulin
p2 = IR_beta_pY1146_dephosphorylation
p3 = IR_beta_ready
p4 = IRS1_phosphorylation_by_IR_beta_pY1146
p5 = IRS1_p_phosphorylation_by_p70S6K_pT389
p6 = IRS1_pS636_dephosphorylation
p7 = AMPK_T172_phosphorylation
p8 = AMPK_pT172_dephosphorylation
p9 = Akt_pT308_dephosphorylation
p10 = Akt_pS473_dephosphorylation
p11 = Akt_S473_phosphorylation_by_mTORC2_pS2481_n_IRS1_p
p12 = Akt_T308_phosphorylation_by_IRS1_p
p13 = mTORC1_pS2448_dephosphorylation_by_TSC1_TSC2_pS1387
p14 = mTORC1_S2448_activation_by_Amino_Acids
p15 = mTORC2_pS2481_dephosphorylation
p16 = mTORC2_S2481_phosphorylation_by_PI3K_variant_p
p17 = p70S6K_pT389_dephosphorylation
p18 = p70S6K_T389_phosphorylation_by_mTORC1_pS2448
p19 = PRAS40_pS183_dephosphorylation
p20 = PRAS40_pT246_dephosphorylation
p21 = PRAS40_S183_phosphorylation_by_mTORC1_pS2448
p22 = PRAS40_T246_phosphorylation_by_Akt_pT308
p23 = TSC1_TSC2_S1387_phosphorylation_by_AMPK_pT172
p24 = TSC1_TSC2_T1462_phosphorylation_by_Akt_pT308

Fig. 30

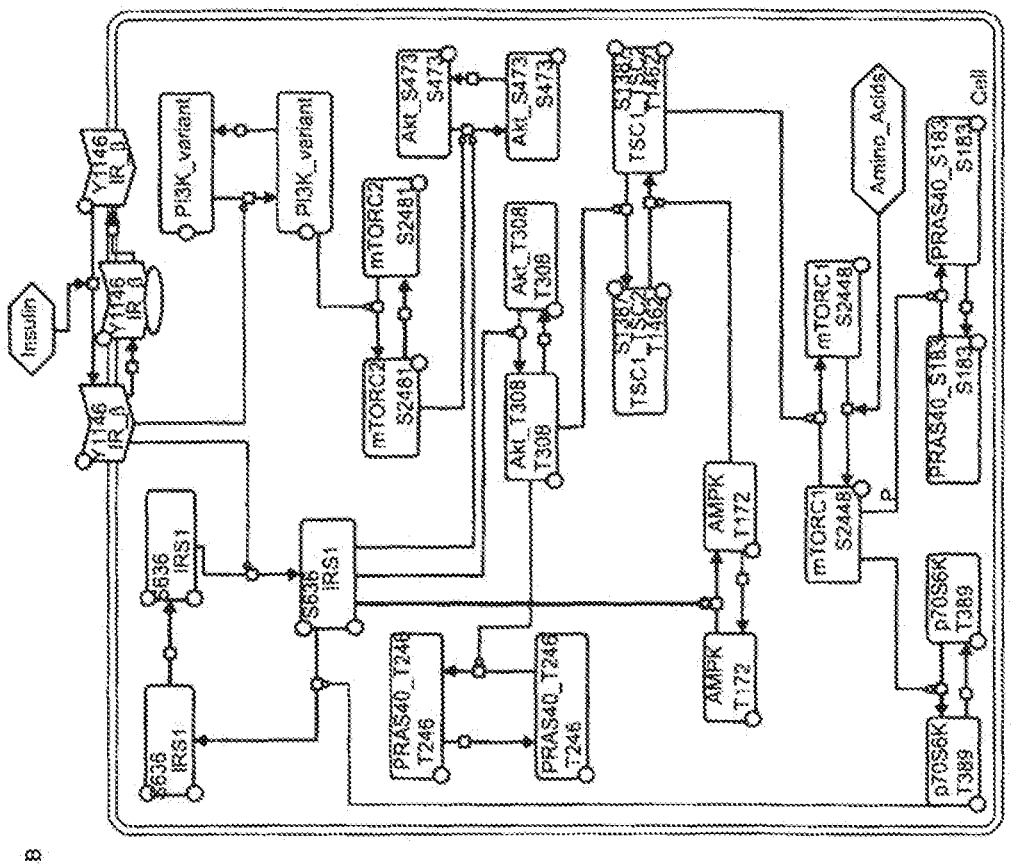
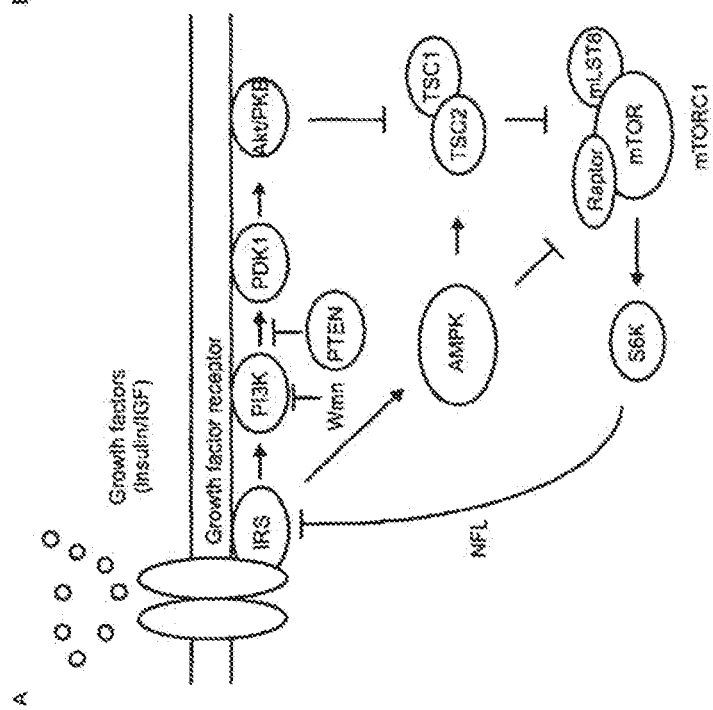
Fig. 33

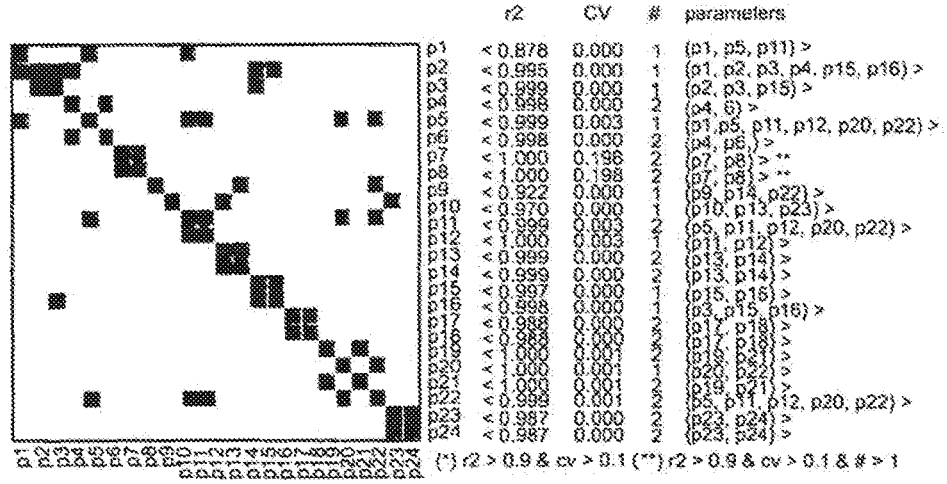
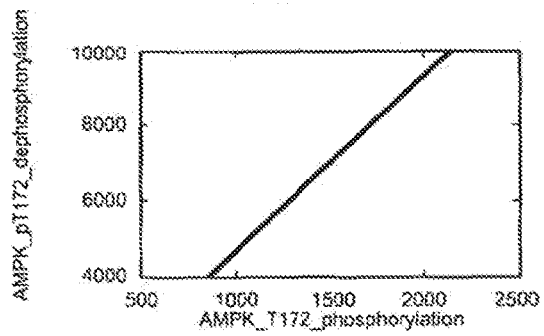
Fig. 34

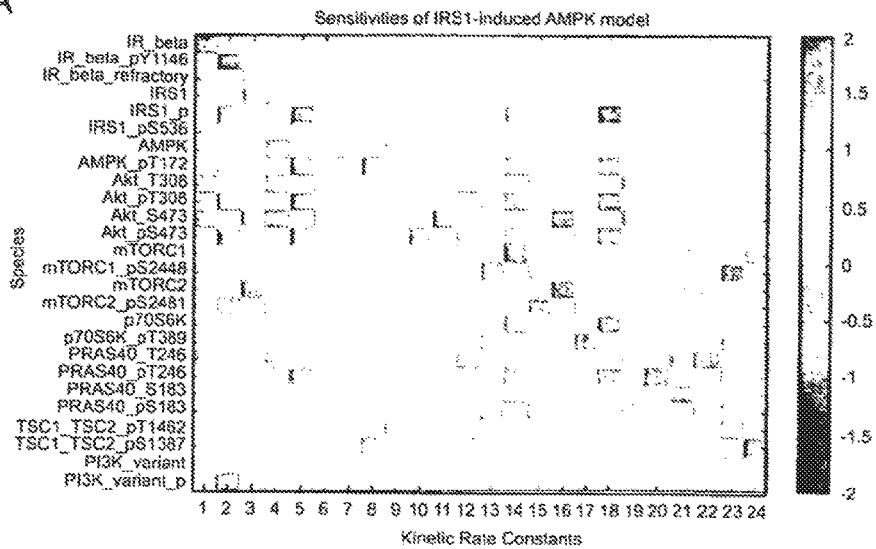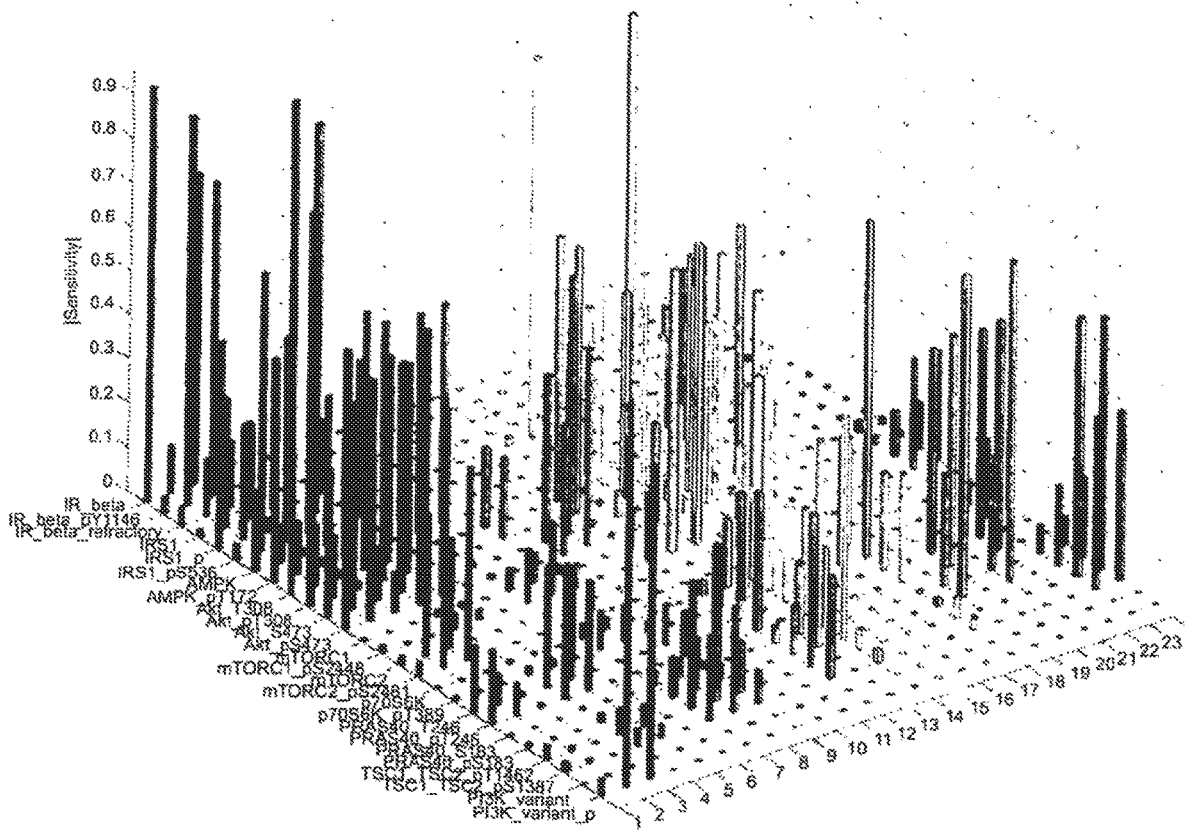
Fig. 35

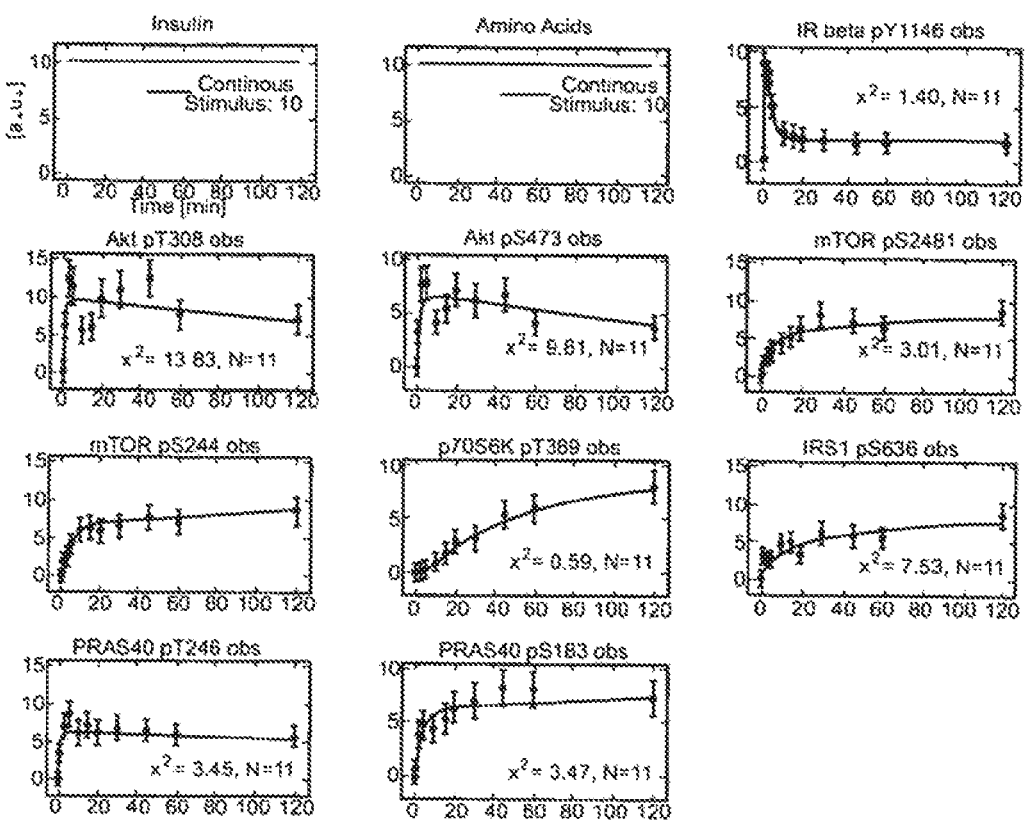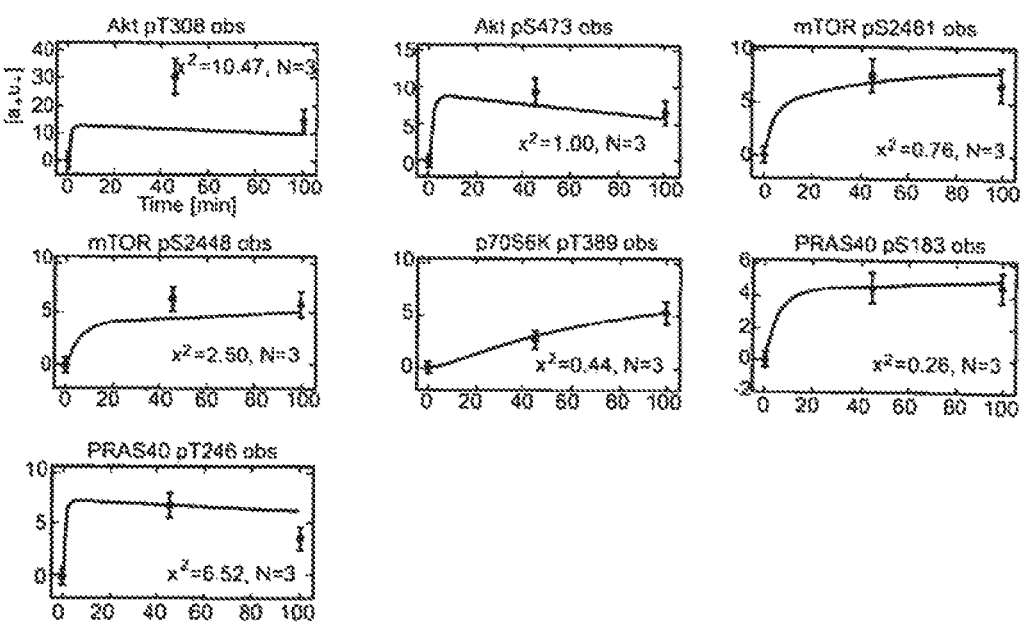
Fig. 36

METHOD FOR MODELLING, OPTIMIZING, PARAMETERIZING, TESTING AND VALIDATING A DYNAMIC NETWORK WITH NETWORK PERTURBATIONS

RELATED APPLICATIONS

This application is a National Phase of PCT Patent Application No. PCT/EP2012/001236 having International filing date of Mar. 21, 2012, which claims the benefit of priority of European Patent Application Nos. 11004471.6 filed on Jun. 1, 2011 and 11004474.0 filed on Jun. 8, 2011. The contents of the above applications are all incorporated by reference as if fully set forth herein in their entirety.

The invention relates to a method for predicting the response of a structure, of a group of structures and/or of a network profile, as a result of a perturbation, in particular by an agent or a combination of agents and to a use of said method.

Methods of this type are principally known, in particular methods directly related to signalling. For example models for static networks are known that require careful inclusion of known molecular interactions reported in the literature or in databases.

FIELD AND BACKGROUND OF THE INVENTION

WO 2005/111905 A2 describes a prediction of the dynamic behaviour of a biological system. Therein, a method is disclosed for the prediction of a dynamic behaviour of a biological system, whereby a computational model of said biological system is generated within the method, and the model is afterwards populated based on publicly available information using import/export functions. Thereafter, the model is populated based on experimental data with respect to initial conditions and kinetic parameters of the model and a differential equation system is set up describing the time dependency of the concentrations of model objects. Finally, the differential equation system is solved.

It is disclosed in WO 2005/111905 A2 how to set up a general network, but not how to set up specific networks. To build up specific networks, first of all the specific components of such a specific network have to be selected. As the next step, the selected components and the interaction between the specific components have to be identified and integrated into the method. The model has to be parameterized with specific quantitative dynamic data. It is not disclosed how to predict the network reaction, and in particular the clinical outcome as the response to a specific agent or a combination of agents under the specific set of parameters, and in particular to mutational profiles of individual patients.

US 2006/0235670 A1 discloses a method and system for selecting therapeutic targets using molecular interaction dynamics networks. The method and the system relate to the use of a modelling approach for predicting putative drug targets based on large omics data sets. In particular, it is not disclosed to predict, based on specific time course data, network behaviour and in particular clinical outcome and beneficial agents and agent combinations for agents targeting known targets, singly or in combination.

Many models rely on published data from external sources. But to reach the most suitable readouts and to reach ensuring coherence of the data sets the data for the known models should be generated specifically for the model.

Some of the known experimental-computational approaches address very general networks, and in contrast to said general approaches most combined experimental-computational approaches address very specific questions, so that the generated data sets are often of narrow scope, covering only one single or two time points or comparatively limited parts of the network.

In particular, none of the existing models, in particular models of Insulin—mammalian Target Of Rapamycin kinase (mTOR) signalling integrates mammalian Target Of Rapamycin Complex 2 (mTORC2) regulation.

Therefore, the known methods need to be set-up or calibrated for every specific question which is time-consuming and expensive.

SUMMARY OF THE INVENTION

Accordingly, it was an object of the instant invention to suggest a method that extends usability for different specific questions and that improves prediction of the response of a structure in reaction to a perturbation, in particular to an agent or a combination of agents.

This object is achieved with a method in accordance with claim 1. Preferred embodiments are set forth in the dependent claims.

The instant invention provides a method for predicting the response of a structure, of a group of structures and/or of a network profile, as a result to a perturbation, in particular by an agent or a combination of agents through modelling, optimizing, paramaterizing, testing and/or validating a dynamic network or network perturbations, comprising the steps of:

a. Selecting at least one appropriate structure model or specific profile model of the at least one structure, of the group of structures and/or of the network profile;

b. Identifying at least one perturbation in particular by at least one agent and/or at least one combination of agents and, if necessary, identifying the concentration agent or combination of agents;

c. Parameterizing the at least one structure model or specific profile model of the at least one structure profile or the at least one combination of structure models or specific profile models, whereby the structure models or specific profile models use at least a dynamic network model, in particular of insulin-mTOR kinase model for signalling or regulation;

d. Reducing the number of parameters, in particular the parameters for parameterizing the at least one structure model or specific profile model and/or the at least one combination of structure models or specific profile models of the structure, in particular of a dynamic network model to generate a reduced structure, in particular a reduced dynamic network model;

e. Calculating the response of each structure, of the group of structures and/or of the network profile caused by the perturbation, in particular by an agent and/or combination of agents;

f. Defining at least one subcollective of structure profiles, of the group of structures and/or of the network profile caused by the response with the best outcome;

g. Displaying at least the profile subcollective, the corresponding perturbation, in particular the corresponding agent and/or the combination of agents.

The step of parameterization can also comprise everything within the pathway, for example proteins, involved mutations and/or the like.

The prediction of the response of a structure, of a group of structures and/or of a network profile, as a result to a perturbation depends on the modelling described above. Through said modelling, optimizing, paramaterizing, testing and/or validating a dynamic network or network perturbations the desired response could be predicted.

The prediction of the response of a structure is a particular case of the modelling of a dynamic network as a result to a perturbation of a network, in general. Each structure can thereby be subdivided into groups of structures. Different parameter settings correspond to individual network profiles.

Additionally, the sequence of the steps of the method can vary from the above described sequence.

Generally the structure, the group of structures and/or the network profile can be found in any suitable way. However, it has proven to be advantageous that the method comprises a step of identifying at least one structure, one group of structures and/or a network profile, in particular by uploading from a database and/or by experimental determination.

The inventive method displays the effect of perturbations, in particular of an agent or a combination of agents, and allows a prediction of the best selection of perturbations, in particular agents or combinations of agents to reach the best result on structures or groups of structures.

Furthermore, it can be advantageous, if the reduction of the parameter number, in particular for parameterizing the at least one structure profile and/or the at least one combination of structure profiles is iterative, whereby in each step the value of all undetermined parameters is optimized multiple times.

The reduction of parameters is part of the parameterization process. Parameter reduction is directly connected with the parameterization of the at least one structure model or specific profile model of the at least one structure or profile and/or the at least one combination of structure and profiles; which is due to the fact that a parameterizition must go along with a reduction of parameters since otherwise there would be no possibility to identify one single best solution for the equations to be solved.

Additionally, it is also possible that at least one parameter is reducible by manual setting and/or database related setting.

Generally, the iteration within the step of parameter reduction can be set manually or automatically. For example, the iteration can be infinite or limited. In particular, if the iteration is limited, the total number of iterations can be set manually or automatically.

It is preferred that the parameters that cluster within the set of best solution are assigned values and/or that the reduction is repeated with the remaining undetermined parameters until all parameters are assigned a value.

The best solution can be defined in several manners. According to one embodiment, it can prove to be advantageous to define the best solution by giving minimal difference between the dynamic network and given data. Therefore the number of iterations is related to a fault tolerance.

For improving the step of reducing, it has been proven to be advantageous in certain cases that boundaries of reducing number of parameters and/or of a level of, in particular molecular, detail can be set manually and/or automatically.

The boundaries of reducing the number of parameters can only be defined when setting up the model. To extend usability for different specific questions the setting of the boundaries is defined by the number of parameters that allows finding a single best solution.

Moreover, in another embodiment of the invention the parameterization and/or the reduction comprises an initial estimation for at least one parameter, in particular by random generation within the boundaries and in particular for a certain number of initial receptor molecules amount and the related rate constants, in particular in the preferred embodiment at least three receptor initial molecules amounts and three kinetic rates constants in case of the mTOR (mammalian Target Of Rapamycin) model.

The parameter estimation is part of the parameterization process. Parameter estimation is an essential step to derive model parameter from quantitive dynamic time course data.

The parameters of the reduced dynamic model can be selected and/or chosen at will. However, it has proven to be advantageous if the reduced dynamic model comprises parameters of interactions with dynamic behavior such as feedback mechanisms and/or comprises parameters of molecules and interactions that can be measured.

This relates to the decision on which interaction and parameters are to be maintained in a reduced network model structure. This decision is taken based, on one hand, on the dynamic behavior of a specific network component, and on the other hand, on the possibility to measure the behavior of the components. Therefore, this is an integral part of the network reduction process.

Moreover, in a further embodiment of the invention the reduced dynamic model comprises at least three receptor initial molecules amounts and three kinetic rates constants.

The parameterization may generally comprise any data. However, it has proven to be advantageous if parameterization comprises dynamic quantitative time course data, in particular, using a reuse-orientated calibration process to introduce several different network structures without recalibration.

The reuse-oriented calibration process is an iterative modification of the model calibration. Therefore, this a modification of model calibration described above.

The perturbation, in particular the agent or the group of agents, can target anything that inhibits or activates a response of the structure or the group of structures. According to a preferred embodiment, the perturbation, the agent or the combination of agents targets mTOR, in particular in one or several mTOR complexes, in particular mTORC1 (mTOR complex 1) and/and/or mTORC2 (mTOR complex 2), entirely or partly, directly or indirectly; hence, the agent or the combination of agents can also target AMP-dependent kinase (AMPK), Phosphatidylinositol 3-kinases (PI3Ks), or other components of the network.

This is a preferred application of the method of the invention.

According to a preferred embodiment mTOR complexes, in particular their activity, in particular the activity of mTORC1 and/or mTORC2 are calculated by the dynamic network model, in particular the reduced dynamic network model, in particular based on dynamic, in particular quantitive time course model output.

The time course model output may be validated in any way. However, it has proven to be advantageous if the dynamic time course model output is validated experimentally.

Before a model can be used for doing predictions it needs to be validated. Experimental validation is a crucial prerequisite for predicting a reliable network response, in particular clinical outcome. Therefore, the model output is preferably validated.

To increase the quality of the output it has proven to be advantageous if parameterization comprises a structure component modification, in particular molecule modification, in particular protein or lipid modification, in particular with the steps of:
a. calibration of the dynamic network model by assuming a signal input, in particular a receptor, in particular an insulin receptor network dependent regulation;
b. calibration of the network model by assuming the network model independent of mTORC2 and of PDK2 (phosphoinositide-dependent protein kinase 2), in particular by assuming that dynamics are regulated by autoactivation;
c. calibration of the network model by assuming the dynamic network model dependent on mTORC2;
d. calibration of the network model by assuming the network model dependent on PDK2.

The dynamics we follow are component modifications. Therefore the method does relay on the incorporation of these modifications. This is a specification of the parameters of the method with respect to one preferred embodiment of the invention.

In a further embodiment of the inventive method the steps of calibration of the dynamic network model comprise at least one hypothesis for mTORC2 activation that substitutes the mTORC2 dynamics, in particular by:
a. recalibrating the network model by assuming the model as PI3K (phosphatidylinositol 3-kinase)-independent,
b. recalibrating the network model by assuming the model as PI3K-dependent,
c. recalibrating the network model by assuming the model TSC1/TSC2 (tuberous sclerosis) complex protein independent or
d. recalibrating the network model by assuming the model TSC1/TSC2 complex dependent,
e. recalibrating the network by assuming the model PI3K-dependent and TSC1/TSC2-independent.

This is a further specification of one of the preferred embodiments of the method according to the invention.

The parameterization can comprise a step of calibration or can be realized without calibration. It has proven to be advantageous if the parameterization comprises a calibration having the calibration steps:
a. selecting parameters to calibrate;
b. initial estimation for at least one parameter to be optimized, in particular from initial configuration;
c. selecting the best solution;
d. fixing of common parameters;
e. selecting the next unfixed parameters and return to step b or end calibration.

Thereby, the parameterization process is specified.

The response of a structure to a treatment can comprise any reaction of the structure. In a preferred embodiment the response to a treatment comprises the response of tumor cells, in particular kinase activity, in particular mTOR activity, in particular cellular growth.

Additionally, it has proven to be advantageous if a set of gradual in silico and experimental perturbations is established.

Furthermore, in one embodiment of the method the parameterization of each common mutational profile of the at least one cell and/or of the group of cells is based on quantitative measurements.

Furthermore, in one preferred embodiment of the invention the dynamic network comprises a dynamic mTOR network or network model of insulin-mTOR kinase signalling or regulation.

According to another preferred embodiment the structure comprises a, in particular biological, cell, e.g. a tumor cell. In still another preferred embodiment of the invention the agent or combination of agents comprises a kinase inhibitor/activator. It is to be understood that all these preferred embodiments may be combined in any manner with each other.

Another embodiment of the instant invention relates to the use of the method of the instant invention for predicting the effect of the response of a structure in reaction to a perturbation, in particular in response to an agent or a combination of agents, e.g. a kinase inhibitor/activator, and/or for predicting of effects of specific profiles, in particular mutational or metabolic or inhibitor/activator profiles on system behaviour, in particular cellular growth or clinical outcome inhibiting/activating agents, in particular in combination or different concentrations, on clinical outcome in response to, in particular inhibiting and/or activating, agents or combinations of agents having at least one of the previous features.

This is one of the preferred applications of the methods according to the invention.

Furthermore, according to a preferred embodiment such use comprises:
a. subgrouping of patient cohorts according to mutational profiles;
b. selecting of patient cohorts comprising mutational profiles or tumor types with good clinical prognosis in response to perturbations, agents or combinations of agents, in particular combinations of inhibitor(s), and;
c. reduce patient cohorts for proof of efficacy in clinical studies.

The method and the use of the method are advantageous in many ways.

The method relates in particular to the application of a specific kinase model for predicting the effect of combinatorial drug application on the system dynamics, in particular on clinical outcome, in particular in different mutational backgrounds. In addition, the method is directed to existing or novel agents, in particular kinase inhibitors, against in particular known or novel drug targets, and to respond to the question, which combinations are most beneficial in terms of clinical outcome under specific network parameters, in particular in specific mutational backgrounds in particular of individual patients.

In addition, the method can be used for several different network structures without recalibration. Therefore, the range of use of the method is extended compared to existing systems.

Furthermore, the method allows identification of patient populations with mutational patterns presenting a high probability of positive response to perturbations, in particular to pharmaceutically active products or combinations thereof.

Additionally, identification of perturbations, in particular of agents or agent combinations, especially preferred of kinase inhibitor/activator combinations and concentrations with the most beneficial clinical effect in patient sub cohorts with different mutational or metabolic profiles, is possible.

This defies further the preferred achievement to be made by the application of the method according to the invention.

A further benefit is the reduction of patient cohorts, which improves efficacy and statistical strength in clinical studies.

Finally, an improvement of clinical outcomes by appropriate patient selection is enabled.

In the following, several aspects of the invention are described in more detail.

At first, it is referred to an insulin-mTOR network model, integrating both mTORC1 and mTORC2.

The kinase target of rapamycin (TOR) is conserved in all eukaryotes from yeast to humans and is a central regulator of cellular growth, aging, and metabolism. As a central metabolic regulator, TOR is involved in a multitude of human diseases, including cancer and neurodegeneration.

Rapamycin is a well known immunosuppressant in the state of the art, and rapalogues and other TOR inhibitors are applied in cancer therapy. Because of its clinical importance, it is important to understand the exact dynamics and interconnections within the TOR network.

TOR occurs in general in two functionally and structurally distinct multi-protein complexes termed TOR complex 1 (TORC1) and TOR complex 2 (TORC2). The mammalian TOR complex 1 (mTORC1) contains the specific scaffold protein Raptor and the inhibitory binding partner PRAS40; whereas mammalian TOR. complex 2 (mTORC2) contains the proteins Rictor, mSin1, PRR5 and PRR5L. mTORC1 controls cellular growth, translation, transcription, and autophagy, mTORC2 controls spatial growth by regulating the actin cytoskeleton. mTORC1 is specifically inhibited by the small macrolide Rapamycin, whereas mTORC2 is Rapamycin insensitive. ATP analogue TOR kinase inhibitors (TORKinibs) that target both mTOR complexes have also been described in the state of the art. Although the upstream and downstream regulatory mechanisms controlling mTORC1 are well characterized, those regulating mTORC2 are less understood.

mTORC1 is regulated in general by nutrients (amino acids), growth factors (insulin), and energy. Amino acids activate the Ragulator-Rag complex to translocate mTORC1 to lysosomes, where mTORC1 can be activated by the small guanosine trisphosphatase (GTPase) Rheb. Insulin signaling induces a kinase cascade through e.g the insulin receptor (IR), insulin receptor substrate (IRS), class I phosphoinositide 3-kinases (PI3K), phosphoinositide-dependent protein kinase 1 (PDK1), and the AGC kinase Akt (also known as PKB). Akt inhibits for example the tuberous sclerosis complex 1/2 (TSC1/TSC2) dimer, which is the inhibitory GTPase-activating protein (GAP) for Rheb. Through this cascade, Akt stimulates mTORC1 activity. The best characterized mTORC1 substrates are the AGC kinase p70 ribosomal protein S6 kinase (p70S6K), the translation initiation regulator 4E binding protein (4E-BP), and the proline-rich Akt substrate PRAS40, which is an inhibitor of mTORC1. By binding mTORC1, PRAS40 contributes to the inhibition of mTORC1 activity. In response to insulin, Ser183 of PRAS40 is phosphorylated by mTORC1, which releases PRAS40 from the complex and relieves its inhibitory effect on mTORC1, allowing mTORC1 to phosphorylate its downstream substrates p70S6K and 4E-BP and promote cellular growth. Furthermore, there is a negative feedback loop (NFL) that inhibits upstream insulin signaling upon mTORC1 activation: Active p70S6K phosphorylates and inhibits IRS, which prevents activation of PI3K in response to insulin.

mTORC2 is mainly regulated by growth factors, although induction by nutrients has also been described. Little is known in the art about the molecular mechanism by which insulin induces mTORC2. The known substrates of mTORC2 are the AGC kinases Akt, serum- and glucocorticoid-induced protein kinase SGK, and protein kinase C α (PKCα). AGC kinases must be phosphorylated twice to be fully active: They are phosphorylated by PDK1 in the T-loop, and in the hydrophobic motif by a PDK2. Only one PDK1 exists for all AGC kinases, but the identity of PDK2 differs among the AGC kinases. mTORC2 is a PDK2 for Akt, SGK, and PKCα, and phosphorylation of Ser473 of Akt is a commonly used readout for mTORC2 activity.

Using mTORC2 substrate AGC kinases as indicators of mTORC2 activity, the TSC1/TSC2 complex can be implicated in mTORC2 activation by insulin: TSC1/TSC2 inhibition reduces phosphorylation of the mTORC2 substrate Akt at Ser473. This result was surprising because TSC1/TSC2 inhibits mTORC1. Two models have been proposed to explain mTORC2 regulation by TSC1/TSC2, involving either direct mTORC2 activation by TSC1/TSC2, or an indirect mechanism through an active NFL inhibiting PI3K when mTORC1 was hyperactive in response to TSC1/TSC2 ablation. However, data showing that mTORC2 contributes to proliferation in TSC2-null cells suggests that mTORC2 can be active in the absence of TSC1/TSC2. A third hypothesis for mTORC2 activation is through a PI3K-independent mechanism, which has been identified in Dictyostelium. In mammals, several cellular processes that are regulated by mTORC2 have been described as PI3K independent, making the hypothesis of PI3K-independent activation of mTORC2 conceivable.

To distinguish between the possible mTORC2 activation mechanisms and to determine whether they acted independently or in combination, a mathematical dynamic network model was developed to show that different modes of mTORC2 regulation would result in distinguishable, dynamic network responses. With the mathematical model specific predictive dynamic simulations for alternative mechanisms of mTORC2 regulation have been performed and then these were experimentally validated.

There are several computational studies related to mTOR signaling known in the art. These include static network models of known molecular interactions, for example, the map for the insulin-mTOR network. Dynamic models also exist. These require information about the molecular interactions and also detailed quantitative experimental time course data, which can be generated specifically for the model or can use data from previous studies. Much of the currently available dynamic models known in the art focus on the upstream insulin signaling events, such as the binding of insulin to its receptor, and receptor autophosphorylation and receptor-mediated substrate phosphorylation, together with receptor cycling and endocytosis. More extensive models including activation of IRS, PI3K, Akt, and the NFL have been developed with specific functional emphasis on cycling of the glucose transporter GLUT4, dendritic protein synthesis, or breast cancer therapy. Other models address complex issues, such as joint regulation of the NFL by insulin and amino acids, crosstalk with epidermal growth factor (EGF) signaling and the mitogen-activated protein kinase (MAPK) pathway, and TORC1 regulation by phosphatases in yeast. Because the combined experimental-computational approaches typically address specific questions, the generated data sets are often limited, representing one or two time points, or representing limited parts of the network, such as binding of insulin and insulin-like growth factor (IGF) to their receptors.

Models for dynamic networks additionally require detailed quantitative experimental time course data and none of the existing models integrates mTORC2 regulation.

The model can be preferably parameterized with dynamic quantitative time course data and can be in particular experimentally validated. Subsequently, in silico and experimental network perturbations to simulate and experimentally test alternative network structures connecting mTORC2 to upstream insulin signalling can preferably be introduced. This approach can provide the benefit of both a structural and dynamic network analysis.

Said model and experimental testing can for example indicate that, in contrast to previous hypotheses known in the art, the TSC1/TSC2 complex was not a direct activator of mTORC2 and that mTORC2 activity was insensitive to the mTORC1-induced NFL. Although PI3K can be inhibited by the NFL, activation of the NFL-insensitive mTORC2 can also require active PI3K. Hence, all three literature-based hypotheses can preferably be excluded by the combined simulation and experimental data according to the invention. Instead, it has been postulated that insulin signalling activates mTORC2 through a PI3K that is insensitive to the NFL, thus insulin triggers signaling networks that diverge upstream of Akt. A network structure has been created that preferably fits the available experimental data and provided experimental evidence supporting the network.

Initially, a static network model in SBGN format of insulin-mTOR signaling as a means to integrate current knowledge and as a platform to guide our decision on appropriate targets for measurement has been established. The choice of boundaries for such a network and the level of molecular detail to include are in general subjective decisions. In particular, there is considerable existing knowledge concerning insulin signaling and the regulation of TOR. Although this information can be useful and therefore can be preferably used, it is advantageous to minimize the amount of details, because precise dynamics for the extended graphical model could not be defined, due to the high number of parameters and the difficulty in obtaining sufficient experimental data. Therefore, it is of advantage to preferably abstract the extended model on the basis of two main considerations. In particular, first, regulation mechanisms with an important role in dynamic behavior have to be selected, such as the activation of mTOR complexes by the presence of both amino acids and insulin, the pathways connecting these stimuli to the mTOR complexes, and the NFL from p70S6K to IRS. Second, molecules and interactions that could be reliably measured have to be selected. In order to capture the network dynamics upon starvation and in response to amino acids plus insulin (aa/insulin), the measurements should preferably be widely distributed across the network. The abundance of the Tyr1146-phosphorylated IR, the Ser636-phosphorylated IRS1, Ser473- and Thr308-phosphorylated Akt, Ser2448- and Ser2481- phosphorylated mTOR, Thr246- and Ser183-phosphorylated PRAS40, and Thr389-phosphorylated p70S6K could in particular be monitored.

On the basis of the molecules that can be measured, the network structure can preferably be condensed to minimize in particular poorly defined intermediate steps between obtainable data. The condensed network depicts insulin signaling propagating from the IR through the TSC1/TSC2 complex to the mTORC1 complex and includes p70S6K, PRAS40, and Akt. In addition, mTORC1 induction by amino acids was included. At this point, no upstream pathway regulating mTORC2 was assumed. This model formed the starting point for our dynamic study.

Studies suggesting that TSC1/TSC2 regulates mTORC2 commonly used Akt phosphorylated at Ser473 (AktpS473) as the mTORC2 readout. However, the phosphorylation of Akt in particular depends on PI3K and the phosphatidylinositol-3,4,5-trisphosphate P3 [PtdIns(3,4,5)P3] generated by PI3K, which binds to Akt and triggers its relocalization to the plasma membrane, where Thr308 is phosphorylated by PDK1 and Ser473 is phosphorylated by mTORC2. Thus, phosphorylation of Akt at either Thr308 or Ser473 depends on PI3K activity. PI3K and Akt are inhibited in the absence of the inhibitory TSC1/TSC2 complex, because of hyperactivation of mTORC1 and the NFL. Consequently, under conditions of TSC1/TSC2 deficiency and NFL activation, monitoring AktpS473 does not differentiate between PI3K, PDK1, and mTORC2 activity and therefore may not be a suitable readout to investigate the mode of mTORC2 regulation by TSC1/TSC2. In particular, other AGC kinases that are targeted by mTORC2 (SGK and PKCα) are not ideal because they have similar issues. The Rapamycin-insensitive autophosphorylation of Ser2481 (mTOR-pS2481) has been described as mTORC2 specific and as occurring in both the mTOR complexes. To determine if mTOR-pS2481 is a better readout for mTORC2 activity than is the phosphorylation of AGC kinases and if monitoring mTOR-pS2481 will distinguish between PI3K and mTORC2 activity, it has been in particular be determined that mTOR-pS2481 was a specific readout for mTORC2 activity in HeLa cells. Complex-specific immunoprecipitations using antibodies against Sin1 (for mTORC2) or Raptor (for mTORC1) have been performed to assess the amount of mTOR-pS2481 that coimmunoprecipitated. In HeLa cells mTOR-pS2481 was predominantly associated with mTORC2, and only weakly associated with mTORC1, suggesting that mTOR-pS2481 is a suitable readout of mTORC2 activity. Furthermore, whereas the mTORC1-specific readout p70S6K1-pT389 was reduced by the mTORC1-specific inhibitor Rapamycin; in agreement with Copp et al., mTOR-pS2481 was not significantly affected by short-term treatment with the Rapamycin. In contrast, the TORKinib PP242, which inhibits both mTOR complexes, reduced the abundance of mTORpS2481 in a dose-dependent manner, which is consistent with results obtained in particular with Torin1, another TORKinib. Therefore, it has been shown in advantage that mTORpS2481 is reduced by mTORC2, but in particular not by mTORC1 inactivation in specific cell types.

Because there are e.g. Rapamycin-insensitive mTORC1 functions, and also specific mTORC1 and mTORC2 components to assess the dependence of mTOR-pS2481 on the activity of the two complexes have been knocked down. When the mTORC1-specific component Raptor was knocked down, mTOR-pS2481 was unchanged; whereas there was a significant reduction in mTORpS2481 by 67% (three independent experiments, SEM 8%) when the mTORC2-specific component Rictor was knocked down. Thus, both knock down and pharmacological experiments indicated that mTORpS2481 serves as an mTORC2-specific readout in the method and the use of method according to the present invention.

To parameterize the static network model, semiquantitative dynamic phosphorylation immunoblot data for network components along the signaling cascade can preferably be generated. HeLa cells under starvation conditions can for example be analyzed, meaning that they were deprived of amino acids and growth factors for in particular 16 hours to fully inhibit mTOR network activity, and also cells that had been starved and then stimulated with aa/insulin to assure full induction of both mTOR complexes. mTOR network dynamics can be monitored from 1 min up to 2 hours after induction with aa/insulin. Signals were quantitatively analyzed. Because signal linearities are in particular critical for quantitative data generation, the linear signal-to-protein amount relationships can preferably be confirmed by detection of serial dilutions of whole cell lysates. The model parameters using the experimental mean time courses can also preferably be calibrated.

The initial concentrations of the species in their nonphosphorylated state can preferably be determined directly from the semiquantitative data. For all other species, the initial concentrations were in particular set to 0. Because it is difficult to fit large numbers of parameters to data to estimate kinetic rate constants, which are necessary to calibrate the model, the data fitting into calibration phases can preferably be divided and resolved each phase using in particular an iterative procedure. This procedure can for example be summarized by the following steps: (i) The initial values of the parameters that needed optimization were assigned by random generation; (ii) the calibration was repeated until a set of parameters with consistent values was identified; (iii) this set of parameters was fixed and the remaining free parameters were calibrated again by repeating the process. In Phase 1 of the estimation of kinetic rate constants, it might be possible in advantage to identify isolated modules that can be calibrated independently within the network. Because the IR regulation was not affected by the rest of the network, this module can be isolated and preferably three parameters can be calibrated at once: The kinetics of IR activation by insulin, dephosphorylation to a refractory state and transition to a receptive state. The present invention provides among others a model that was independent of the pathway by which mTORC2 was activated. The regulation of the mTORC2 substrate AktS473 and mTORC2 component mTORS2481 with two autoactivation mechanisms has been temporarily modelled, which can then preferably be calibrated using the Akt-pS473 and mTORpS2481 experimental datasets. This enables a person skilled in the art to reproduce Akt-pS473 activation while maintaining mTORC2 isolated from the network. During Phase 2, a total of 24 reaction rate constants can in particular be estimated using e.g. eight experimental readouts. Finally, in Phase 3, the autoactivation mechanism of Akt-pS473 can preferably be replaced with a phosphorylation mediated by mTORC2-pS2481. Because the initial induction of Akt-pS473 occurred before mTOR-pS2481 was induced, mTORC2-pS2481 alone can not reproduce the dynamics of the experimental data for Akt-pS473. mTORC2 is not the only PDK2 candidate that may phosphorylate AktS473; therefore, an additional PDK2 species can in particular be introduced and recalibrated the phosphorylation of Akt-S473 under the influence of the two kinases. In this phase, three kinetic rate constants can in particular be estimated using the Akt-pS473 experimental data.

Once this process of parameterization is completed, the experimental and simulated time courses matched well for all the analyzed mTOR network readouts. The ordinary differential equations (ODEs) and estimated parameters for the general model are provided in tables S1 and S2. Identifiability analysis, which indicates whether the parameters can be estimated with confidence from the available data, and sensitivity analysis, which indicates how sensitive model behavior is to variation in each parameter, can be set up. In particular, the identifiability analysis does not show high correlation between estimated parameters indicating that they can be identified.

If the parameterized model correctly represents the biological mTOR network dynamics in response to aa/insulin, model simulations must preferably accurately reflect the dynamics of known network responses to a gradual perturbation. To validate the mTORC1 branch of the model, it is in particular possible to pertubate the network by gradually inhibiting mTORC1 first in silico, and then experimentally with an inducible Raptor knock down (shRaptor) cell line. The model can be used to simulate the effect of gradual mTORC1 inhibition on the activation dynamics of the direct mTORC1 substrate p70-S6K-pT389, at several time points after induction with aa/insulin. The model can in particular predict a constant increase in p70-S6K-pT389 signal from 10 min to 2 hours after induction. Furthermore, the model also can predict that p70-S6K-pT389 would decrease starting 10 minutes after induction in a near linear manner in response to gradual Raptor (mTORC1) inhibition, whereas there should be no detectable increase or Raptor dependent change in p70-S6K-pT389 below 5 min after induction. The predicted quantitative p70S6KpT389 response upon gradual mTORC1 inhibition can be tested in particular at specific time points and it can be found that the dynamic simulations for p70-S6K-pT389 were validated by experimental data of a person skilled in the art. For example, both the simulations and the experimental results for the change in p70-S6K-pT389 in response to gradual Raptor inhibition at 20 and 45 min after induction with as/insulin matched, showing an overall increase in signal at 45 min after induction and no signal at 3 min after induction.

Hence, we confirmed that the model accurately simulated the dynamic behavior of the mTORC1 substrate p70-S6K-T389 both in response to aa/insulin and to a network perturbation (Raptor inhibition). Importantly, this was performed with an experimental perturbation that was not used for parameterization.

The mechanism by which TSC1/TSC2 influences mTORC2 activity is currently unclear with both a direct activation of mTORC2 by TSC1/TSC2 and an indirect effect of the TSC1/TSC2 through mTORC1 and the NFL suggested. The evidence for these mechanisms involves experimental designs that can affect the system in a manner that can complicate the interpretation, for example, overexpression of NFL-independent PI3K versions, or TSC2 ablation in combination with subsequent in vitro mTOR kinase assays.

To establish an approach with minimal complicating manipulations, the present invention suggests preferably to apply a combined experimental-computational strategy. Because the different suggested molecular mechanisms by which TSC1/TSC2 regulates mTORC2 should result in mechanism-specific changes in the dynamics of the mTORC2 readouts, the response of the readouts to network perturbations can be predictable and distinguishable by the dynamic network method and the model according to the invention. On the basis of the existing literature, three different hypotheses for the molecular connection or lack thereof between TSC1/TSC2 and mTORC2 can be postulated by a person skilled in the art: (Hypothesis 1) TSC-dependent: TSC1/TSC2 directly activates mTORC2 in response to insulin, and has opposite effects on mTORC1 and mTORC2; (Hypothesis 2) NFL-dependent: mTORC2 is activated by insulin through PI3K, but independently of Akt and TSC1/TSC2, however mTORC2 activity can be inhibited indirectly by TSC1/TSC2 ablation through NFL-mediated inhibition of PI3K; and (Hypothesis 3) PI3K-independent: mTORC2 is activated by insulin in a manner that is independent of both TSC1/TSC2 and PI3K.

These three alternative modes of mTORC2 regulation can be translated into the corresponding network structures, re-using the same kinetic parameters of the previous method and the model according to the invention. To keep the hypotheses as comparable as possible, each hypothesis can preferably share the network topology of the general model but assumed a specific mTORC2 upstream regulator. Following rationale can therefore be adopted: let M be a model fitting some data and S a species in M. If a modifier (F) directly upstream of S is selected and re-calibration solely of the dynamics of S maintains a close fit between the simulated time course for S and the experimental data for S, then all time course curves downstream of S will continue to fit their corresponding data. The model output however following perturbation of F will not necessarily maintain a fit with the corresponding data when the introduced upstream connection is incorrect.

According to the invention, three new models, in which the network and the parameters of our previous model were maintained, and only the mTORC2 kinetics were re-estimated according to each hypothesis (tables S1, S3). The total goodness-of-fit for the general model and each hypothesis showed that no model can be statistically rejected (table S4). For each hypothesis, time course simulations and experimental validation for the mTORC2 readouts mTOR-pS2481 and Akt-pS473, the PI3K readout Akt-pT308, and the mTORC1 substrate p70S6K-pT389 have been performed. The simulations matched the experimental time courses, indicating that the hypotheses according to the invention were compatible with the observed dynamics for mTORC2 activation and more generally for the mTOR signaling network.

Next, a gradual network perturbations that prevented either TSC1/TSC2 activity (TSC1/TSC2 inhibition), the NFL (mTORC1 inhibition), or insulin activation of the mTOR complexes (PI3K inhibition) can preferably be introduced. For each of the three perturbations and each of the three hypotheses, the dynamic network response of the readouts of mTORC2 activity, of mTORC1 activity, and of PI3K activity can be modelled.

From the information obtained from the alternative simulations, experimental setups and time points have been identified after induction with aa/insulin for the mTORC2 readouts (mTORpS2481, AktpS473) that would specifically distinguish between Hypothesis 1, 2, and 3. These predictions were then tested experimentally (FIG. 6-8).

The models according to the invention predicted that for gradual TSC1/TSC2 inhibition, if Hypothesis 1 was correct, then the abundance of mTORpS2481 would be affected by TSC1/TSC2 inhibition in a near linear manner down to minimum levels. In contrast, for Hypothesis 2, simulated mTOR-pS2481 dynamics were only slightly affected by TSC1/TSC2 inhibition, and for Hypothesis 3, mTOR-pS2481 was not affected. For Akt-pS473 dynamics, if Hypotheses 2 or 3 are correct, then Akt-pS473 should only be weakly affected 5 min after induction and should exhibit a gradual decrease starting 10 min after induction for the rest of the time course. For Hypothesis 1, the model predicted a stronger reduction of Akt-pS473 in response to TSC1/TSC2 inhibition at all time points after induction, compared to the reduction predicted for Hypothesis 2 or 3. Thus, these simulation results indicated that observation of mTOR-pS2481 in response to gradual TSC1/TSC2 inhibition should effectively distinguish Hypothesis 1 from the two other hypotheses.

For experimental testing, an inducible short-hairpinTSC2 (shTSC2) cell line and induced TSC2 knock down for 0, 1, 2, or 3 days can in particular be generated, which resulted in a gradual decline in the amount of TSC2. After starvation, cells can be stimulated with aa/insulin for 5, 30, and 60 min. Because TSC1/TSC2 is a negative regulator of mTORC1, p70S6 KpT389 increased as expected with gradual TSC2 inhibition. Relative quantitations for AktpS473 and mTOR-pS2481 at 60 min after aa/insulin induction are shown for the simulations of the three hypotheses, and for the experimental data. Both the time course analysis and the analysis of the effect of increasing knockdown of TSC2 on Akt-pS473 show that Hypothesis 2 or 3 may be correct. Hypothesis 1 of direct TSC1/2 activation of mTORC2 was clearly excluded because mTORpS2481 was unaffected by TSC2 inhibition at all time points and at all amounts of TSC1/TSC2 inhibition. The experimental data are in line with reported findings indicating that TSC1/TSC2 does affect Akt-pS473. However, according to the simulations, the regulation of Akt-pS473 by TSC1/TSC2 depends on the NFL and PI3K and thus in the absence of TSC1/TSC2 mTORC2-mediated phosphorylation of AktS473 is indirectly inhibited. Because the direct mTORC2 readout mTOR-pS2481 was unchanged in the absence of TSC1/TSC2, we can rule out TSC1/TSC2 as a direct activator of mTORC2.

The same procedure that can be used to identify the best experimental condition to assess can preferably be followed if TSC1/TSC2 indirectly controls mTORC2 through the NFL (Hypothesis 2). For gradual mTORC1 inhibition and consequent NFL inhibition, all three model structures predicted an increase of AktpS473 with decreasing mTORC1 activity (FIG. 5B). The simulations also predicted that mTORpS2481 would remain unaffected in Hypotheses 1 and 3 and would gradually increase in response to mTORC1 inhibition in Hypothesis 2 starting 40 min after induction with aa/insulin. This effect should be clearly experimentally visible at 100 min after induction with aa/insulin and this paradigm can be used to distinguish Hypothesis 2 from the other hypotheses.

For experimental testing, the specific mTORC1 component Raptor can gradually be inhibited by knocking down Raptor in an inducible shRaptor cell line for 0, 1, 2, or 3 days. Cells can be starved and stimulated with aa/insulin for 45, 100, and 180 min. Verification of effective mTORC1 inhibition in this experimental setup can be performed by monitoring the abundance of p70-S6K-pT389, which showed the expected reduction in response to decreased Raptor. Relative quantitations of Akt-pS473 and mTOR-pS2481 in response to gradual Raptor inhibition are shown for the simulations of the three hypotheses and for experimental data at 100 min after induction with aa/insulin. As predicted for all three hypotheses, Akt-pS473 showed a significant increase with declining Raptor levels, because the NFL is inhibited. The abundance of Akt-pT308 also increased as mTORC1 was inhibited. In contrast, mTORpS2481 remained unaffected at all time points after induction with aa/insulin and at all Raptor levels, which excludes Hypothesis 2. Therefore, the method and the model according to the invention and the experimental testings allows a person skilled in the art to exclude the previously suggested hypothesis of an indirect mTORC2 regulation by TSC1/TSC2 and the NFL. Hence, mTORC2 is neither directly nor indirectly regulated by TSC1/TSC2.

Having excluded both Hypothesis 1 and 2 and established that mTORC2 induction was independent of the NFL that inhibits IRS1 and thus PI3K activity, that can be directly tested if the model and experimental testing would confirm Hypothesis 3 that PI3K inhibition would not affect mTOR-pS2481 induction by aa/insulin. For gradual PI3K inhibition, the simulations predicted Akt-pS473 in all three hypotheses would be reduced to a minimum level at all time points after induction with aa/insulin. In contrast, the model predicted that mTORpS2481 would remain either unaffected by PI3K inhibition (Hypothesis 1, 3), or to decline with decreasing PI3K starting 20 min after induction (Hypothesis 2). Because Hypotheses 1 and 2 were already excluded, we expected PI3K inhibition to result in the mTORpS2481 behavior predicted by Hypothesis 3.

To experimentally test the validity of Hypothesis 3, cells can in particular be starved, PI3K can be preferably gradually inhibited with increasing Wortmannin concentrations, and mTOR signaling can be induced by aa/insulin for 30 and 50 min. If a person skilled in the art would chose a maximal Wortmannin concentration of 100 nM, which is class I PI3K specific. Quantitification of simulated and experimentally measured Akt-pS473 and mTORpS2481 in response to gradual PI3K inhibition are shown for 30 min after induction with aa/insulin (FIG. 8B). In agreement with the method and the model according to the invention, the dynamics of Akt-pS473 closely resembled the PDK1 phosphorylation of Akt-T308, decreasing as PI3K was inhibited. The mTORC1 target p70-S6K-pT389 behaved similarly. In line with state of the art, and as predicted by all three hypotheses, Akt-pS473 was already inhibited at 5 nM Wortmannin, and was strongly inhibited by concentrations of 10 nM Wortmannin or higher. Surprisingly, mTORpS2481 also was inhibited by Wortmannin concentrations of 20 nM or higher. Thus, the method and the model according to the invention and the experimental testing also exclude Hypothesis 3, because mTORC2 activation appears to depend on PI3K activity.

The combined experimental-computational approach showed that insulin regulates mTORC2 through a Wortmannin-sensitive enzyme (likely PI3K), and that mTORC2 is neither affected by the NFL nor by TSC1/TSC2. Therefore, one skilled in the art had to postulate a Hypothesis 4: There is another kinase, in particular a Wortmannin-sensitive, but IRS1-independent PI3K species, that is activated by the IR and stimulates mTORC2 in response to insulin. The method and the model according to the invention did not require recalibration, because the new branch for mTORC2 activation by insulin was similar to the PI3K-independent Hypothesis 3, but contained the new proposed PI3K, which is sensitive to Wortmannin and refractory to the NFL.

It can be in particular experimentally be verified that this Hypothesis 4 model fitted the data by showing that the simulated time courses matched the experimental readout dynamics. Next, the dynamic network response under all previously tested network perturbations (gradual TSC1/TSC2, mTORC1, or PI3K inhibition) can be modelled, and compared the simulations to the experimental data. For each of the three network perturbations, the predictions for all readout dynamics matched the experimental data. The identifiability analysis reports low correlation between the estimated parameters, indicating that the parameters can be identified. Thus, the new network model of a PI3K-species-dependent and NFL-independent mTORC2 induction accurately predicted the responsiveness of mTORC2 to PI3K inhibition, and mTORC2 insensitivity to gradual TSC1/TSC2 or mTORC1 inhibition.

Because a model for mTORC2 activation through an NFL-insensitive PI3K was unexpected, additional experimental testing have been performed. To confirm that the reduction of mTOR-pS2481 in response to Wortmannin was associated with mTORC2, cells have been in treated with PP242 or Wortmannin, or knocked down Raptor and then immunoprecipitated mTORC2 with an antibody recognizing Sin1. It can be shown that both PP242 and Wortmannin significantly reduced mTOR-pS2481 associated with the immunoprecipitated mTORC2, but that mTORC1 inhibition by shRaptor did not affect mTOR-pS2481 associated with the immunoprecipitated mTORC2. These results are consistent with the whole cell lysate experiments and support our previous conclusion that Wortmannin inhibits mTORC2.

To verify the PI3K specificity of the Wortmannin effect on mTORC2, PI3K can preferably be inhibited by two alternative means, with another PI3K inhibitor LY294002 or by overexpression of the PI3K antagonist PTEN. It can be shown that mTORpS2481 was reduced in cells exposed to LY294002 at concentrations as low as 1 µM (FIG. 10C) and in cells overexpressing PTEN. Thus, three separate experimental approaches indicated that mTORC2 activation depends on PI3K.

The Hypothesis 4 model predicted that the PI3K-dependent, NFL-insensitive activation of mTORC2 should be insensitive to Akt. Myristoylated Akt (myr-Akt) has been overexpressed, which is constitutively recruited to the membrane and constitutively active even without insulin, or a kinase-dead myr-Akt variant (myr-Akt K179M) in HeLa cells and C2C12 cells and monitored the activity of mTORC1 and mTORC2. For cells expressing the constitutively active Akt, phosphorylation of the mTORC1 substrate p70-S6K-T389 can be increased by myr-Akt; whereas it can be decreased in the cells expressing the myr-Akt K179M. In contrast, the mTORC2 readout mTOR-pS2481 can be unchanged in the presence of either of the two myrAkt constructs. It was confirmed that mTOR-pS2481 specifically reflected mTORC2 activity in C2C12 cells because the amount of mTOR-pS2481 was decreased in response to the mTOR kinase inhibitor PP242, but was unaffected by the mTORC1-specific drug Rapamycin. Thus, mTORC2 activity was not induced by Akt.

The present invention presents a dynamic mTOR network model, which is based on an integrated experimental-computational approach. Three different network structures for mTORC2 induction by insulin, which guided experiments to test the hypotheses, have initially been postulated. The results of the simulations and experimental data indicated none of the previously suggested mechanisms of mTORC2 activation were accurate: TSC1/TSC2 is not a direct activator of mTORC2; TSC1/TSC2 also does not indirectly control mTORC2 through inhibition of PI3K by the NFL; and mTORC2 activation depends on PI3K. However, the PI3K-dependent mTORC2 activation is insensitive to the NFL. Therefore, it has been postulated an activation pathway involving a PI3K variant that is independent of the NFL and we tested this hypothesis by developing a network structure that matched the observed mTOR pathway dynamics, performing simulations, and then experimentally verifying the predictions. Consistent with this model, experimental testing showed that mTORC2 activity was sensitive to different modes of PI3K inhibition, but was insensitive to constitutive activation of Akt in several cell types.

Dynamic modelling can preferably be used extensively in the study of cell signalling networks, yielding many important insights related to cellular behavior. Here, dynamic modelling was in particular used to discriminate between alternative network structures, in particular alternative modes of mTORC2 regulation. It is known in the art that others have used similar approaches to study the possible network structures for the segment polarity gene network and the extracellular signal-regulated kinase pathway. Although network testing can be performed using a Bayesian statistical approach, to perform experimental testing to distinguish between the proposed network topologies has been chosen, because our simulated conditions and outputs were experimentally tractable.

Because our approach relied on the simulation and experimental testing of differential network dynamics under the assumption of alternative network structures, this may have enabled us to identify a network structure for insulin-regulated mTORC2 activation that is different from any other regulatory mechanism proposed thus far. Our approach enabled exploration of the network dynamics of endogenous proteins; whereas other purely experimental studies have relied on approaches that interfere with the dynamics under investigation, for example, overexpression of mutagenized network components that uncouple upstream cues from feedback inhibition. It is also confirmed mTOR-pS2481 as a specific and direct readout for mTORC2 activity, which unlike other mTORC2 readouts does not require activation by the NFL-dependent PI3K. Because changes in network dynamics have been used as a means of testing alternative network structures and we used the phosphorylation status of mTOR Ser2481 at the readout of mTORC2 activity, this work is distinguishable from earlier studies and these differences in the approach may account for the conclusions that mTORC2's induction is independent of TSC1/TSC2 and the NFL.

In addition to revealing a new mechanism of regulation of mTORC2 in response to insulin, the analyses according to the invention revealed additional complexity in the regulation of Akt. Model parameterization revealed more complex dynamics for mTORC2s target site Ser473 in the AGC kinase Akt than for Ser2481 in mTOR, and this can not be explained exclusively by mTORC2 activation. To integrate Akt-pS473 dynamics into the dynamic network model a second PDK2 had preferably to be estimated that accounted for the early peak of Akt-pS473 at 3 min after induction with aa/insulin. In addition to mTORC2, various other PDK2 candidates for Akt have been reported, including DNA-PK, ILK, ATM, MAPKAPK-2, PKC, Pak1, and even Akt autophosphorylation, any of which may contribute to Akt-pS473 dynamics under different metabolic conditions. Furthermore, it can be observed that upon network perturbations involving the NFL, the dynamics of mTOR-pS2481 were different than those of AktpS473, with only the latter resembling the PDK1 phosphorylation on Thr308 of Akt. Thus, the AGC kinase targets of mTORC2 were not suitable readouts of mTORC2 activity and can not be used in a method or a system according to the invention to analyze the dependence of mTORC2 activity on TSC1/TSC2, because TSC1/TSC2 inhibition induces NFL that inhibits PI3K, which in turn can affect AGC kinase phosphorylation by their PDK2s, independently of the actual PDK2 activity. Because of this complexity in Akt phosphorylation dynamics, mTORpS2481 was preferably chosen as the readout of mTORC2 activity. Although mTOR-pS2481 has been identified on Raptor-associated mTOR (mTORC1) and is Rapamycin sensitive in 3T3L1 adipocytes; Rapamycin did not affect mTORpS2481 in whole cells lysates of HEK293 cells or Tag Jurkat cells. Soliman et al. concluded that the Rapamycin-insensitive, mTORC2-associated mTORpS2481 signal predominated over the Rapamycin-sensitive, mTORC1-associated mTORpS2481 signal in HEK293 cells, possibly due to a relatively low abundance of mTORC1 compared to mTORC2. We also found that mTORpS2481 was predominantly associated with mTORC2 in HeLa cells, which can be in particular used for the experimental testing in connection with the present invention.

Our model assumes that the NFL is exclusively executed by p70-S6K, phosphorylating and thereby inhibiting IRS. GRB10-dependent IR inhibition in response to activated mTORC1 may also contribute to the NFL, thus adding more complexity to the NFL mechanism. Although the identification of GRB10 as a contributor to the NFL is mechanistically relevant, the effect is the same, namely the inhibition of IRS in response to mTORC1 activity, and is readily detected by the reduction of Akt-pT308 upon high mTORC1 activity. Given the need to reduce the complexity of our model to enable parameterization, we did not introduce these mechanisms separately into our model, but combined them into one step.

The data according to the invention suggested that mTORC2 activity is in particular independent of the NFL, which is consistent with previous studies. To ensure that full activation of both mTOR complexes can be achieved and thus activation of the NFL, the cells can preferably be stimulated with both amino acids and insulin induction. The activation of the NFL starting 45 min after induction, as measured by IRS1pS636 can be experimentally observed. Thus, under conditions in which the NFL was active, network perturbations inducing or inactivating the NFL did not affect mTORC2 activity as measured by mTOR-pS2481.

Although mTORC2 activity can be independent of the NFL, it was dependent on PI3K activity. The dynamics of mTOR-pS2481 were not affected by inhibition of the TSC1/TSC2 complex or mTORC1, but were inhibited by pharmacological inhibition of PI3K or reduction in its downstream signaling by overexpression of PTEN. Because pharmacological inhibitors can have off target effects, we used a maximum Wortmannin concentration of 100 nM, which has been reported to specifically inhibit only class I PI3Ks. Although it can be found that mTOR-pS2481 dynamics were less sensitive to Wortmannin than were the dynamics of the PDK1-targeted AktpT308, mTOR-pS2481 inhibition occurred with Wortmannin concentrations as low as 20 nM, indicating that mTORC2 inhibition was dependent on class I PI3K activity, which is consistent with previous studies. PDK1-deficient cells exhibited a Wortmannin-sensitive phosphorylation on Ser473 of Akt, which, while not previously linked to mTORC2 activity, supports our hypothesis of a PI3K-dependent, but Akt-independent (and therefore NFL- and TSC1/TSC2-independent) mTORC2 induction. This proposed PI3K regulatory mechanism according to the invention was surprising because PI3K induction by insulin is generally thought to be IRS dependent, and IRS is inhibited by active p70S6K and thereby mediates the NFL. Consequently, it can be proposed that mTORC2 is induced by a PI3K species that is different from the PI3K that induces mTORC1, because mTORC1 activity strictly depends on TSC1/TSC2 and the NFL.

In the new proposed model and the method according to the invention for mTOR activation by insulin and amino acids, Akt should activate mTORC1 through the canonical insulin-IRS-PI3K-Akt-TSC1/TSC2 pathway, but should not participate in mTORC2 activation, which is induced by a different PI3K. Indeed, it can be shown in several cell lines that constitutively active Akt did not induce mTORC2 activity (mTOR-pS2481), although it did activate mTORC1. Two studies have reported mTORC2 regulation downstream of PI3K that differs from the canonical Akt-TSC1/TSC2 signaling axis. Direct PI3K-dependent induction of mTORC2 by PtdIns(3,4,5)P3 binding has been observed and ribosomal proteins have been described to bind and activate mTORC2 in a PI3K-dependent manner. These mechanisms may require further study which will likely reveal further molecular connectors of PI3K and mTORC2.

What kind of mechanism can account for the observed NFL insensitivity of PI3K for mTORC2 induction? The NFL is mediated by IRS, which activates PI3K downstream of insulin and the IR. However, PI3K activity can be also observed in cells devoid of IRS protein, and the IR may activate PI3K in part by direct binding. Such IRS-independent PI3K activity might mediate NFL-independent stimulation of mTORC2 activity. For class I PI3Ks, there are at least seven alternative regulatory subunits and four alternative catalytic subunits, and specific combinations of these subunits might mediate different physiologic outputs. Receptor binding and abundance of the isoforms is differentially regulated by metabolic inputs such as growth factors or amino acids. This apparently IRS-independent PI3K activation can be in particular be detected because simultaneous stimulation can be used with both insulin and amino acids to assure full induction of both mTOR complexes. In contrast, prior studies have mainly tested the effect of a single stimulus on class I PI3K activation. In a physiological environment, cells are confronted with multiple simultaneous inputs, and full activation of some PI3K isoforms can require multiple upstream inputs. Hence, the existence of an NFL-independent class I PI3K might be conceivable and might requires further investigation.

In conclusion, the suggested novel network structure, connecting preferably mTORC2 to its upstream inputs, is supported by the existing literature known in the art and reveals a need to re-evaluate the mTORC2 regulatory mechanisms. The complexity of differential mTORC1 and mTORC2 regulation that highlights the need to apply integrated computational-experimental approaches to understand complex signaling and regulatory networks. Because the dynamic model and the method according to the invention of mTORC1 and mTORC2 signaling is a mathematical representation of the differential signal transduction toward mTORC1 and mTORC2, it can in particular enable simulation of the signaling dynamics that are transmitted through the network under different metabolic conditions, importantly, despite being a simplification, the model simulations and the method according to the invention mathematically showed that the simplified system was sufficient to explain the experimental observations. The fully parameterized model and the method according to the invention provides a resource for future work and other modelling efforts can extend and build upon it, as well as provide a framework on which pharmacological interventions can be tested.

Experiments were performed in particular in HeLa α Kyoto cells and C2C12 myoblasts. For inducible knock down of Raptor or TSC2, cells were transduced with lentivirus encoding the tetracycline-sensitive tTR-KRAB repressor and a DsRed reporter. Cells were subsequently transfected with lentivirus encoding the specific shRNA, and a GFP reporter, (pLVTH vector), both preferably under the control of tTR-KRAB. For lentivirus-mediated knock down of Rictor a pLKO.1-based short hairpin construct specific for Rictor (Addgene plasmid 1853), as well as a scrambled control sequence (Addgene plasmid 1864) can in particular be supplied from Addgene. HeLa cells were transfected with viral supernatant twice as described previously and harvested 60 hours after transfection.

Plasmids can be ordered from Addgene: N-terminally HA-tagged pSG5L HA PTEN wt (#10750), N-terminally myristoylated and HA-tagged pLNCX.myr.HA.Akt1 (#9005), and N-terminally myristoylated and HA-tagged, kinase-dead pLNCX.myr.HA.Akt1 K179M (#9006). Transfection was performed with 6 µg per 6 cm dish using JetPEI reagent according to the manufacturer's instructions. Cells can be in particular harvested 24 hours after transfection.

The antibody recognizing PRAS40 (Ser183 phosphorylated) can be purchased from IBL, Hamburg, Germany. The polyclonal antibody recognizing PRAS40 (Thr246 phosphorylated) can be purchased from Biosource, Camarilla, Calif., USA. The monoclonal antibody recognizing GAPDH can be purchased from Abcam, Cambridge, UK. The antibody recognizing Rictor can be purchased from Bethyl. Horseradish peroxidise-conjugated goat anti-mouse and goat anti-rabbit IgG can be purchased from Pierce biotechnology (Thermo Scientific, Rockford, Ill. USA). Antibodies recognizing Akt, Phospho-Akt (Thr308), Phospho-Akt (Ser473), Phospho-IGF-I Receptor β (Tyr1131)/Insulin Receptor β (Tyr1146), IRS-1, Phospho-IRS-1 (Ser636/639), mTOR, Phospho-mTOR (Ser2448), Phospho-mTOR (Ser2481), PRAS40, p70 S6 Kinase, phospho-p70 S6 Kinase (Thr389), TSC2 can be purchased from Cell Signalling Technology, Danvers, Mass., USA. The antibody recognizing insulin Rβ can be purchased from Santa Cruz Biotechnology, Santa Cruz, Calif., USA. Rapamycin and LY294002 were purchased from Calbiochem, Merck, Darmstadt, Germany. PP242 and Wortmannin can be purchased from Sigma Aldrich, St. Louis, Mo., USA. Chemicals were supplied by Carl Roth, Karlsruhe, Germany if not indicated otherwise.

Immunoprecipitations can in particular be performed as described elsewhere. Lysis buffer can preferably be complemented with protease inhibitors (Complete; Roche, Mannheim, Germany), Phosphatase Inhibitor Cocktail 2, Phosphatase Inhibitor Cocktail 3 (both Sigma Aldrich, St. Louis, Mo., USA), and PP242 to inhibit residual mTOR activity after the time of lysis. Immunoprecipitations were performed with 5 µg/ml antibody [antibody recognizing Sin1, Raptor, or rabbit IgG (all Bethyl)] and with magnetic Dynabeads Protein G (Invitrogen).

For calibration data sets, in particular HeLa cells can be starved for serum and amino acids by exchanging standard growth medium for Hank's Buffered Salt Solution (HBSS) (PAN Biotech GmbH, Aidenbach, Germany) over night to inhibit mTOR pathway activity. After 16 hours of starvation, mTOR signaling was restimulated with DMEM containing amino acids and supplemented with 100 nM insulin (Sigma Aldrich, St. Louis, Mo., USA).

Gradual knockdowns of Raptor or TSC2 can preferably be established by induction with 5 µg/ml doxycycline (Calbiochem, Merck, Darmstadt, Germany) for 0, 1, 2, or 3 days. Cells can be starved for 16 hours in HBSS and mTOR signaling was induced with DMEM (PAA, Pasching, Austria) supplemented with 100 nM insulin. PP242 and Rapamycin can for example be added 1 hour prior to lysis. Wortmannin or LY294002 can in particular be added 30 min prior to and during the stimulation with DMEM supplemented 100 nM insulin. Cells can for example be washed once with PBS and lysed with TNE lysis buffer [50 mM Tris HCL pH8.0, 150 mM NaCl, 1% v/v TritonX-100 (Calbiochem, Merck, Darmstadt, Germany), Complete (Roche, Mannheim, Germany), Phosphatase Inhibitor Cocktail 2, Phosphatase Inhibitor Cocktail 3 (both Sigma Aldrich, St. Louis, Mo., USA)]. Protein concentrations can preferably be measured (Protein Assay Dye Reagent Concentrate, Bio-Rad, Hercules, Calif., USA) according to manufacturer's protocol. Concentrations can for example be adjusted with lysis buffer. Lysates can be in particular diluted in sample buffer (5×: 6 ml glycerol, 0.6 ml beta-mercaptoethanol, 1.0 g SDS, 3.75 ml 1 M Tris pH 6.8, 2 mg bromophenol blue, 2 ml H2O). Whole cell lysates can for example be analyzed using SDS-PAGE gels. Proteins can preferably be transferred to PVDF membranes (Millipore, Billerica, Mass., USA), blocked with 5% BSA in TBST (8 g NaCl, 0.2 g KCl, 8 g Tris, pH 7.4, 0.1% Tween 20) for a minimum of 30 min and incubated with the primary antibody in 5% BSA in TBST over night, shaking at 4° C. Blots can for example be washed 3× with TBST, incubated with secondary antibodies coupled to HRP, and were washed 3× with TBST before detection.

HRP can for example be detected with the ECL Western Blotting Substrate or the SuperSignal West Femto reagent [Pierce Biotechnology (Thermo Scientific, Rockford, Ill. USA)], and the emitted light can in particular be detected and quantified with a chemiluminescence imaging analyzer (LAS4000mini; Fujifilm, Tokyo, Japan). Obtained images can preferably be analyzed with Multi-Gauge version 3.0 software (Fujifilm, Tokyo, Japan). Local background can for example be subtracted. All data can in particular be normalized against GAPDH. Representative blots were exported as TIF-files and processed with Adobe Photoshop.

CellDesigner 4.2 (97) can be used to construct the model network topology in SBGN (59). COPASI 4.7.34 (98) can be used for all deterministic simulations, parameter estimations, parameter scanning and sensitivity analysis. The deterministic simulation algorithm (LSODA) can be configured with parameters: Duration (1440), Interval Size (1), Intervals (1440), Integrate Reduced Model (0), Relative Tolerance (1e-06), Absolute Tolerance (1e-12), Max Internal Steps (10000). The algorithm can be used for parameter estimation was Simulated Annealing (99, 100), configured with e.g. parameters: Start Temperature (1), Cooling Factor (0.85), Tolerance (1e-06), Random Number Generator (1), Seed (0). The parameter estimation weight method can be Mean Square and the experiment type can be Time Course. The initial concentration of the species in non-phosphorylated state can be fixed to the maximum intensity of the third quantile time course, computed from the four experimental datasets, of the corresponding experimental phosphorylated protein. This can ensure that the modelled kinases does not saturate their substrates and that the level of concentration of the substrates remained small. The initial concentration of the species in any other state was fixed to 0. The initial concentration of PDK2 can be assumed equal to the concentration of the beta subunit of the IR because the two species are directly connected in the model. In the absence of experimental data for the TSC complex, the initial concentration can be assumed to be 10. The models were formalized using only mass action reactions. For each phase, the kinetic rate constants can be estimated by running 350 independent calibrations, each initialized with a random initial configuration of the parameters. The parameter values were constrained within the interval [1e-04, 1], except for the Akt parameters, which were constrained within the interval [1e-04, 10]. For each calibration phase (F), the solutions of the estimations consistent with the data and achieving the lowest root mean square error (RMSE) can be selected as the best solutions set (BS). Among these, the solution closest to the centroid of the BS cluster in the parameter space can in particular be selected using the following formula:

$$\underset{S \in BS_F}{\operatorname{argmin}} \sum_{i=1}^{N} (S(p_i) - \mu_i)^2$$

where, $$BS_F = \left\{ \begin{array}{c} x \mid \forall\, y \in AllSolutions, \\ RMSE(\operatorname{Model}(x), \operatorname{Data}) \leq RMSE(\operatorname{Model}(y), \operatorname{Data}) \end{array} \right\}$$

$p_i$ is preferably the $i^{th}$ estimated parameter in S, $\mu_i$, is the $i^{th}$ parameter mean computed from $BS_F$ and N is the number of estimated parameters.

Model identifiability based on correlation analysis of sensitivity trajectories can be calculated using SBToolbox2 and SBPDToolbox (101) for MATLAB. SBMLToolbox 4.0.1 (102) can be used to import our SBML models into SBToolbox2. Identifiability analysis tables for the general model.

All parameter values for the final models are given in tables S2-S3. The sensitivity analysis algorithm can be configured for time series e.g. with parameters: Delta Factor (0.001) and Delta Minimum (1e-12). COPASI and CellDesigner can also be used to export the models as SBML Level 2 Version 4. CellDesigner was used to generate the extended mTOR network model in SBGN graphical notation.

The statistical and programming language R v. 2.12.1 can be used to calculate the statistics and generate the plots. The Standard Error of the Mean (SEM) was chosen to estimate the statistical variability of the measured samples of experimental time course. Model goodness-of-fit can be defined by computing Akaike information criterion and calculated as follows:

$$\chi^2 = \sum_{i=1}^{N} \left( \frac{y_i - \mu(d_i)}{\sigma(d_i)} \right)^2$$

where in particular N is the number of experimental data points, $y_i - \mu(d_i)$ is the $i^{th}$ residual, between the simulated and the experimental mean data point, which can be normalized by the standard deviation of the same data point. For the general model and the four hypotheses, and Akaike information criterion measures are provided in table S4. Tukey's Honest Significant Differences (HSD) test, in conjunction with one-way analysis of variance (ANOVA), can be used as statistical test for multiple comparisons among groups of experimental data. Furthermore, the present invention is described in connection with an insulin-TOR-AMPK model. mTOR kinase is a central controller of cellular growth and metabolism and is conserved in all eukaryotes. mTOR controls anabolic and catabolic processes, including translation, ribosome biogenesis, and autophagy in response to nutrients (amino acids), energy, and growth factors (insulin). mTOR exists in two multiprotein complexes, mTOR complex 1 (mTORC1) and mTOR complex 2 (mTORC2) which are functionally and structurally distinct: mTORC1 contains Raptor and PRAS40 as specific binding partners and controls cellular growth, mTORC2 comprises mSIN1, PRR5/PRR5L, and Rictor and controls apoptosis as well as spatial growth via the actin cytoskeleton.

Being a central growth regulator, mTOR is tightly embedded into a complex signalling network transducing insulin signals via the insulin receptor (IR), insulin receptor substrate (IRS), class I phosphatidylinositol 3-kinases (PI3K), phosphoinositide-dependent protein kinase 1 (PDK1), and the AGC kinase Akt (also known as PKB). Akt inhibits the tuberous sclerosis complex 1/2 (TSC1TSC2) dimer, which is the inhibitory GTPase-activating protein (GAP) for Rheb [1-4]. Via this cascade, Akt induces mTORC1. mTORC1 phosphorylates S6kinase (p70-S6K), the translation initiation regulator 4E binding protein (4EBP), and the mTORC1-inhibitory proline rich Akt substrate PRAS40. Whereas PRAS40 inhibits mTORC1 activity, p70-S6K and 4E-BP mediate mTORC1 downstream effects. Furthermore, active p70-S6K phosphorylates and inhibits IRS, which consequently cannot activate PI3K in response to insulin. This mechanism results in a negative feedback loop (NFL), which inhibits upstream insulin signalling upon mTORC1 activation. We have recently modelled this network and shown that whereas mTORC1 is induced via the above described signalling cascade, mTORC2 induction occurs via a distinct PI3K which is insensitive to the NFL.

mTOR does not only respond to the insulin network but is also connected to many other signalling cascades including AMP-dependent kinase (AMPK), Wnt-signalling, and the MEK/Erk pathway. To incorporate further kinase inputs into the dynamic network model according to the invention it can for example be focussed on the development of an AMPK module.

AMPK turns on catabolic ATP-generating pathways and shuts off ATP-consuming anabolic processes such as ribosome biogenesis and translation, in part via inactivation of mTORC1. AMPK is activated by both energy deprivation and the kinase LKB1 (or STK11). Inhibition of glycolytic flux leads to a high AMP/ATP ratio, activating AMPK by direct, allosteric AMP binding. LKB1 activates AMPK by phosphorylating AMPK-T172, and thereby negatively regulates mTORC1. Although LKB1 seems to be the main upstream kinase of AMPK, LKB1 also phosphorylates twelve other kinases, termed AMPK-related kinases. The physiological functions of these kinases are still poorly understood by persons skilled in the art. Apart from LKB1 several other kinases can phosphorylate AMPK-T172 independently of the cellular energy status, including $Ca^{2+}$-sensitive calmodulin-dependent protein kinase kinase (CaMKK) and TGFβ-activated kinase-1 (TAK1/MAP3K7). Also ataxia-telangiectasia mutated (ATM) kinase or inositol-requiring enzyme 1 (IRE1) dependent induction of AMPK have been reported.

To inhibit mTORC1 signalling, AMPK multiply phosphorylates and activates TSC2 when cellular energy is low. In addition, AMPK also directly phosphorylates the essential mTORC1 component Raptor on two serine residues. This phosphorylation induces 14-3-3 binding to Raptor and is required for mTORC1 inhibition by energy deprivation.

In accordance with the present invention it can be shown that AMPK does not only respond to energy deprivation but is also strongly activated by insulin, and is further induced in Raptor deficient cells. These findings are in line with others known in the art, however the underlying signalling events have been so far only poorly investigated. In order to define the intersection via which AMPK is activated by the insulin network, a data-driven dynamic AMPK-mTOR network model can be generated and a combined modelling-experimental approach can be used. Thereby, it is possible to compare simulations for different model structures to observed AMPK dynamics. Hypotheses ranking suggested that the most probable intersection between insulin and AMPK was IRS, and effects of canonical IRS downstream cues on AMPK are mediated via the NFL. These predictions experimentally can be tested and verified in multiple setups. In the following, a novel connection within the insulin-mTOR-AMPK network is described: it is concluded that AMPK is positively regulated by IRS, and can be inhibited via the NFL.

The development of a dynamic mTOR network model covering insulin and amino acids (aa) signalling as mTORC1 regulators is described above. AMPK is another important mTOR regulator that suppresses mTORC1 activity in response to energy deprivation and in the following this regulation is added to the model and the method according to the invention. Therefore, preferably the following novel connection is introduced into the existing network structure referred to above: AMPK phosphorylation at T172 allows AMPK to phosphorylate the species TSC1_TSC2 at S1387 which leads to TSC1TSC2 activation and subsequent inhibition of mTORC1. Conversely, the phosphorylation of the species TSC1_TSC2 at T1462 by Akt_pT308 inhibits the TSC1_TSC2 complex, activating mTORC1. Finally, the species Akt_p S473, PRAS40_p T246 and PRAS40_p S183 were defined as supplementary readouts for mTORC2, Akt, and mTORC1, respectively.

In order to calibrate the AMPK module and connect it to the mTOR model and method referred to above, AMPK time courses under the same conditions which can be used for calibration of the dynamic mTOR network model can be acquired. These were starvation for serum and aa followed by network induction by insulin and aa. AMPK is described to be induced in Raptor deficient cells. Therefore, it should be also investigated AMPK activity upon gradual knock down in an inducible Raptor knock down (shRaptor) HeLa cell line. The knock down can be induced by doxycycline treatment for 3, 2 or 0 days, cells can be starved for 16 hours, and activation with insulin/aa can be followed from 3 min up to 100 min post induction (p.i.). As previously described, the direct mTORC1 substrate p70S6K-pT389 can be activated from 20 min on and displayed reduced phosphorylation upon Raptor knock down induction. AMPK activity can be monitored by detecting phosphorylation at T172, reflecting active AMPK. Although AMPK is known to be induced by energy depletion, it could be shown for surprise that e.g. AMPK-pT172 is also strongly induced by insulin/aa, already 3 min p.i. Overall AMPK-pT172 induction decreased with time. As expected, AMPK-pT172 can be more strongly induced upon Raptor knock down, and this can be e.g. observable from 20 min p.i. onwards. Upon activation, AMPK phosphorylates TSC2 at S1387, leading to TSC2 activation and subsequent inhibition of mTORC1. Therefore, the use of TSC2S1387 as second AMPK readout can be preferred, to confirm the findings on AMPK activation. Indeed, TSC2-pS1387 followed AMPK-pT172 with some delay, starting e.g. 20 min p.i. and can be induced by insulin/aa, and in Raptor knock down cells. All signal intensities can be quantified, and descriptive statistics can be computed over three replicates. The experimental mean time courses can be used to calibrate the model parameters.

Although it has been described previously that AMPK can be induced by IGF-1, insulin induction of AMPK is described here for the first time, and this signalling connection has to date not been explored. Therefore, we systematically investigated possible AMPK-activators along the insulin-mTORC1 axis. mTORC1 is induced up to at 30 45 min p.i. at the maximum. Of course, also other values of mTORC1 can be possible to reach the desired effect. As AMPK induction by insulin peaked already as early as 3 min p.i., and/or earlier and/or later, and AMPK can be induced by Raptor knockdown (for example mTORC1 inhibition), as candidate AMPK activators the species upstream of mTORC1 can for example be selected:

1) Insulin, where insulin is considered as constant and direct input to AMPK;
2) IR_beta_pY1146, reflecting IR activation;
3) IRS1_p, reflecting IRS1 activation by insulin receptor;
4) mTORC2_pS2481, reflecting mTORC2 activation by insulin/aa;
5) Akt_pT308, reflecting Akt activation downstream of PI3K; and/oder
6) TSC1_TSC2_pT1462, reflecting TSC1TSC2 deactivation by Akt.

A graphical representation of our insulin-mTOR-AMPK model depicting our six alternative hypotheses of AMPK activation is provided in FIG. 29B.

A specific model was instantiated for each hypothesis and calibrated using preferably the same data sets and for example using the Matlab Toolbox PottersWheel. Before calibrating the models, structural identifiability analysis can in particular be performed using the software GenSSI or other software. Said software can e.g. calculated the symbolic solution of the problem computing Lie derivatives for each hypothesis confirming structural global identifiability for all six models. For example, for the IRS1-induced AMPK model, structural identifiability analysis can be reported, showing that all the parameters can be structurally identified.

To calibrate the models, experimental time courses upon insulin/aa induction for nine readouts (IR_beta_pY1146, IRS1_pS636, Akt_pT308, Akt_pS473, MTORC1_pS2448, mTORC2_pS2481, p70S6K_pT389, PRAS40_pT246, PRAS40_pS183; data set 1) in wild type cells along the insulin-mTOR signalling axis can in particular be used in combination with time courses under gradual mTORC1 inhibition (Raptor knock down; data set 2), as in particular measured previously. Furthermore, in order to calibrate the species AMPK_pT172 and TSC1_TSC2_pS1387, for example the five time points (0, 3, 20, 45, and 100 min. p.i.;) without knock down induction, for example corresponding to wild type, were added as an additional data set (data set 3).

Parameter estimation can preferably be executed for each model independently over multiple data sets in order to reduce the bias of the solution and therefore overfitting. However, the addition of data sets used to calibrate a model can under certain circumstances lead to a serious increment of variance, particularly due to the increase in intrinsic noise in experimental data, which does not permit to estimate the model correctly.

The second data set can be characterised by three different levels of Raptor knock down, obtained by doxycycline treatment for e.g. 1, 2 or 3 days respectively (subsets 1-3). A satisfactory bias-variance trade off can in particular be found by combinatorially and singularly testing these three subsets and eventually selecting only the subset of Raptor knock down induced by doxycycline treatment for in particular 3 days (subset 3). Subset 3 was selected as it represented the strongest signal reduction and consequently novel information with respect to wild type time courses (data set 1) for calibrating the model and the method according to the invention. Moreover, the readouts in the data sets (data set 1, data set 2-subset 3, data set 3) can be scaled in order to have species time courses of similar intensity. This can preferably equally distributes the cost of the solution over the simulated time courses approximating the data avoiding an implicit preference ranking of calibration.

For calibrating the models, the kinetic rate constant parameters can be in particular estimated only, whereas the species protein concentrations can preferably be determined from the immuno blot time courses by e.g. selecting the corresponding readout maximum intensity plus two standard deviations measured at that time point. The addition of two standard deviations to the maximum signal peak can in particular guarantee to avoid species protein saturation conditions. The kinetic rate constants regulating PI3K-variant dynamics can preferably be fixed a priori assuming a time course similar to the insulin receptor. In fact, no experimental data is available for this PI3K insensitive to the negative feedback loop and it is more likely that it follows the IR-beta receptor than other curves. Furthermore, fixing these parameters can in particular lead to a full structural identifiability of the model.

A posterior identifiability analysis can preferably be performed using Mean Optimal Transformation Approach (MOTA) plugin after selecting the 50% of the best fits. This analysis can in particular reveal that high parameter correlations had coefficient of variation (CV) lower than 0.05 for all models and methods according to the invention except for the IR-beta-induced AMPK model (hypothesis 2). For this model according to the invention, MOTA analysis can in particular highlight high correlation and CV for the pair of parameters regulating AMPK dynamics. Model identifiability can preferably be obtained after fixing one of the two parameters and recalibrating the remaining one in a second round of calibration. In combination with the previous analysis, it is also possible to check parameter nonidentifiability by directly analysing the estimated percentage of standard deviations of the parameters, computed over the 50% best fits, and in particular considering non-identifiable the parameters with standard deviation percentage higher than a threshold of 5%. Table 5 presents examples of estimated parameters values with mean, standard deviations and CV for the IRS1-induced AMPK model showing parameter identifiability.

Once the parameter estimation could be achieved, the simulated time courses for the readouts AMPK_pT172 and TSC1_TSC2_pS1387 of each model can in particular be compared with the corresponding experimental time courses. Surprisingly, it can be observed that the readouts AMPK_pT172 and TSC1_TSC2_pS1387 for the IRS1-induced AMPK model (hypothesis 2) fitted the data with high accuracy, whereas the goodness-of-fit decreased for species downstream of IRS1 (Akt and TSC1-TSC2; hypotheses 5 and 6) and upstream of IRS1 (Insulin, IR-beta; hypotheses 1 and 2), as indicated by the measure $\chi 2$.

Furthermore, the two readouts might fit worse for the mTORC2-induced AMPK model (hypothesis 4). At this point, it has to be questioned whether these local differences could lead to a possible ranking of the overall models. In order to achieve this, several additional likelihood-based statistical criteria, such as Akaike Information Criterion (AIC, AICc) and Bayesian Information Criterionv (BIC), can in particular be used besides the total $\chi 2$, to estimate the goodness-of-fit calculated over the entire models. These estimations allow a person skilled in the art to establish a ranking of the hypotheses in according to the goodness-of-fit (Table 2). All these measures can be consistent between them and with the above observations in selecting the IRS1-induced AMPK model (hypothesis 2) as the most probable model and method according to the invention.

In summary, hypotheses ranking suggested IRS (hypothesis 3) as the most probable inducers of AMPK in response to insulin. This in turn suggested that downstream cues of IRS1 could affect AMPK via the NFL, which would be in line with the observed AMPK induction in mTORC1 deficient cells.

Hypothesis 3 predicts that IRS will be preferably required for AMPK induction by insulin. First it can therefore be tested whether IRS hyperactivation alone would result in increased AMPK-T172 phosphorylation. To achieve this it can be advantageous to overexpress wild type IRS-1 (Myc-IRS-1 WT) or mutagenised IRS-1 variants, resembling either IRS-1 constitutively phosphorylated by S6K (Myc-IRS-1 S636/639 D) or constitutively unphosphorylated on the same sites (Myc-IRS-1 S636/639 A). The variants can in particular be NFL insensitive and whereas the D variant can preferably be less active, the A variant can in particular be hyperactive. The constructs can preferably be overexpressed in HeLa cells. As expected MycIRS1 WT and MycIRS1 S636/639 A strongly induced Akt-pT308 and mTORC1 activity toward p70S6KT389, whereas MycIRS1 S636/639 D did not. Importantly, Myc-IRS-1 WT moderately and MycIRS1 S636/639 A strongly induced AMPK-pT172, whereas AMPK-pT172 was refractory to MycIRS1 S636/639 D overexpression. This finding of the present invention is in line with hypothesis 3, which suggests the requirement of active IRS for AMPK induction by insulin. To further confirm our finding we also analysed the AMPK target site TSC2-S1387 upon overexpression of MycIRS1 WT. TSC2pS1387 was strongly induced, again suggesting positive regulation of AMPK by IRS-1.

IRS-1 hyperactivation can in particular strongly induce PI3K activity, and there is in particular no need to differentiate in hypothesis 3 between IRS and PI3K activity. Therefore, it might be advantageously to test next whether PI3K also positively affects AMPK. Therefore, for example PI3K can be inhibited with Wortmannin prior to insulin/aa induction: as expected, Wortmannin inhibited Akt-pT308, downstream of PI3K. In contrast, Wortmannin induced AMPKT172 phosphorylation. To confirm this finding in a complementary setup, it can be in particular advantageously to overexpress the PI3K antagonist Phosphatase and tensin homolog (PTEN): whereas PI3K generates phosphatidylinositol (3,4,5)-trisphosphate (PIP3) leading to induction of PDK1, Akt and their downstream targets, PTEN dephosphorylates PIP3 thereby counteracting PI3K activity. As expected, PTEN overexpression can in particular strongly inhibit mTORC1 activity toward p70S6KT389 (FIG. 4D). In agreement with the findings of the present invention for Wortmannin, also increased PTEN levels activated AMPK as evidenced by AMPK-pT172 induction. Therefore it can in particular be concluded that AMPK is induced by IRS, but inhibited by PI3K. The induction of AMPK in response to PI3K inhibition is in line with our own and previous findings on AMPK induction in mTORC1 deficient cells, and might be mediated via the NFL. In other words, if IRS is required for AMPK induction, inhibition of the NFL (targeting IRS) should preferably induce AMPK.

If this reasoning and hypothesis 3 hold true, activation of Akt and subsequent hyperactivation of the NFL should inhibit AMPK. This prediction can therefore be in particular be tested by overexpressing a myristoylated Akt version (HAmyrAkt) which is constitutively localised to the plasma membrane and does in particular not require IRS or PI3K for its activation. As expected for Akt hyperactivation, HAmyrAkt expression strongly induced the Akt target site TSC2pT1462. TSC2T1462 phosphorylation leads to inhibition of the TSC1TSC2 complex and hyperactivates mTORC1. Also mTORC1 activity toward p70-S6K-T389 can preferably be expectedly strongly induced by HAmyrAkt overexpression, and p70 S6K activation induces the NFL. In contrast, AMPK-pT172 can preferable be inhibited by HAmyrAkt, and the same could be confirmed for the AMPK target site TSC2-S1387, required for TSC1TSC2 activation. This result is in agreement with our model 3, predicting a negative effect of Akt on AMPK, via the NFL and IRS. These data also directly exclude, which are on ranks 2 and 3 in our hypotheses ranking (Table S6).

In summary, the present invention found four independent experimental setups to test the predictions of model 3, which was ranked 1 in the presented hypothesis ranking. All experiments provide strong evidence for model 3, where IRS or PI3K induce AMPK, and exclude the other hypotheses where other insulin downstream cues mediate AMPK activation: it can be shown that IRS-1 strongly induces AMPK, whereas the PI3K-Akt-mTORC1 signalling axis suppresses AMPK. This is in line with the NFL (downstream of PI3K, Akt, and mTORC1) suppressing AMPK, which is predicted by model 3.

What are the biological implications of the findings of the present invention? It is shown that in HeLa cells AMPK is induced by insulin/aa. However, HeLa cells are particular in the sense that they do not express the AMPK upstream kinase LKB1. Therefore, it was important to address whether the here observed insulin/aa induction of AMPK is a general feature of AMPK signalling, or whether it remains restricted to LKB1 deficient cells. Hence, it was tested the effect of insulin/aa induction on AMPK activity in C2C12 myocytes, which are LKB1 positive. It could be observed AMPK induction by insulin/aa also in C2C12 cells, underlining the general importance of our findings.

In the present invention insulin/aa induction of AMPK could be observed. Although IGF1 induction has been reported before, this is the first observation of AMPK induction by insulin and it is the first approach which systematically explores the underlying signalling interconnections within the insulin-mTOR network. To this purpose we systematically postulated molecules along the insulin-mTORC1 signalling axis as putative AMPK activators. Furthermore, it can be presumed that the putative AMPK inducer would be upstream of mTORC1, firstly because AMPK was induced earlier (e.g. 3 min. p.i.) than mTORC1 and its downstream targets, and second because Raptor inhibition induced AMPK. Applying a hypothesis ranking approach, we successfully used a dynamic insulin-mTOR-AMPK model for hypothesis prioritisation.

In accordance with the hypothesis that best fits the data (hypothesis 3), it could be experimentally confirmed that IRS activates AMPK. In contrast, all tested IRS downstream cues within the PI3K-mTORC1 axis (PI3K, Akt, mTORC1) inhibited AMPK. This is in line with the prioritised model where the NFL—downstream of mTORC1 and S6K—inactivates IRS for PI3K activation as well as for AMPK induction. AMPK is induced by wild type IRS and a mutagenised IRS version which cannot be targeted by the NFL, whereas AMPK is refractory to expression of an IRS version which resembles constitutively NFL targeted IRS. Also this finding strongly suggests that indeed the NFL might inactivate IRS not only for PI3K but also for AMPK induction.

From a modelling point of view, a comprehensive mTOR network can be studied statically and parts of the mTOR network can be modelled dynamically. The network presented in this part of the present invention is the most extensive mTOR-AMPK model. Six models were defined and calibrated using experimental data. The models shared the main network structure, but differed for the AMPK activation mechanism. After repeating cycles of parameter calibration and identifiability for each model, likelihood-based statistical measures were used to estimate a model ranking, based on the goodness-of-fit between each model and the experimental data.

In the present invention a transient AMPK induction by insulin and active IRS as AMPK inducer could be observed. On the other hand, AMPK inhibits IRS by phosphorylation of IRS-1-S794. One of the questions is if this mechanism could be connected to the here observed AMPK induction by IRS? It is conceivable that two antagonistic mechanisms are mediated by IRS: When IRS is active, it will activate AMPK—and at the same time AMPK could directly via IRS contribute to inhibition of insulin signalling. This putative mechanism clearly deserves further mechanistic investigation.

It is important to note that HeLa cells, which can in particular be used for the present invention, do not express LKB1. This suggests that AMPK induction by insulin and IRS is LKB1 independent, at least in HeLa cells. Which other kinase could be responsible? AMPK phosphorylation in HeLa (and other) cells is mediated by the kinase ATM.

Interestingly, AMPK induction by ATM occurs in a tyrosine kinase dependent, but PI3K independent manner. This is consistent with the finding of the present invention that IRS, but not PI3K induces AMPK. Other possible candidates for LKB1 independent AMPK induction are e.g. the kinases CAMKK, TAK1, or IRE1.

What is the relevance of the here reported mechanism in LKB1 expressing cells? Firstly, Suzuki et al. have reported IGF1 inducibility of AMPK not only in LKB1 deficient HeLa cells, but also for LKB1 expressing PANC1 cells. Also the data of the present invention confirm inducibility of AMPK by insulin/aa in LKB1 expressing C2C12 myocytes, suggesting that this mechanism may be present in a larger number of cell types. Furthermore, at least two other studies have reported that AMPK is induced by mTORC1 or S6K ablation in mice. This suggests that IRS dependent AMPK induction might become particularly prominent under conditions when the NFL is inhibited. Hence, IRS dependent AMPK induction may exert some of the beneficial effects which have been observed for mTOR-inhibitor treatment of metabolic and tumour diseases.

What could be the biological function of a transient AMPK induction by insulin? Firstly, AMPK inhibits mTORC1 signalling in particular at two levels, TSC1-TSC2 and mTORC1 itself. Therefore, this transient AMPK induction in response to insulin might—in addition to the NFL—serve as a second mechanism to prevent mTORC1 hyperactivation. As an additional benefit AMPK activation might serve as a protective mechanism to cellular stress under transiently increased metabolic rates in response to insulin.

In conclusion, we present here a, in particular the most comprehensive, data-driven dynamic mTOR-AMPK network model. The combined modelling-experimental approach according to the present invention revealed IRS as mediator of AMPK induction in response to insulin and strongly suggests an involvement of the mTORC1-dependent negative feedback loop in AMPK regulation among others. The impact of this novel signalling interconnection for AMPK and mTOR biology deserves further exploration. The findings of the present invention could be highly relevant to the biomedical field since they can have important implications for administration of drugs targeting mTOR and AMPK, which are commonly used in tumour and metabolic disease treatments.

Afterwards, details to the materials and models are described with respect to the insulin-TOR-AMPK model referred to above.

Cell Lines and Lentiviral Transduction

Experiments can preferably be performed in HeLa α Kyoto cells and C2C12 myocytes. For inducible knock down of Raptor, HeLa cells can e.g. be transduced with lentivirus encoding the tetracycline-sensitive tTR-KRAB repressor and a DsRed reporter. Cells can for example be subsequently transfected with lentivirus encoding the Raptor specific shRNA, and a GFP reporter, (pLVTH vector), both under the control of tTR-KRAB.

Overexpression of IRS, PTEN and myristoylated Akt variants

N-terminally and HA tagged pSG5L HA PTEN wt (#10750), N-terminally myristoylated and HA tagged pLNCX.myr.HA.Akt1 (#9005), and N-terminally myristoylated and HA tagged kinase dead pLNCX.myr.HA.Akt1 K179M (#9006) can for example be ordered from Addgene. IRS1 constructs were a kind gift from A. Tzatsos. Transfection can in particular be performed with 6 µg per 6 cm dish using JetPEI reagent according to the manufacturer's instructions. Cells can for example be harvested 24 hours after transfection.

Antibodies and Reagents

The Anti-GAPDH monoclonal antibody can in particular be purchased from Abcam, Cambridge, UK. The anti-HA antibody can for example be purchased from Roche. Horseradish peroxidase conjugated goat anti-mouse and goat anti-rabbit IgG can in particular be purchased from Pierce Biotechnology (Thermo Scientific, Rockford, Ill. USA). All other antibodies can for example be purchased from Cell Signalling Technology, Danvers, Mass., USA. Doxycycline for knock down induction can in particular be purchased from Calbiochem, Merck, Darmstadt, Germany. Wortmannin can in particular be purchased from Sigma Aldrich, St. Louis, Mo., USA. Chemicals can for example be supplied by Carl Roth, Karlsruhe, Germany if not indicated elsewise.

Analysis of Cell Lysates

Where indicated HeLa cells can in particular be starved for serum and aa by exchanging standard growth medium for HBSS over night to inhibit mTOR pathway activity. After for example 16 hours starvation mTOR signalling can in particular be restimulated for 30 min with DMEM containing aa and supplemented with 100 nM insulin (Sigma Aldrich, St. Louis, Mo., USA).

Gradual knock down of Raptor can in particular be established by induction with 5 µg/ml doxycycline (Calbiochem, Merck, Darmstadt, Germany) for 0, 1, 2, or 3 days. Wortmannin treatment can in particular be performed 30 min prior to stimulation with DMEM, 100 nM insulin in the continuous presence of Wortmannin. Cells can for example be washed once with PBS and lysed with TNE lysis buffer (50 mM Tris HCL pH8.0, 150 mM NaCl, 1% v/v TritonX-100 (Calbiochem, Merck, Darmstadt, Germany), Complete (Roche, Mannheim, Germany), Phosphatase Inhibitor Cocktail 2, Phosphatase Inhibitor Cocktail 3 (both Sigma Aldrich, St. Louis, Mo., USA)). Protein concentrations can in particular be measured (Protein Assay Dye Reagent Concentrate, Bio-Rad, Hercules, Calif., USA) according to manufacturer's protocol. Concentrations were adjusted with lysis buffer. Lysates can in particular be diluted in sample buffer (5×: 6 ml glycerol, 0.6 ml beta-mercaptoethanol, 1.0 g SDS, 3.75 ml 1 M Tris pH 6.8, 2 mg bromophenol blue, 2 ml H2O). Whole cell lysates can for example be analyzed using SDS-PAGE gels. Proteins can in particular be transferred to PVDF membranes (Millipore, Billerica, Mass., USA), blocked with 5% BSA in TBST (8 g NaCl, 0.2 g KCl, 8 g Tris, pH 7.4, 0.1% Tween 20) for a minimum of 30 min and incubated with the primary antibody in 5% BSA in TBST over night, shaking at 4° C. Blots can for example be washed 3× with TBST, incubated with secondary antibodies coupled to HRP and were washed 3× with TBST before detection.

Modelling

The illustrated graphical model in SBGN graphical notation can for example be designed using CellDesigner 4.2. The Matlab Toolbox PottersWheel can in particular be used for designing and calibrating the models. The parameters for each of the models can for example be estimated by 1000 fits with parameter disturbance noise of 0.4 using the best fit as starting value. For each fit a maximum of 250 iterations with $\chi^2$ and parameters tolerances of 1e-07 can in particular be run using the optimisation algorithm TrustRegion. To reduce the computation time, cvodes integrator can in particular be selected and configured with the following parameters: maximum number of steps=1500, relative tolerance=1e-06, absolute tolerance=1e-08.

The reactions representing the dynamics of the models can in preferably be described by mass action laws. Only the kinetic rate constants can in particular be estimated and the interval [1e-06, 1e+04] can in preferably be selected as constraint for each parameter. The protein initial concentrations can for example be directly determined from our experimental data and scaled to distribute the fitting quality over the model. Experimental error bars can for example indicate standard error of the mean (SEM). The dynamics for the species PI3K-variant can in particular be assumed by reproducing the dynamics of the insulin receptor, whereas its initial concentration was the same of IRS1 species.

Structural identifiability can in particular be calculated a priori with GenSSI. The model in Potterswheel format can in particular be exported in SBML and converted to Octave format for example using The System Biology Format Converter (SBFC) (available from sourseforge.net). Then the model in Octave format can for example be adapted for the software GenSSI. Symbolic solutions for each models were computed setting 10 or lower or higher as maximum number of iterations.

After executing each sequence fits, parameters can in particular be considered non-identifiable when their coefficients of variance (CV), measured in the best 50% fits of the calibration sequence, were for example higher than 5%. In combination to this preliminary analysis, the PottersWheel plugin MOTA can in particular be used to confirm the parameter non-identifiability and to assess the relations between the target parameter and the others.

3D Sensitivity analysis can in particular be performed using PottersWheel and provided in Supplementary Fig. S2. We also used PottersWheel to export the models as SBML Level 2 Version 4.

Statistics

The goodness-of-fit statistical measures $\chi^2$, AIC, AICc and BIC were used in order to rank the hypotheses. All these measures were directly computed using PottersWheel Toolbox.

The statistical and programming language R v. 2.13.1 can for example be selected for the graphic representation of the identifiability matrix computed with MOTA.

BRIEF DESCRIPTION OF THE DRAWINGS

Additional features, details and advantages of the invention are given in the accompanying claims and in the technical drawings and subsequent description, wherein FIG. 1 to are related to a general further description of the invention and figure is related to one embodiment of the invention.

The drawings show:

FIGS. 26A-26B: Simulation and perturbations for hypothesis No. 4;

FIGS. 30A-30B: Identifiability analysis for IRS1-induced AMPK model (hypothesis 3);

FIG. 33 FIGS. 33-33B: New model structure: IRS is required for AMPK induction by insulin;

FIGS. 34A-34C: Identifiability and parameter estimation for the IR-beta-induced AMPK model (hypothesis No. 6);

FIGS. 35A-35B: Sensitivity analysis for the IRS1-induced AMPK model (hypothesis No. 7);

FIG. 36: Additional simulated versus experimental time courses for IRS1-induced AMPK model (hypothesis No. 7);

Table S1: Ordinary Differential Equations (ODES) of the general model and the three hypotheses of mTORC2 activation;

Table S2: Parameter values of the general model;

Table S3: Parameter values of the three hypotheses;

Table S4: Summary of model goodness-of-fit;

Table S5: Parameter table for the IRS1-induced AMPK model (hypothesis 3); and

Table S6: Statistical ranking of the models.

DESCRIPTION OF SPECIFIC EMBODIMENTS OF THE INVENTION

FIGS. 1A-1G show a setup of a dynamic insulin-stimulated mTOR network model and confirmation of mTOR-pS2481 as a specific mTORC2 readout.

Figure 1:
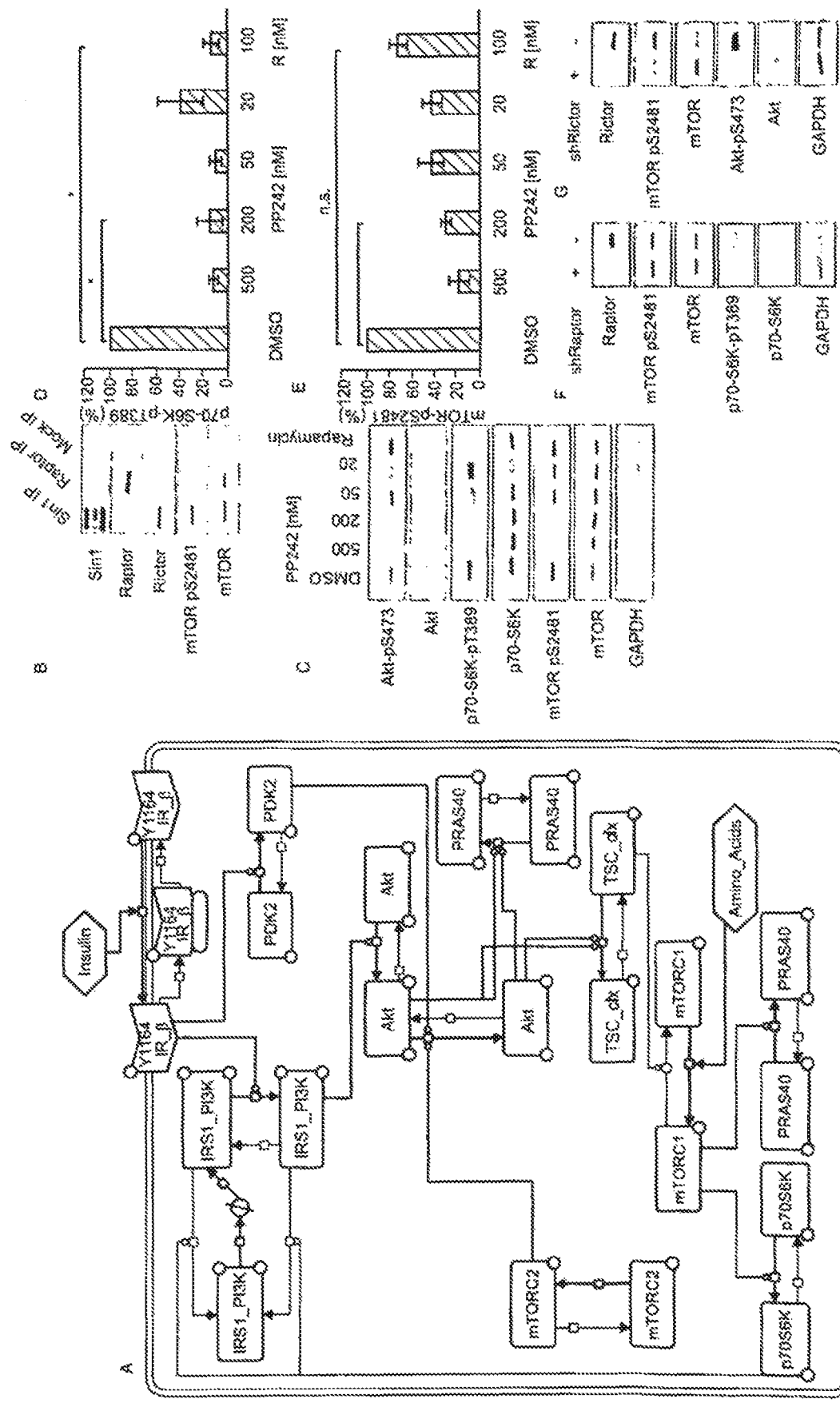
FIGS. 1A-1G: a schematic setup of a dynamic insulin-stimulated mTOR network model and confirmation of mTOR-pS2481 as a specific mTORC2 readout.

FIG. 1A shows a reduced graphical model of the mTOR network activated by aa/insulin (see FIG. 11 for the extended graphical model).

FIG. 1B shows a coimmunoprecipitation of mTOR-pS2481 with Sin1 (a component of mTORC2) or Raptor (a component of mTORC1); Mock IP=control IP with a non-specific antibody. Data are representative of 3 experiments.

FIG. 1C shows an effect of PP242 or Rapamycin on the indicated phosphorylated proteins. Data are representative of 3 experiments.

FIGS. 1D and 1E shows a quantitation of 3 experiments like the one shown in FIG. 1C for mTORC1 readout p70-S6K-pT389 (FIG. 1D) and mTORC2 readout mTOR-pS2481 (FIG. 1E). R=Rapamycin. * $P<0.05$, n.s. not significant. (FIG. 1D) 200 nM PP242 (mTOR specific standard concentration, (6)) compared to DMSO-treated control and Rapamycin compared to DMSO control were significant. (FIG. 1E) 200 nM PP242 compared to DMSO-treated control was significant. 100 nM Rapamycin compared to DMSO control was not significant.

FIG. 1F shows an effect of Raptor knockdown on mTORpS2481. Data are representative of 3 experiments.

FIG. 1G shows an effect of Rictor knockdown on mTORpS2481. Data are representative of 3 experiments.

Figure 2:
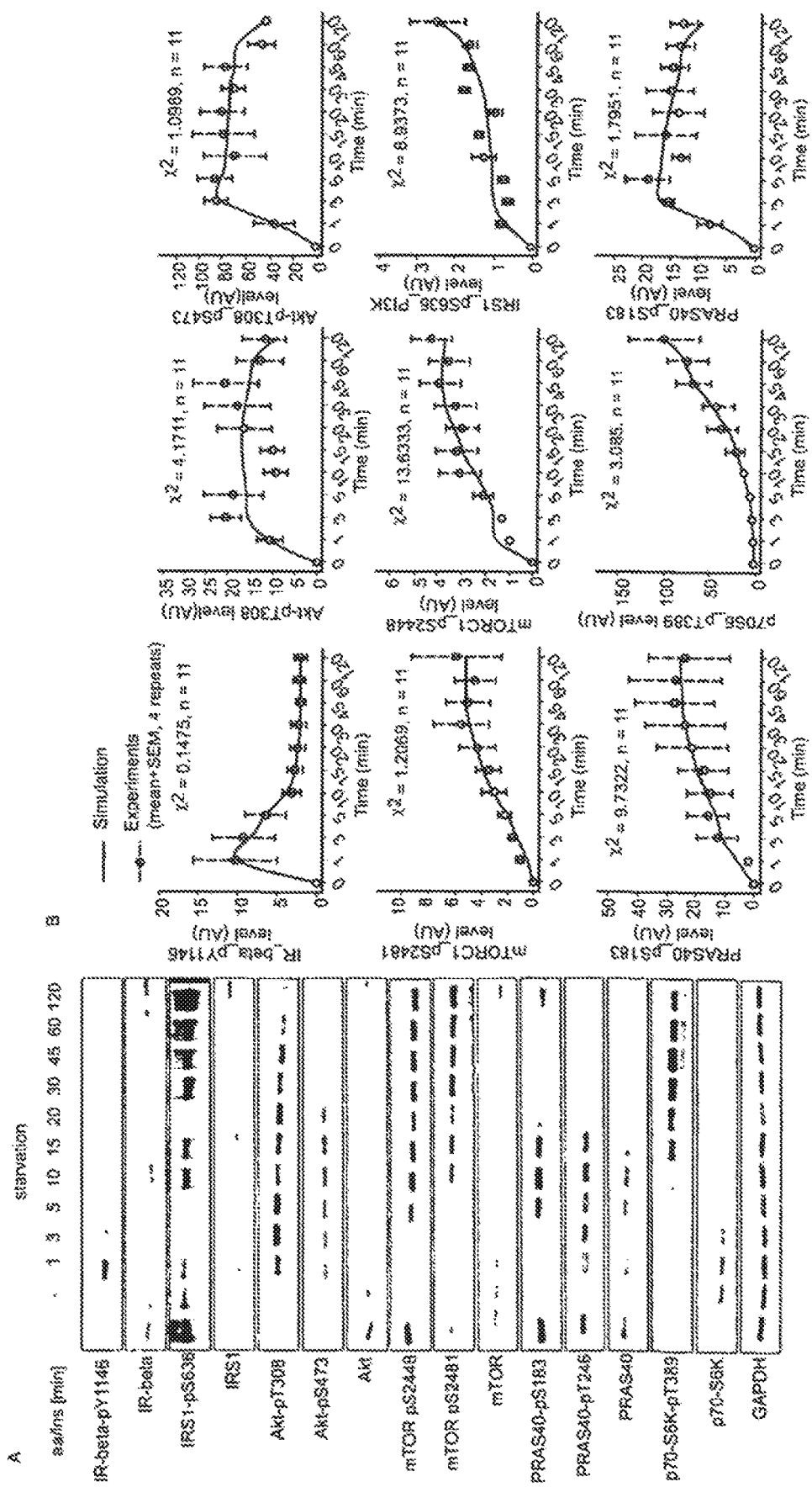
FIGS. 2A-2B: a schematic setup of a dynamic insulin/mTOR network model.

FIGS. 2A-2B show a setup of a dynamic insulin/mTOR network model.

FIG. 2A shows a dynamic quantitative time course acquisition. mTOR pathway activation was followed over time by measuring phosphorylation dynamics of central network components. A representative experiment is shown; signal intensities were quantified and descriptive statistics were computed over four replicates.

FIG. 2B shows a comparison between the simulated time courses of the general model (solid lines) and the experimental time courses (points, dotted error bars) within [0, 120] min. For each curve, the chi-square computed over n time points, is reported as goodness-of-fit measure.

FIGS. 3A-3D show a validation of a dynamic response of p70-S6K-pT389 to gradual Raptor inhibition.

Figure 3:
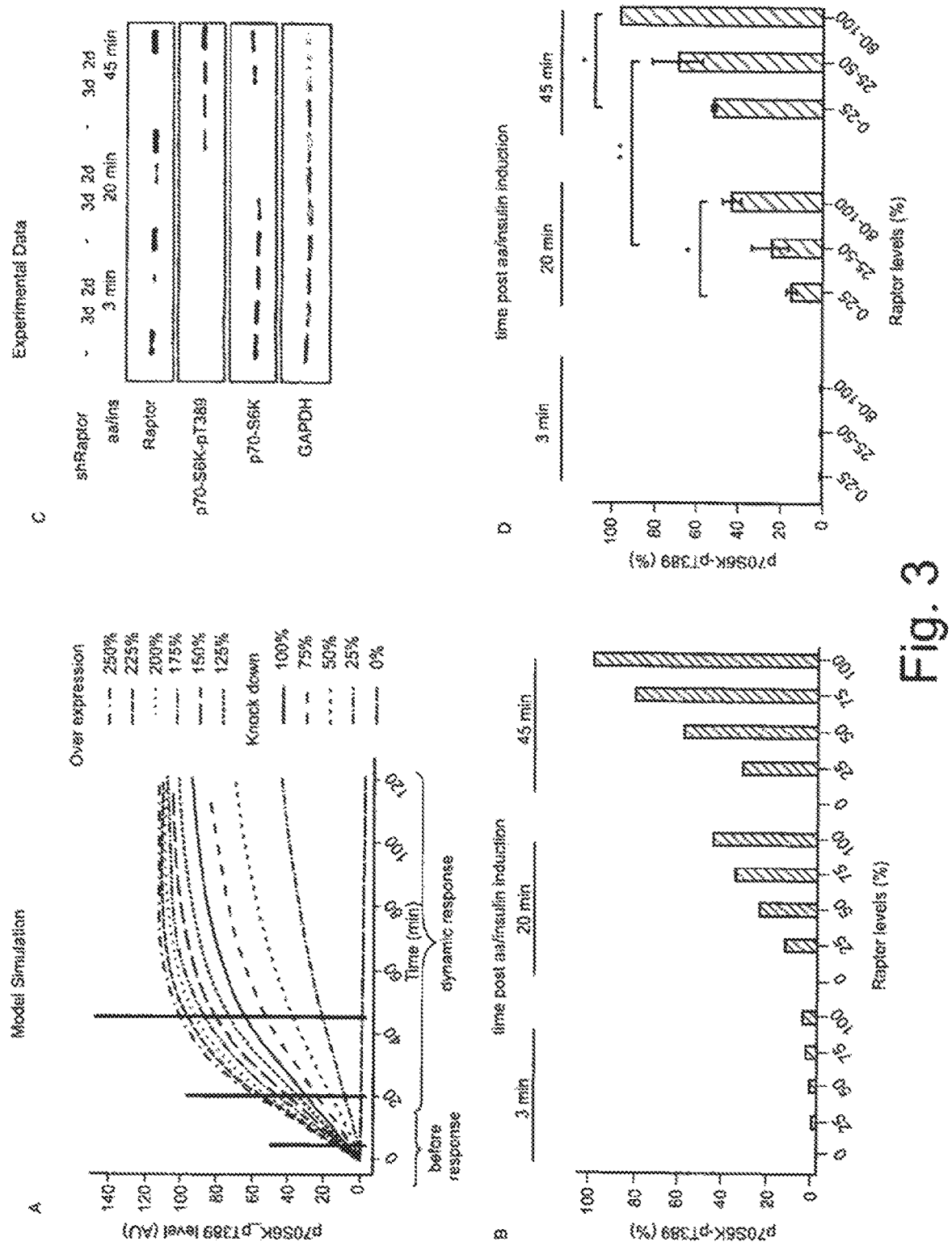
FIGS. 3A-3D: Validation: dynamic response of p70-S6K-pT389 to gradual Raptor inhibition.

FIG. 3A shows a model predictions for p70-S6K-pT389 dynamics in response to a perturbation of mTORC1. The curves show the simulated response to gradual mTORC1 inhibition starting at 5-10 minutes after induction with aa/insulin. The model was simulated with both mTORC1 overexpression and knockdown conditions. Time points for experimental validation are indicated by green lines.

FIG. 3B shows a simulated and quantified relative amounts of p70-S6 KpT389 under conditions of mTORC1 reduction (0, 25, 50, 75, 100%) at selected time points after induction with aa/insulin.

FIG. 3C shows an experimental validation of the effect of gradual Raptor knockdown (shRaptor) on p70-S6K phosphorylation in starved cells induced with aa/ins for the indicated times. Data are representative of 3 experiments. d=days.

FIG. 3D shows an experimentally determined and quantified p70-S6K-pT389 amounts at the indicated times after induction with aa/insulin in cells in which Raptor was knocked down. Data are the average and SEM of 3 experiments. * $P<0.05$, ** $P<0.01$; low Raptor levels compared to high Raptor levels after 20 min and 45 min induction, 20 min compared to 45 min induction. Differences in p70-S6K-pT389 were significant.

Figure 4B:
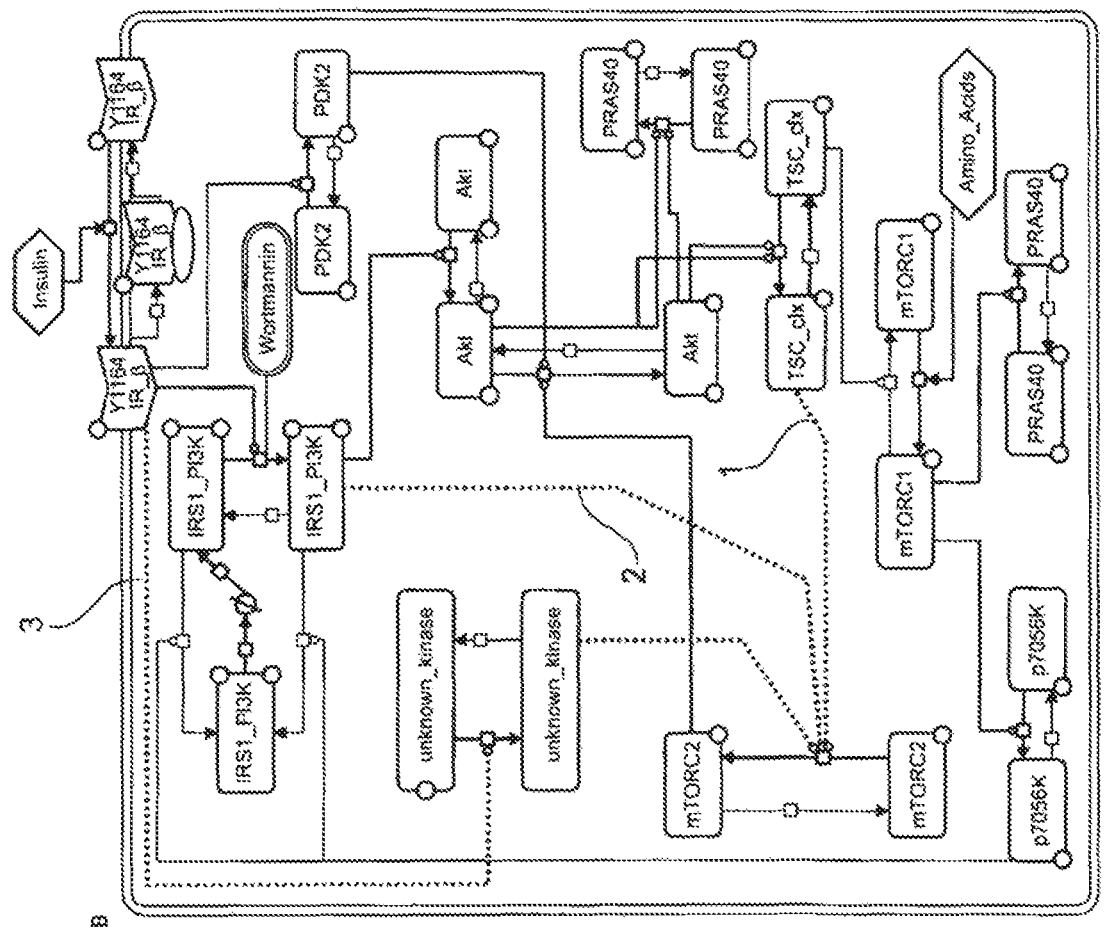
FIGS. 4A-4C: Three hypotheses for mTORC2 regulation by insulin.
Figure 4A:
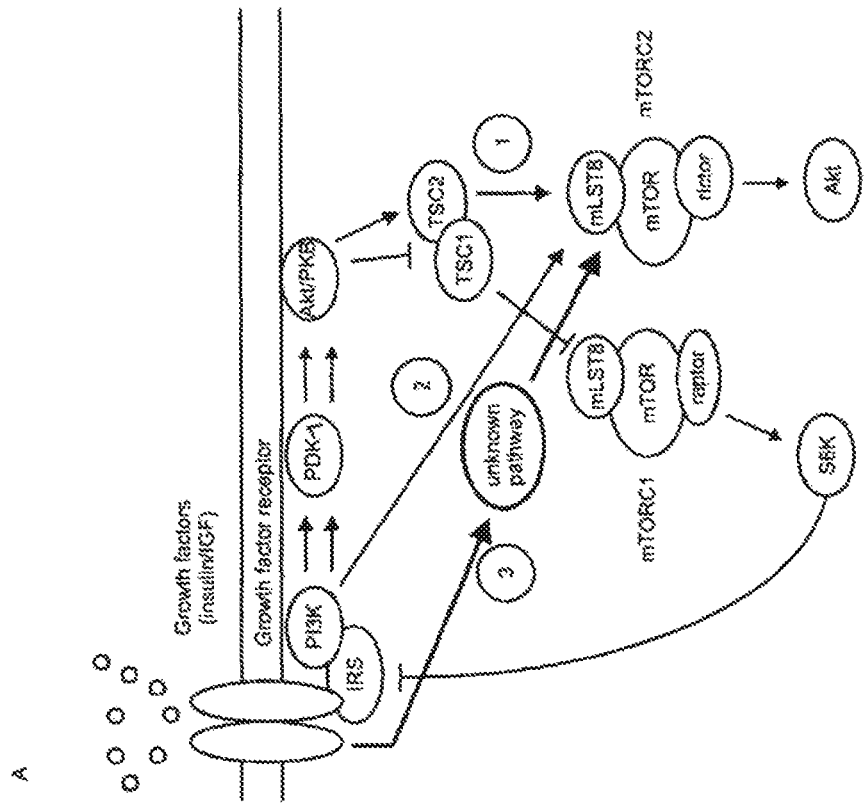
Figure 4C:
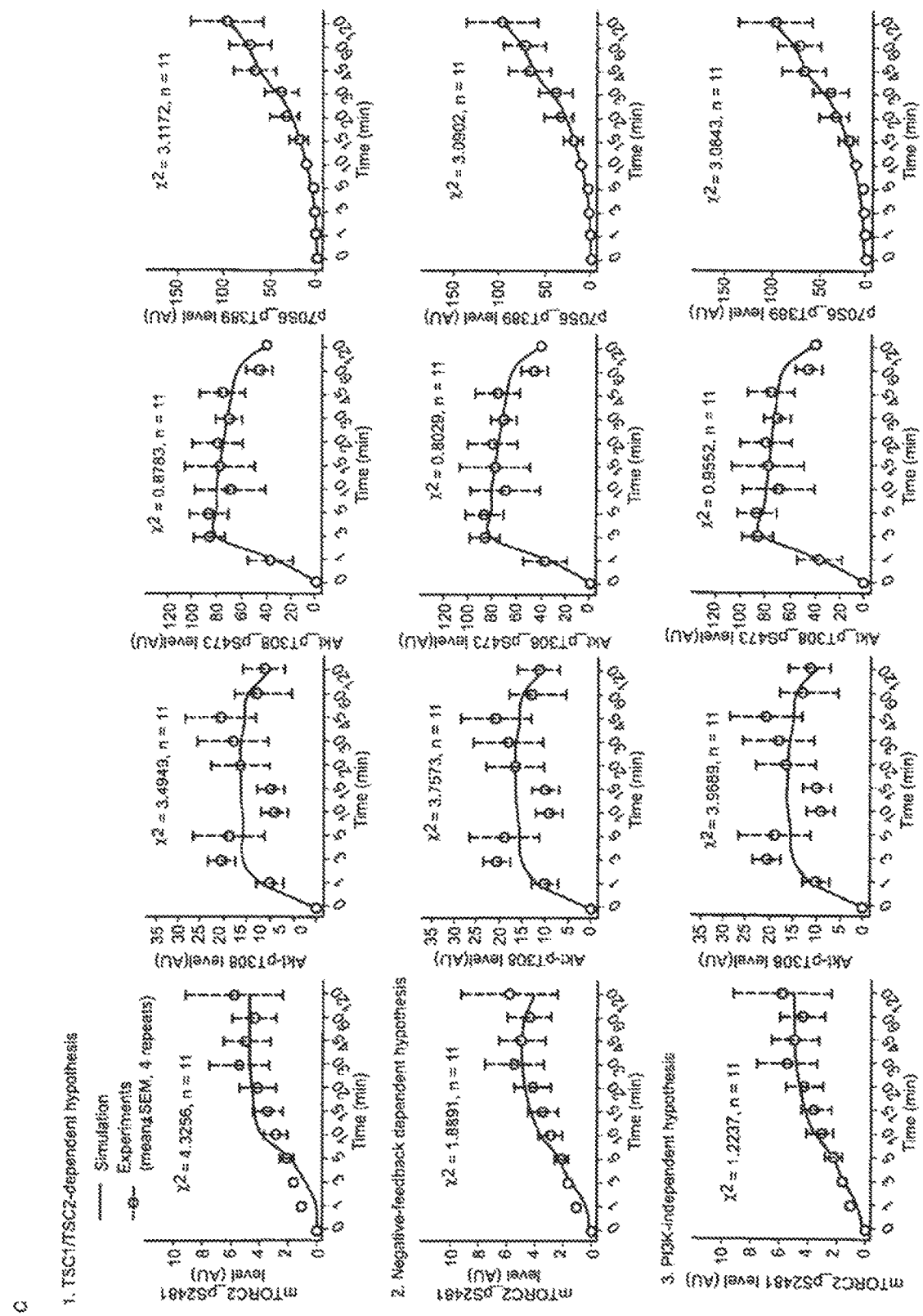

FIGS. 4A-4C show three hypotheses for mTORC2 regulation by insulin.

FIG. 4A shows a schematic representation of the insulin-induced mTORC1-mTORC2 pathway with three different hypotheses (1, green; 2, purple; 3, dark blue) for mTORC2 activation. Network components that were targeted for perturbations are highlighted.

FIG. 4B shows a reduced graphical network model including the three hypotheses (1, 2, 3, indicated by the dotted lines), translated into different network structures.

FIG. 4C shows a comparisons of simulated time courses, calibrated for each hypothesis, with experimental data. Data shown are for mTORC2 readouts (mTOR-pS2481, Akt-pS473), the PI3K readout Akt-pT308, and the mTORC1 readout p70S6K-pT389 (see FIG. 17 for curves of all other readouts).

Figure 5:
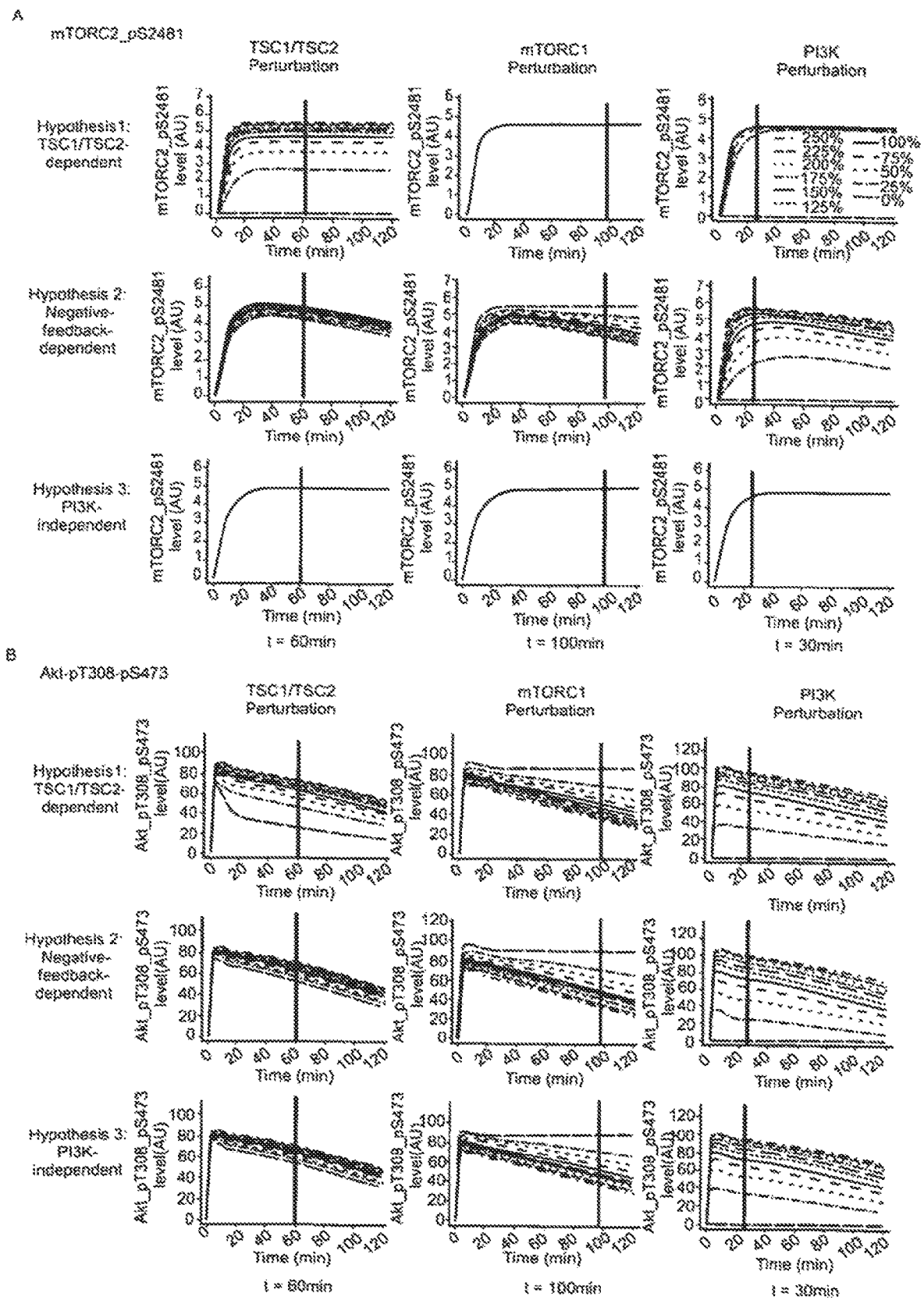
FIGS. 5A-5B: Simulations of network perturbations at several levels within the network and differential dynamic network responses for the three different hypotheses.

In FIGS. 5A-5B simulations of network perturbations at several levels within the network and differential dynamic network responses for the three different hypotheses are shown.

FIG. 5A shows a simulated mTOR-pS2481 response upon aa/insulin induction in systems with the indicated perturbations: TSC1/TSC2 (experimental equivalent: gradual TSC2 knockdown), mTORC1 (experimental equivalent: gradual Raptor knockdown), and PI3K (experimental equivalent: gradual PI3K inhibition with Wortmannin) for Hypothesis 1, 2, and 3. The time points that were experimentally tested are indicated with green lines.

FIG. 5B shows a simulated Akt-pT308-pS473 response for each of the three hypotheses upon aa/insulin induction in systems with perturbations of TSC1/TSC2, mTORC1, and PI3K. The time points that were experimentally tested are indicated with green lines.

Figure 6:
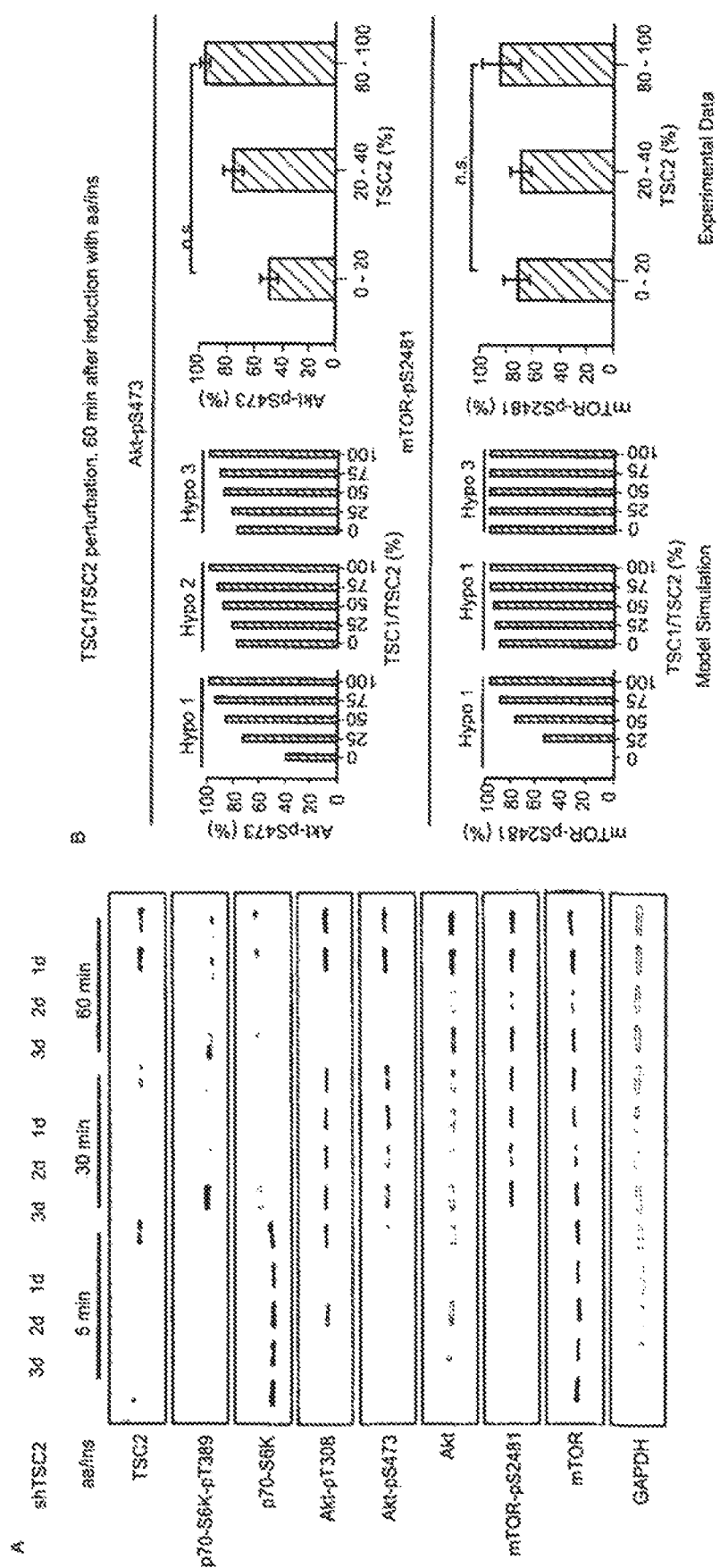
FIGS. 6A-6B: mTOR-pS2481 is not directly activated by TSC1/TSC2.

FIGS. 6A-6B show mTOR-pS2481 is not directly activated by TSC1/TSC2.

FIG. 6A shows a representative immunoblot results of the network response upon mTOR network activation in cells in which TSC2 was knocked for the indicated amounts of time. Data are representative of 3 experiments. d=days FIG. 6B shows a quantitative representations of simulated and experimentally determined AktpS473 and mTORpS2481 dynamics 60 min after induction with aa/insulin in response to a gradual TSC2 knock down.

Left: Relative quantitations of the simulated AktpS473 and mTORpS2481 behavior for the three hypotheses (Hypo 1, 2, 3) upon gradual TSC2 knock down. The amount of TSC1/TSC2 is indicated as a percent of the total in the control system in the absence of knock down.

Right: Quantitations of experimental results for 60 minutes after induction with aa/insulin in cells in which TSC2 was reduced to the indicated amounts (percent of total). Values from three independent experiments were merged and grouped according to amount of TSC2. ** $P<0.01$, n.s. not significant; low TSC2 levels compared to high TSC2 levels. Differences were significant for Akt-pS473 and not significant for mTOR-pS2481.

Figure 7:
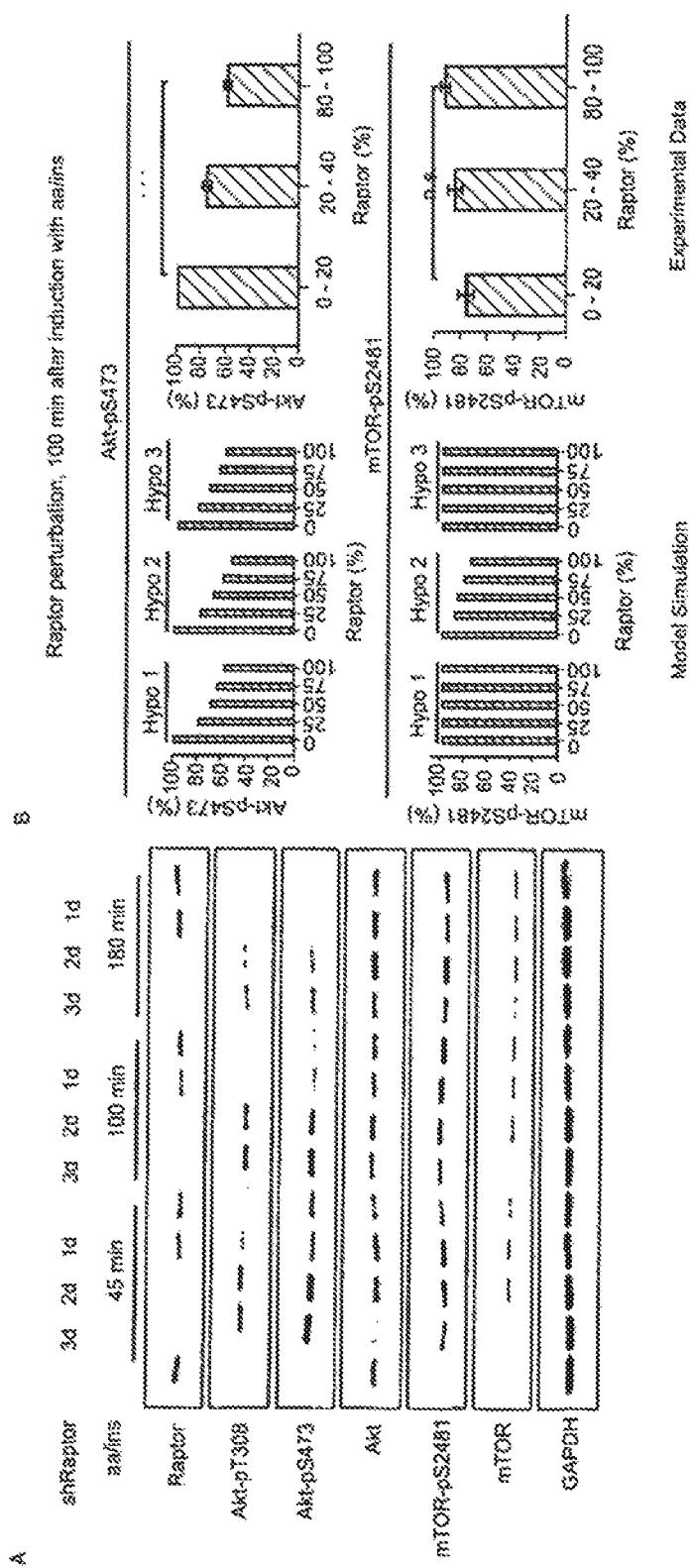
FIG. 7A-7B: mTOR-pS2481 is not affected by the NFL.

In FIGS. 7A-7B mTOR-pS2481 is not affected by the NFL is shown.

FIG. 7A shows a representative immunoblot results of the network response upon mTOR network activation in cells in which Raptor was knocked for the indicated amounts of time. Data are representative of 3 experiments. d=days FIG. 7B shows a quantitative representations of simulated and experimentally determined AktpS473 and mTORpS2481 dynamics 100 minutes after induction with aa/insulin in response to knock down of Raptor to the indicated amounts (percent of total in the absence of knock down).

Left: Relative quantitations of the simulated AktpS473 and mTORpS2481 behavior for the three hypotheses (Hypo 1, 2, 3) upon a gradual Raptor knock down.

Right: Quantitations of experimental results 100 minutes after induction with aa/insulin in cells in which Raptor was knocked down to the indicated amounts (percent of total). Values from three independent experiments were merged and grouped according to the amount of Raptor. Data are the average and XX. *** P<0.001, n.s. not significant; low Raptor levels compared to high Raptor levels. Differences were significant for Akt-pS473 and not significant for mTOR-pS2481.

Figure 8:
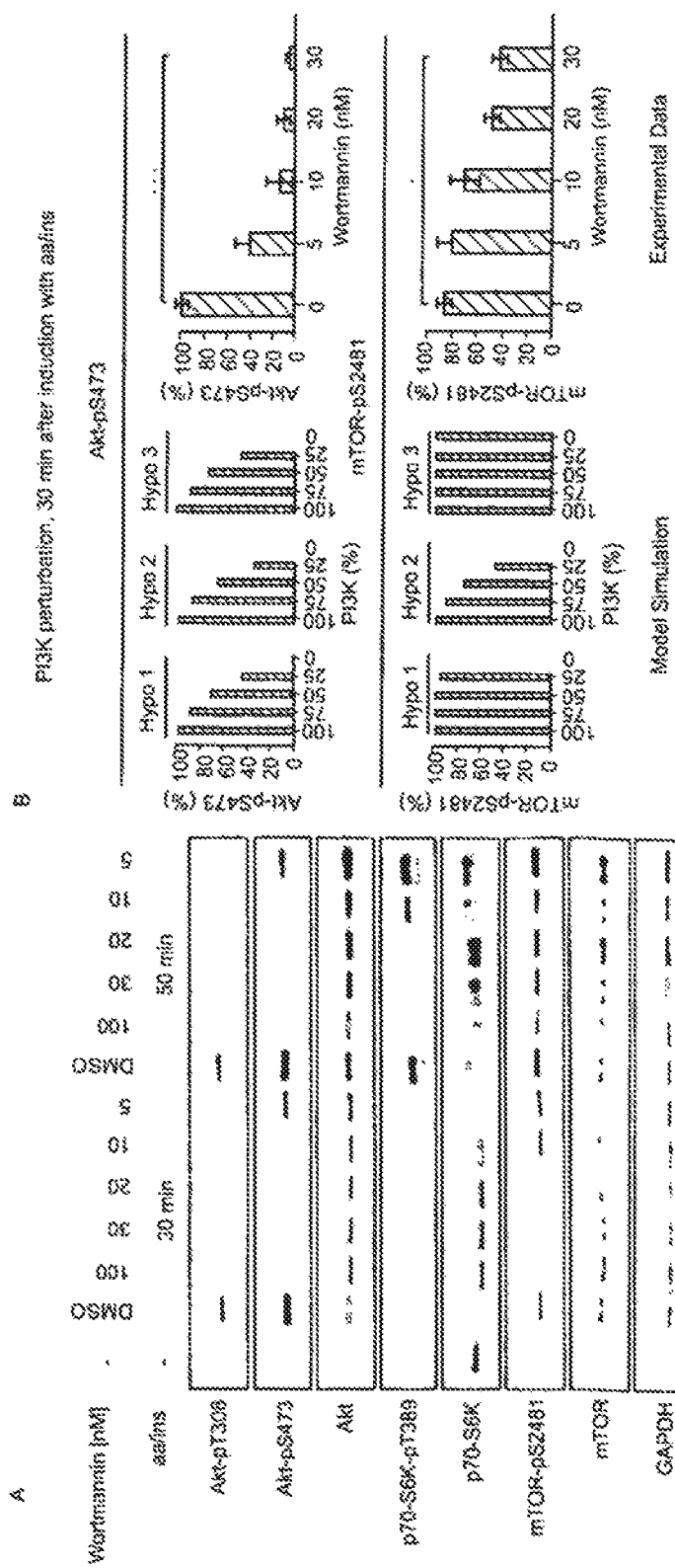
FIGS. 8A-8F: mTOR-pS2481 is sensitive to the PI3K inhibitor Wortmannin (Wmn)

FIGS. 8A-8B show a mTOR-pS2481 being sensitive to the PI3K inhibitor Wortmannin (Wmn).

FIG. 8A shows a representative immunoblot results of the network response upon mTOR network activation with aa/insulin in the presence of Wortmannin to inhibit PI3K. Data are representative of 3 experiments.

FIG. 8B shows a quantitative representations of simulated and experimentally determined AktpS473 and mTORpS2481 dynamics 30 min after induction with aa/ins in cells in which PI3K activity was inhibited to the indicated amount (percent of total activity).

Left: Relative quantitations of the simulated AktpS473 and mTORpS2481 behavior for the three hypotheses (Hypo 1, 2, 3) in response to gradual PI3K inhibition (percent of total activity).

Right: Quantitations of experimental results 30 minutes after induction with aa/ins in cells in which PI3K was inhibited with the indicated concentrations of Wortmannin. Data are the average and XX of 3 experiments. * P<0.05, *** P<0.001; 30 nM compared to 0 nM Wortmannin. Differences were significant for both Akt-pS473 and mTORpS2481.

In FIGS. 9A-9F a new hypothesis and network structure for mTORC2 regulation by insulin is shown.

Figure 9A:
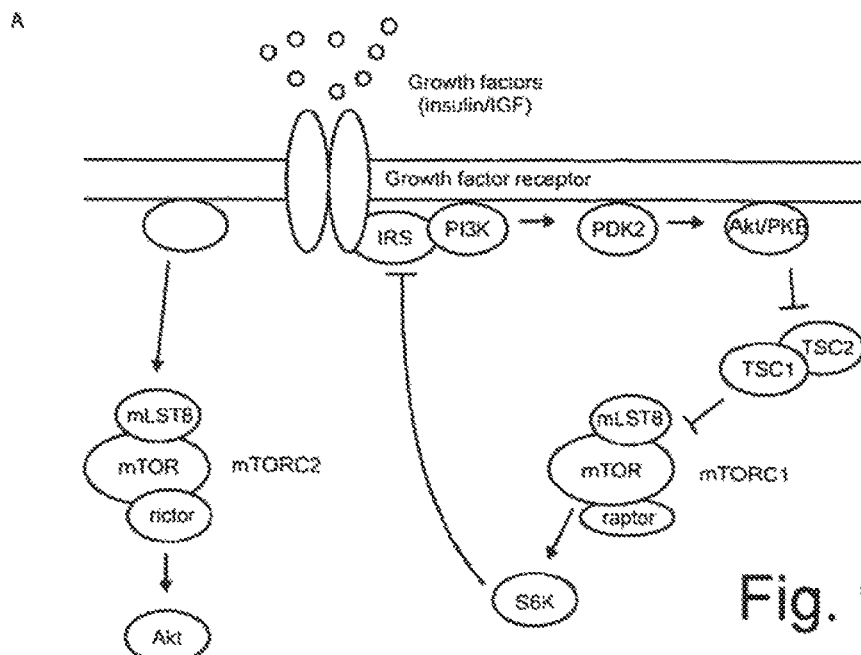
FIGS. 9A-9F: A new hypothesis and network structure for mTORC2 regulation by insulin.

FIG. 9A shows a schematic representation of the pathway for Hypothesis 4: Insulin induction of mTORC2 by a PI3K (red) that is insensitive to TSC1/TSC2 and to the S6K to IRS-mediated NFL.

Figure 9B:
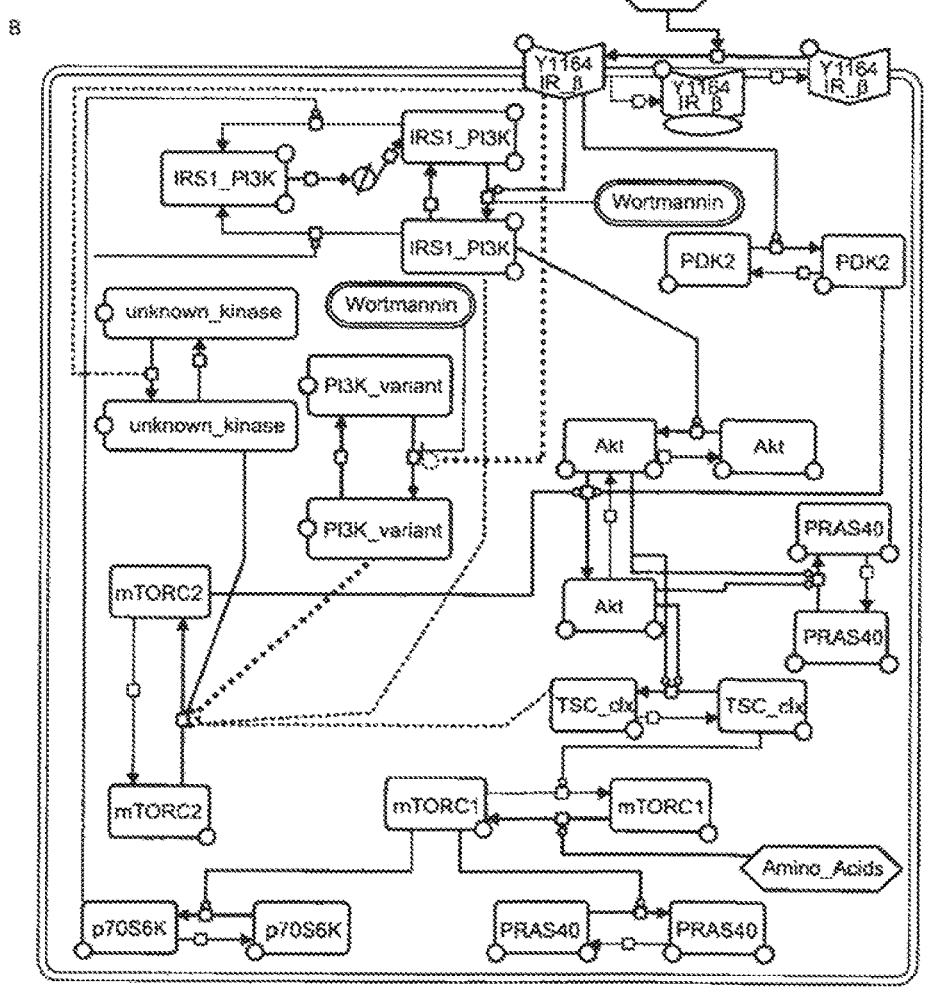

FIG. 9B shows a computational model corresponding to Hypothesis 4. This hypothesis was equivalent to Hypothesis 3 (PI3K and TSC1/TSC2-independent activation), assuming that the mTORC2 activator was sensitive to Wortmannin.

Figures 9C, 9D, 9E, 9F:
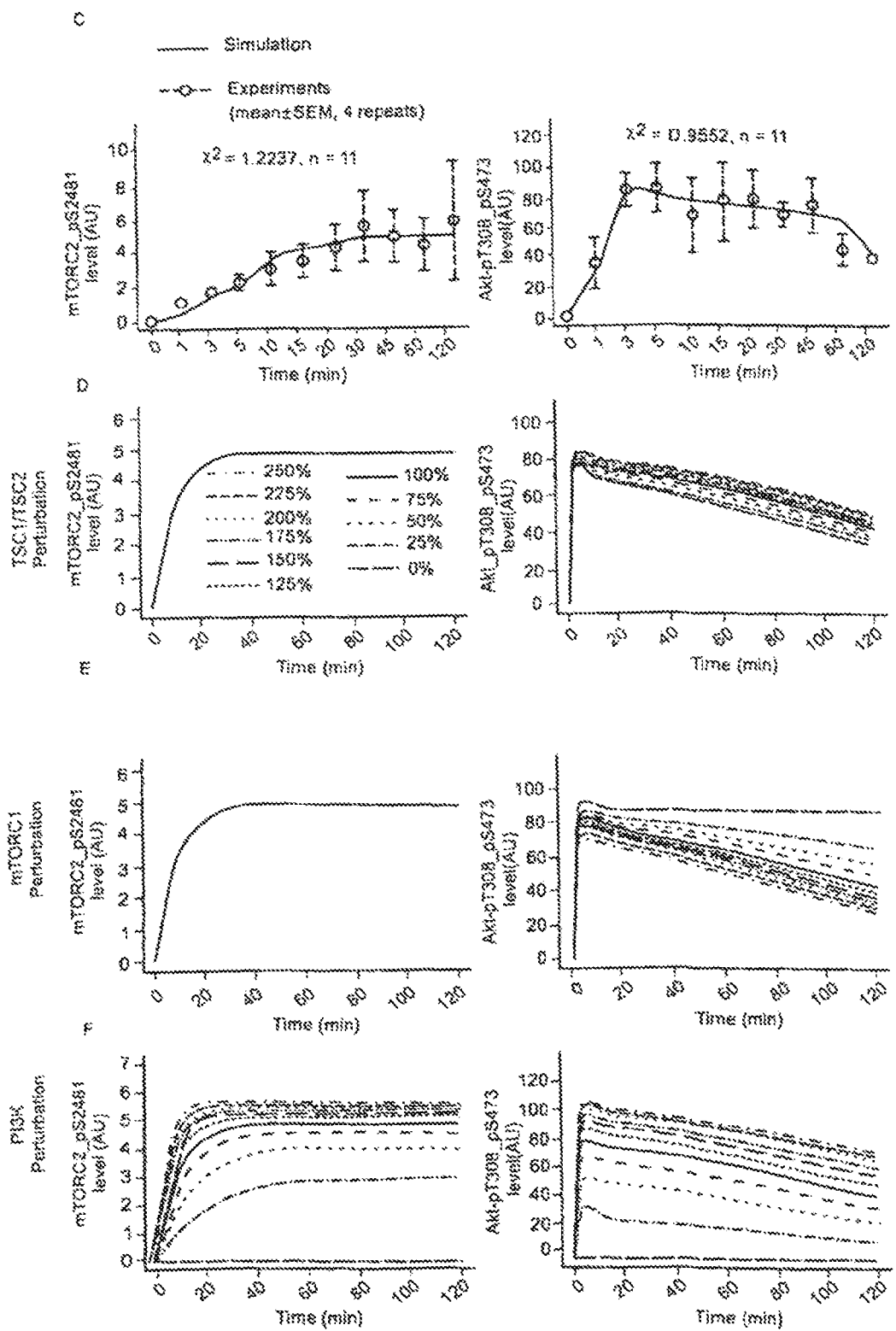

FIG. 9C shows the model simulation data for Hypothesis 4 match the experimental dynamic phosphorylation data. The simulated and experimentally measured dynamics are shown for the mTORC2 readouts mTOR-pS2481 and Akt-pS473 (see FIG. 26 for all other readouts).

FIG. 9D shows predictions for mTOR-pS2481 and Akt-pS473 upon gradual TSC1/TSC2 knock down match the experimental data, which is presented in FIGS. 6A and B (right side). Whereas at 60 min after induction Akt-pS473 is gradually reduced by TSC2 inhibition, mTOR-pS2481 is TSC2-insensitive. See FIG. 26 for Akt-pT308 and p70S6K-pT389.

FIG. 9E shows predictions for mTOR-pS2481 and Akt-pS473 readouts upon gradual Raptor knock down match the experimental data, which is presented in FIGS. 7A and B (right side). Whereas at 100 min after induction Akt-pS473 is gradually induced by Raptor inhibition, mTORpS2481 is Raptor-insensitive. See FIG. 26 for Akt-pT308 and p70S6 KpT389.

FIG. 9F shows predictions for mTOR-pS2481 and Akt-pS473 readouts upon gradual PI3K inhibition match the experimental data, which is presented in FIGS. 8A and B (right side). Both AktpS473 and mTORpS2481 are gradually reduced by Wortmannin at 30 min after induction. See FIG. 26 for Akt-pT308 and p70S6 KpT389.

FIGS. 10A-10G show a mTORC2 activation is dependent on PI3K but is independent of Akt.

Figure 10:
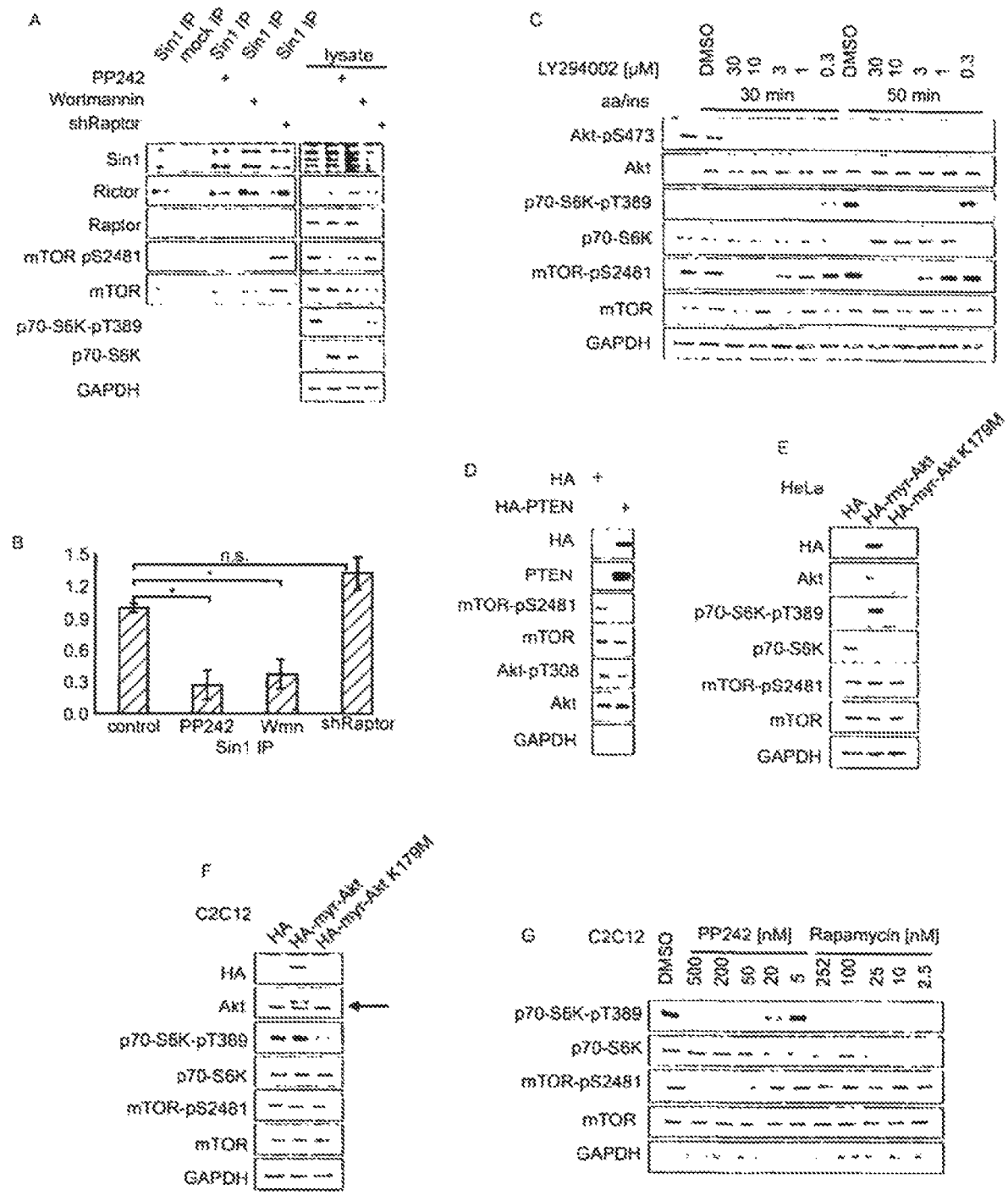
FIGS. 10A-10G: mTORC2 activation is dependent on PI3K but is independent of Akt.

FIG. 10A shows a coimmunoprecipation of mTOR-pS2481 in HeLacells in the presence or absence of Wortmannin, PP242, or Raptor knockdown. mock IP=control IP with a non-specific antibody. Data are representative of 3 experiments.

FIG. 10B shows a quantitation of data from 3 experiments like that shown in (A) for mTOR-pS2481 relative to total amount of immunoprecipitated mTOR. * P<0.05, n.s., not significant; PP242 and Wortmannin (Wmn) treatments compared to control. Differences in mTORpS2481 association were significant. Raptor knock down compared to control. Differences in mTORpS2481 association were not significant.

FIG. 10C shows the effect of the PI3K inhibitor LY294002 on mTOR-pS2481 and other components of the mTOR network in HeLacells. Data shown are representative of 3 experiments.

FIG. 10D shows the effect of HA-tagged PTEN overexpression on mTOR-pS2481. Data are representative of 3 experiments. HA=HeLa cells transfected with empty vector control.

FIG. 10E shows the effect of constitutively active (HA-myr-Akt) or kinase-dead (HA-myr-Akt K179M) Akt on mTOR-pS2481 and other components of the mTOR network in HeLa cells. Data are representative of 3 experiments.

FIG. 10F shows the effect of constitutively active (HA-myr-Akt) or kinase-dead (HA-myr-Akt K179M) Akt on mTOR-pS2481 and other components of the mTOR network in C2C12 myoblasts. The specific Akt signal is indicated by an arrow. Data are representative of 3 experiments.

FIG. 10G shows a confirmation that mTOR-pS2481 is a specific mTORC2 readout in C2C12 myoblasts. The indicated proteins were detected in cells in the presence or absence of the indicated concentrations of PP242 or Rapamycin in the continuous presence of aa/insulin. Data are representative of 3 experiments.

Figure 11A:
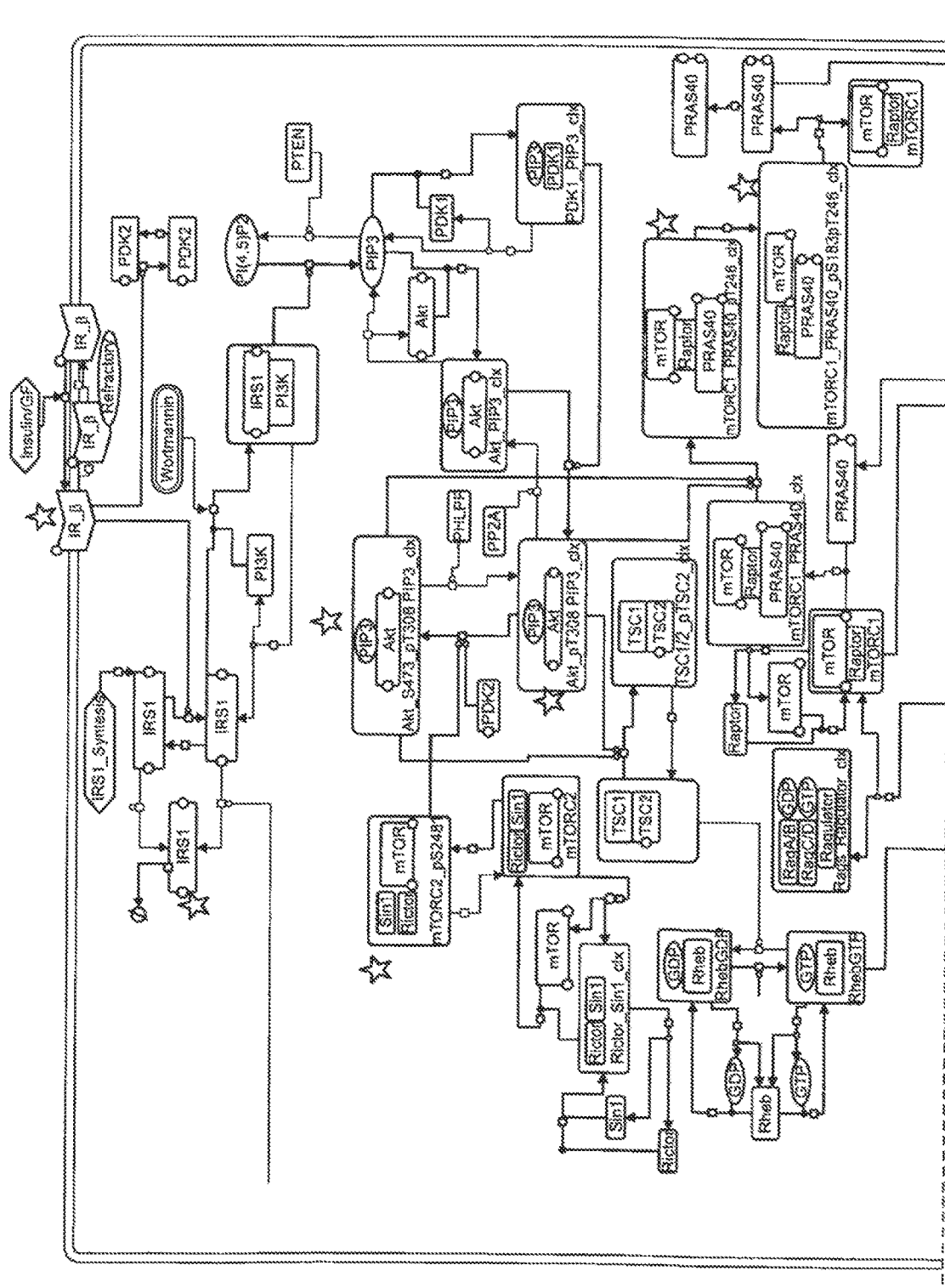
FIGS. 11A-11B: Extended graphical model of the mammalian TOR network.
Figure 11B:
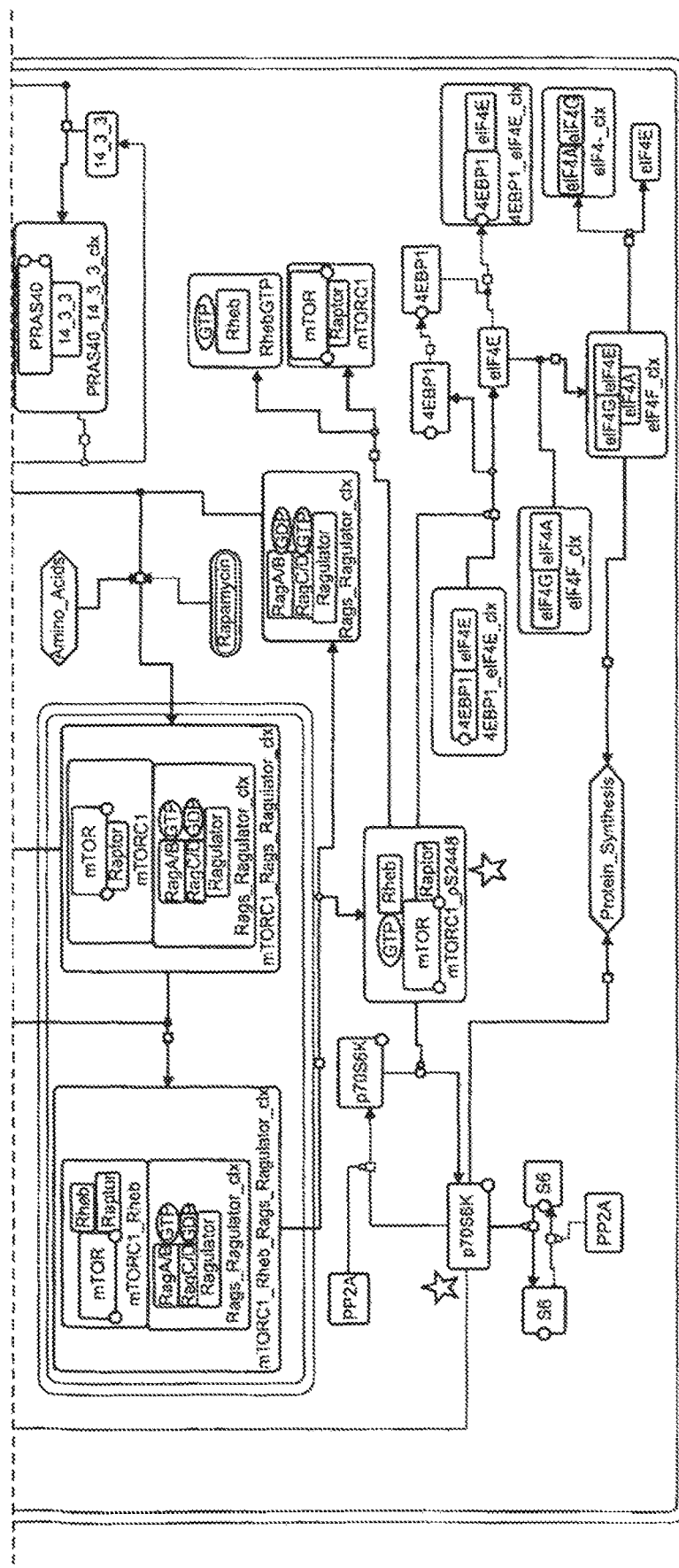

FIGS. 11A-11B show an extended graphical model of the mammalian TOR network. A static network model of TOR signaling stimulated by amino acids plus insulin (aa/insulin) is shown in SBGN notation. This model integrates the current knowledge and guided our decision on appropriate targets for measurement. The selected targets are marked with an asterisk.

Figure 12:
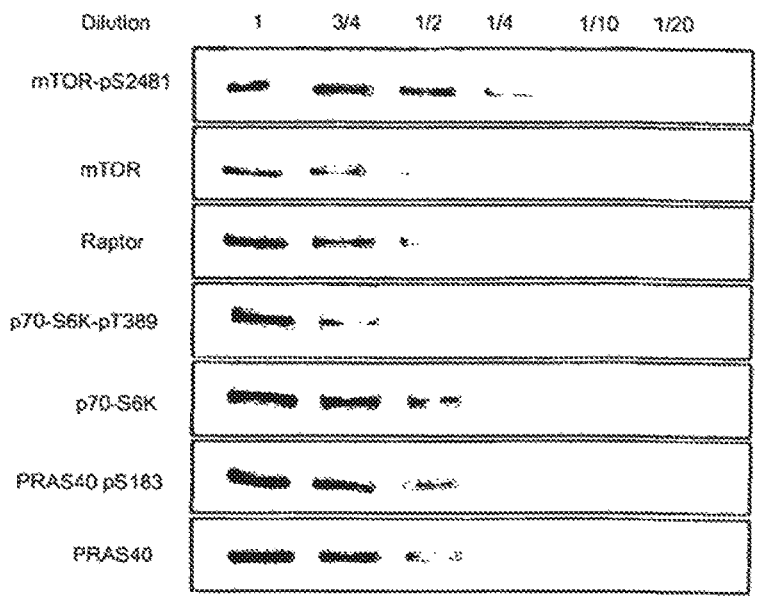
FIG. 12: Western blot signals are in linear relationship to protein concentrations.

FIG. 12 shows a linear relationship between Western blot signals and protein concentrations. HeLa cells were lysed and cell lysates were diluted as indicated and analyzed by Western blotting. The linearity of signal to protein amount ratio was confirmed for selected antibodies used in this study.

Figure 13:
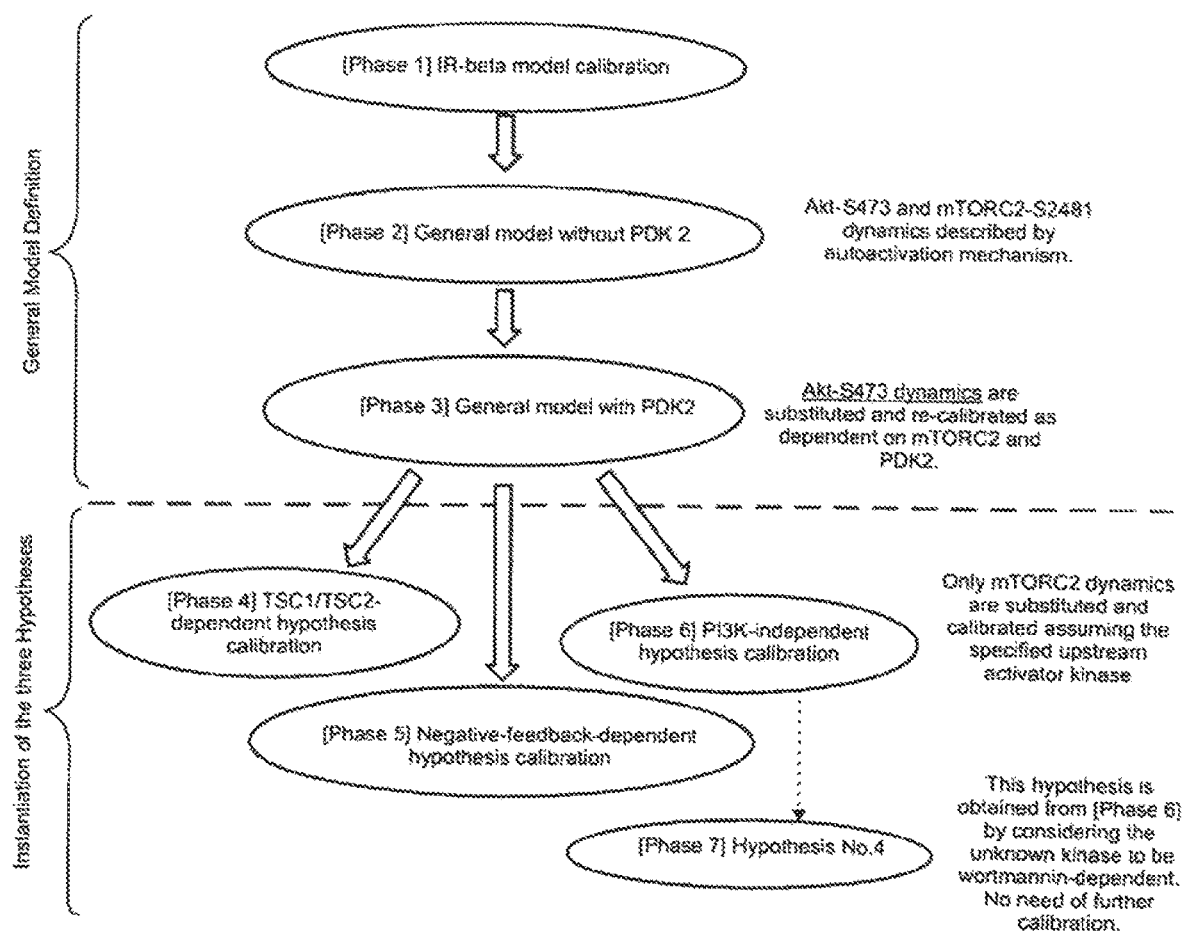
FIG. 13: Phases of the calibration process.

FIG. 13 shows phases of the calibration process. The approach for defining our model was hierarchical and structured in two main parts. Part 1 (Phases 1-3) was the development of a general model without regulation of mTORC2 and part 2 was the introduction of specific hypotheses for regulation of mTORC2. In Phase 1, the kinetic rate constants of the insulin receptor were calibrated independently because the insulin receptor module was not regulated by the rest of the network. In Phase 2, the kinetic rate constants for the model representing the entire network without PDK2 were calibrated, assuming that the phosphorylation dynamics of mTOR-S2481 and Akt-S473 dynamics were regulated by autoactivation. In Phase 3, PDK2 was added to the network and the autoregulation mechanism controlling phosphorylation of Akt-S473 was replaced with the regulation by both mTORC2 and PDK2. Part 2 (Phases 4-6) of the calibration process concerned the introduction of the three hypotheses (Hypothesis 1, 2, and 3) for mTORC2 activation from the general model defined in part 1 (Phase 3). The development and calibration of these hypotheses only required substitution of the mTORC2 dynamics of the general model with the specific regulation of the corresponding hypothesis and then recalibration of these new kinetic parameters. In Phase 7, Hypothesis 4 was obtained from the PI3K-independent model by transforming the unknown kinase into one dependent on Wortmannin, which did not involve further calibration.

Figure 14:
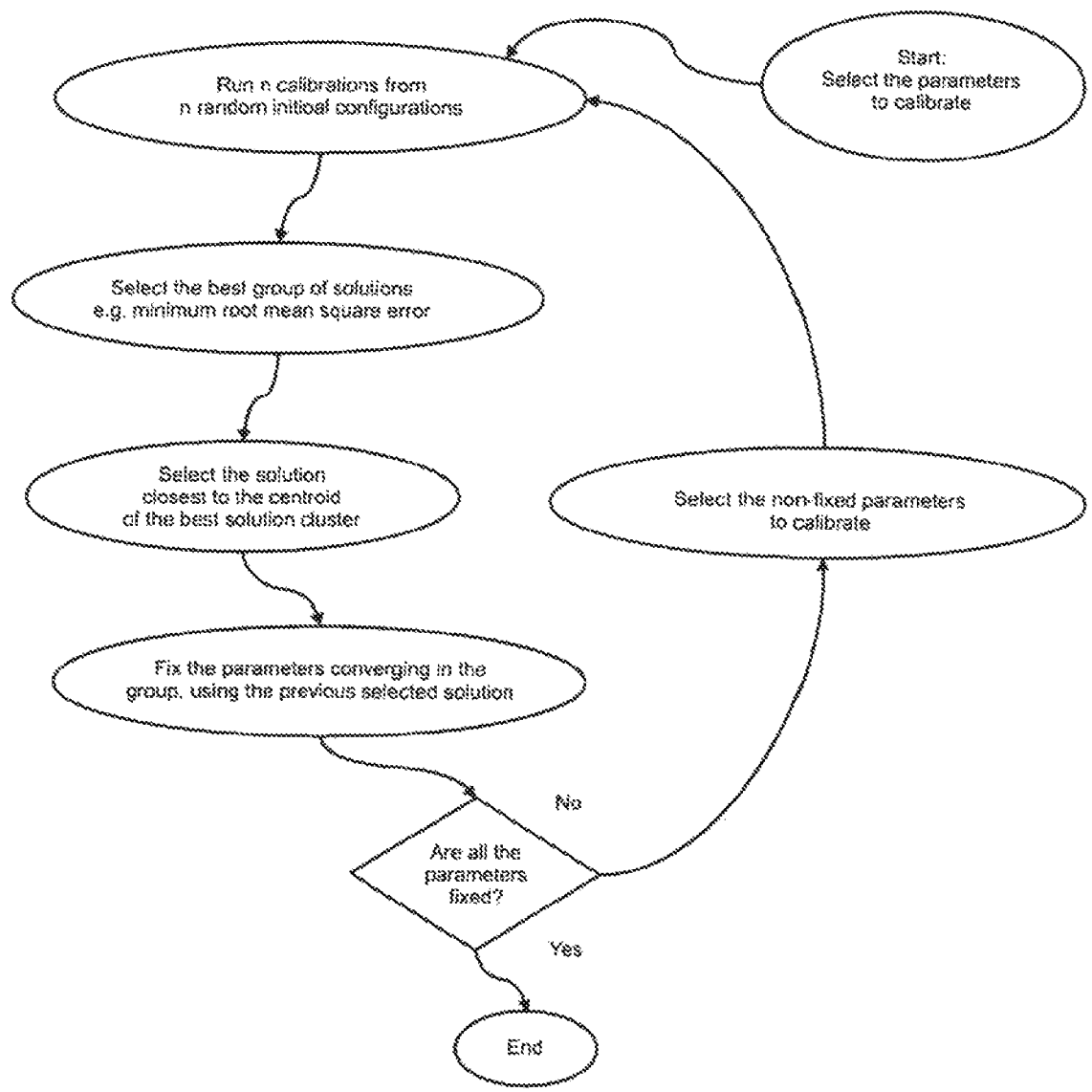
FIG. 14: Details of a calibration phase.

In FIG. 14 details of a calibration phase are shown. The flow chart shows the details of the parameter calibration procedure. The procedure began with the selection of the set of parameters to estimate. After completing the calibrations, the procedure selected the subset of the solutions that obtained the minimum root mean square error (best solutions). The closest solution to the centroid of the best solution cluster was selected and the values common to all the solutions were fixed. All the parameters that were not fixed were selected for the next step of calibration. The procedure terminated when there were no further parameters to calibrate. In our model calibration, all the parameters were identified in only one iteration step.

Figure 15:
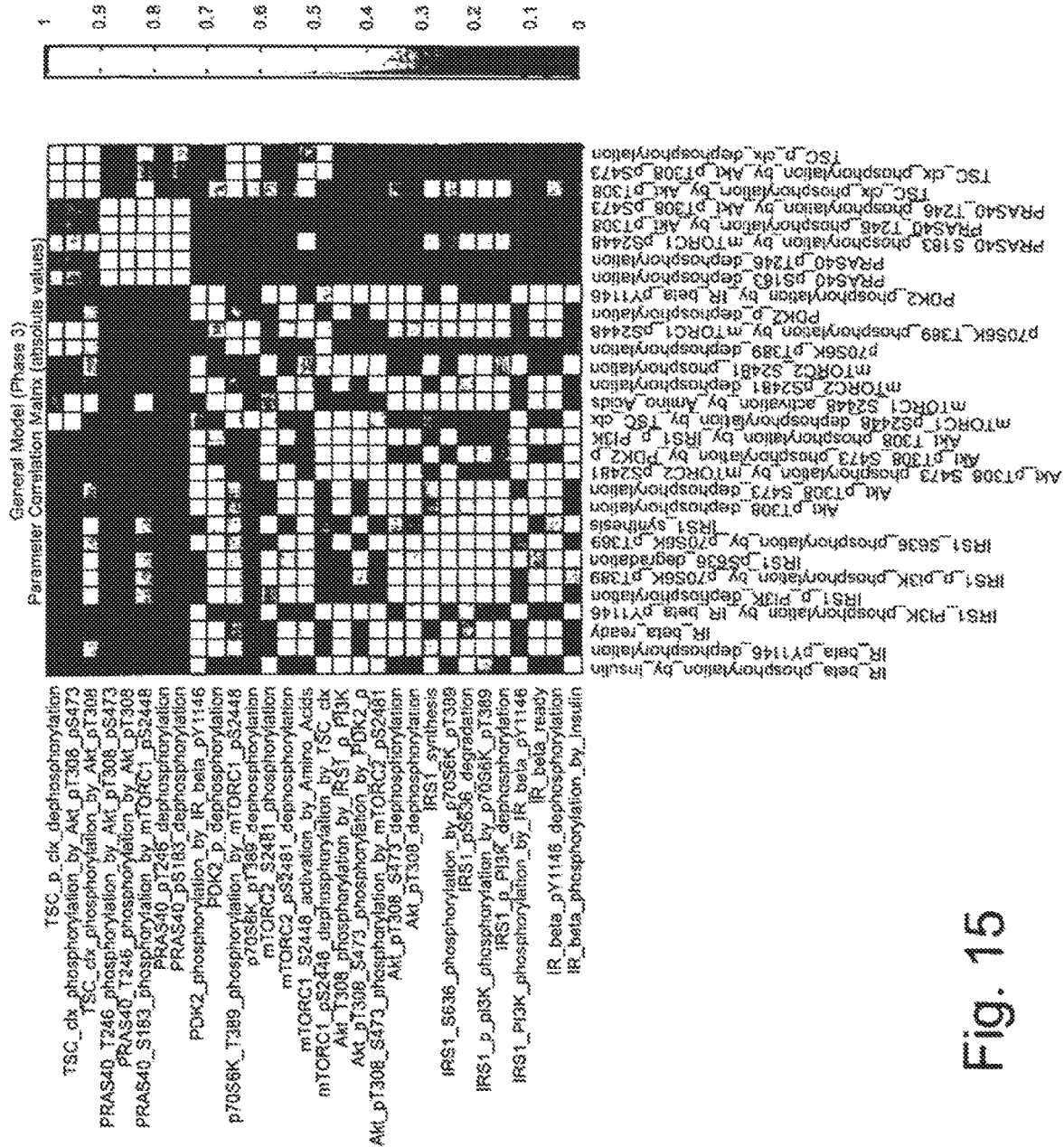
FIG. 15: Identifiability analysis for the general model.

FIG. 15 shows a dentifiability analysis for the general model. Parameter identifiability is based on sensitivity analysis and parameter correlation as computed by SBPD Matlab Toolbox. The symmetric matrix shows the parameter correlation in absolute values. High parameter correlations suggest potential issues in identifying the corresponding parameters independently (the elements on the diagonal obviously have correlation equal to 1). Conversely, low parameter correlations indicate that the corresponding parameters can be identified independently. Our experimental data were used in computing the reported identifiability analysis.

Figure 16:
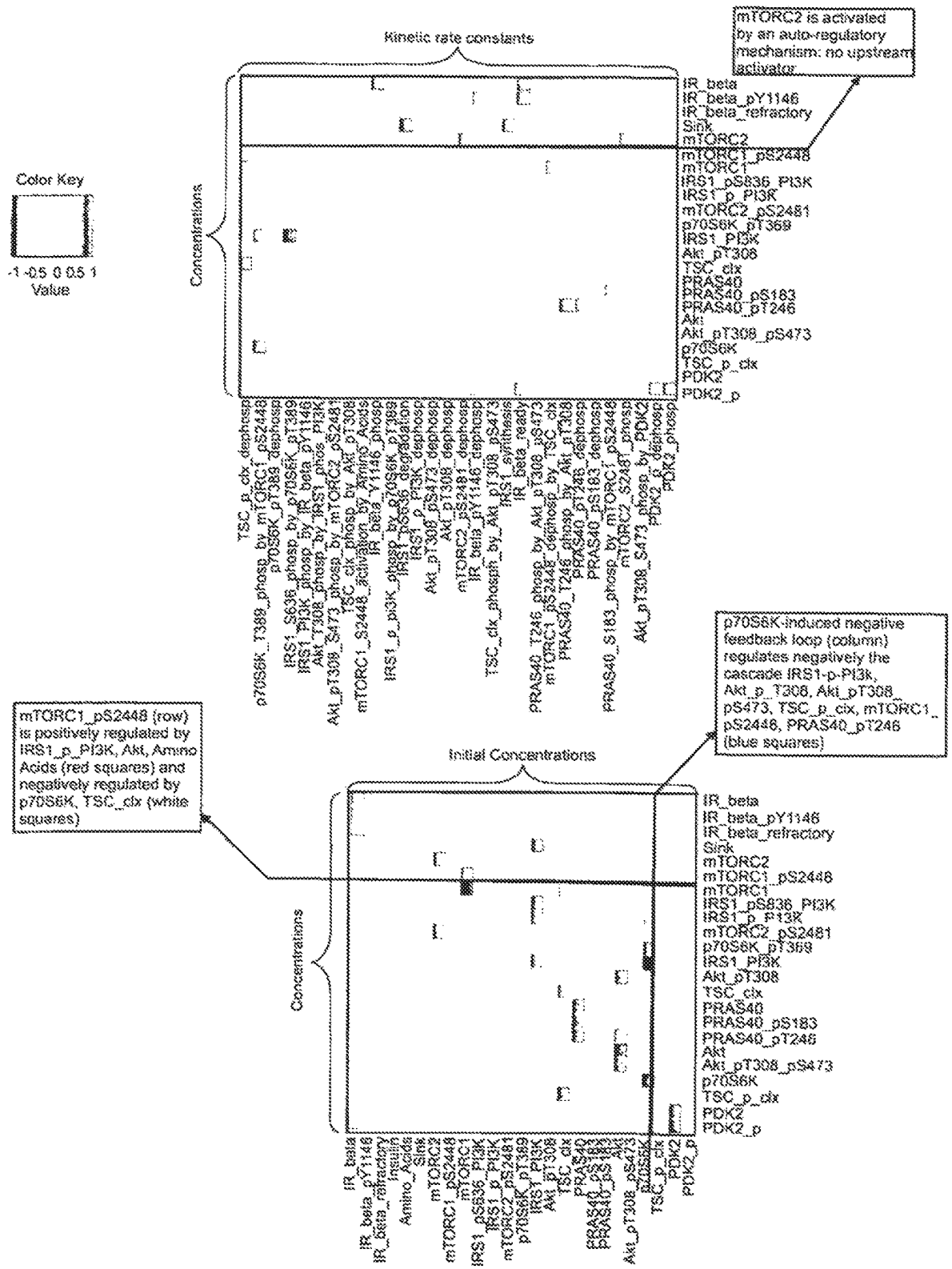
FIG. 16: Sensitivity analysis for the general model.

FIG. 16 shows a sensitivity analysis for the general model. The top plot illustrates the sensitivity analysis of the model by row, in response to the perturbations of the kinetic rates constants shown in columns. The bottom plot shows the model sensitivity analysis of the initial concentrations of the modelled species by row with perturbations shown in columns. Values were normalized in the range [−1, 1]. Positive values (red squares) represent positive regulation; negative ones (white-blue squares) represent inhibition.

Figure 17:
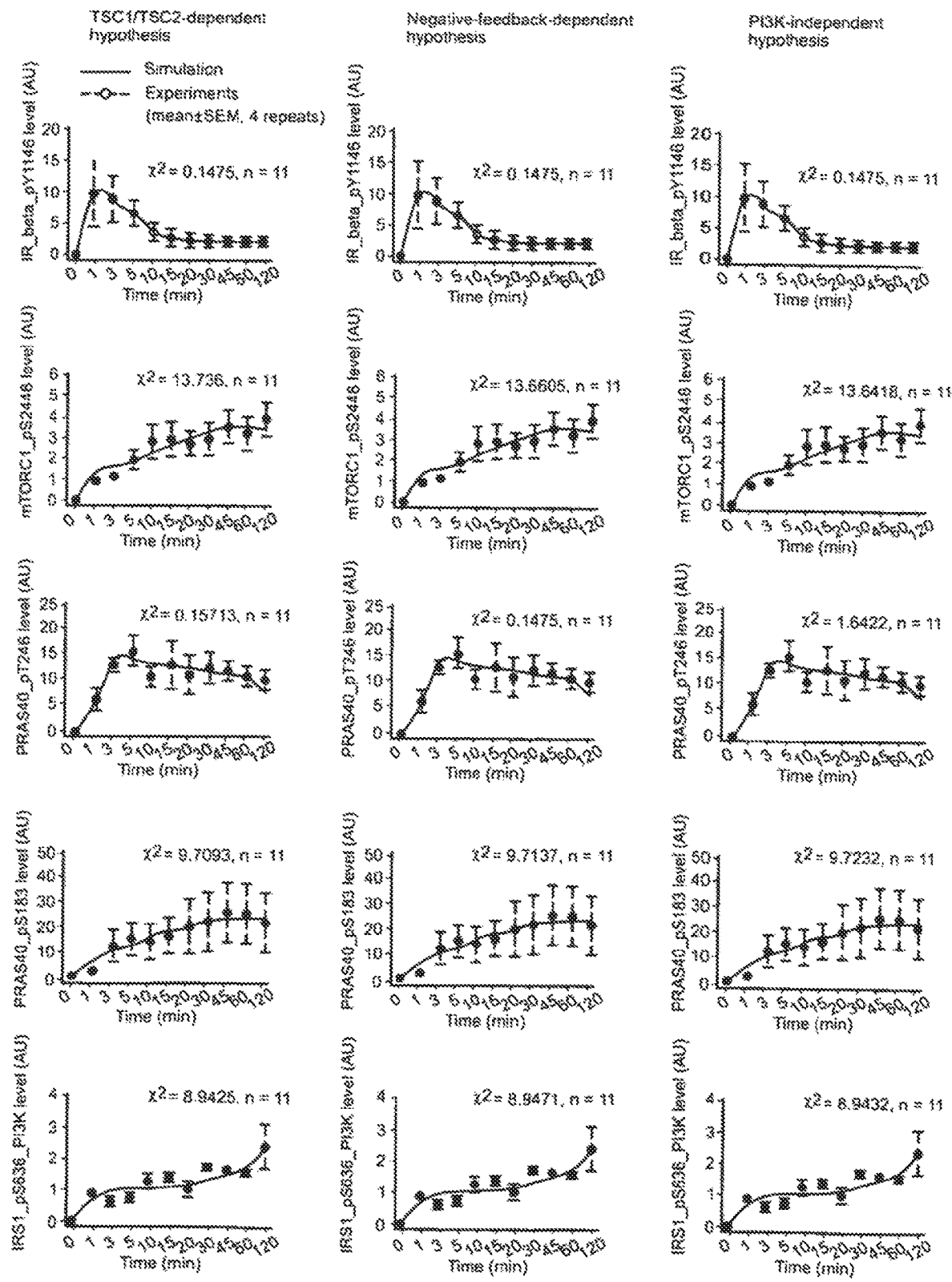
FIG. 17: Comparison between the simulated and experimental time-courses between each hypothesis for the remaining readouts.

In FIG. 17 a comparison between the simulated and experimental time-courses for Hypothesis 1, 2, and 3 for readouts of the mTOR network is shown. The three hypotheses were consistent with each other for all the readouts indicating that introducing each hypothesis into the general model did not perturb the network. NFL=Negative Feedback Loop.

Figure 18:
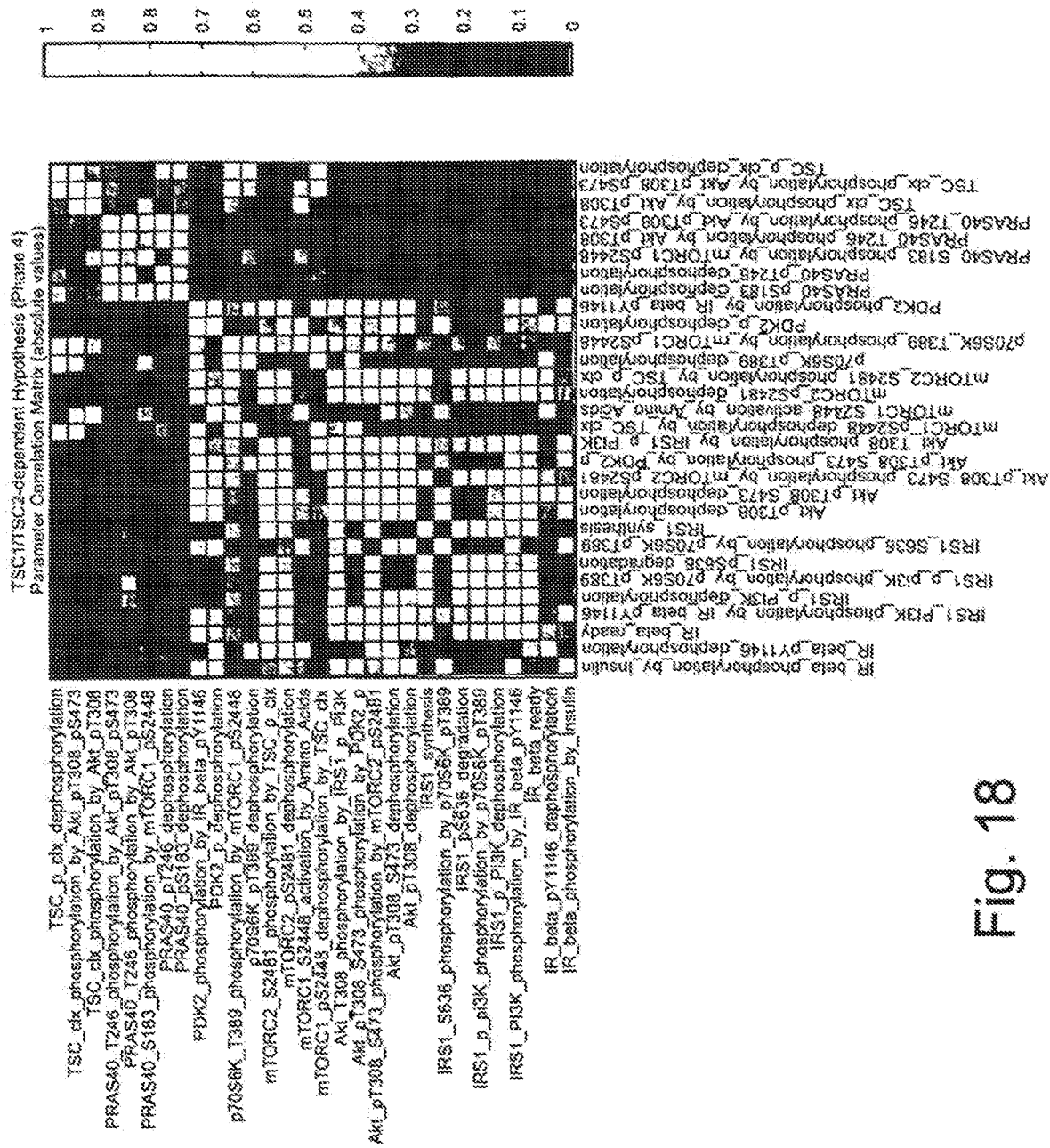
FIG. 18: Identifiability analysis for TSC1/TSC2-dependent hypothesis (hypothesis No. 1)

FIG. 18 shows a identifiability analysis for Hypothesis 1: TSC1/TSC2-dependent mTORC2 regulation. Parameter correlation matrix for TSC1/TSC2-dependent hypothesis is shown. See FIG. 25 for details.

Figure 19:
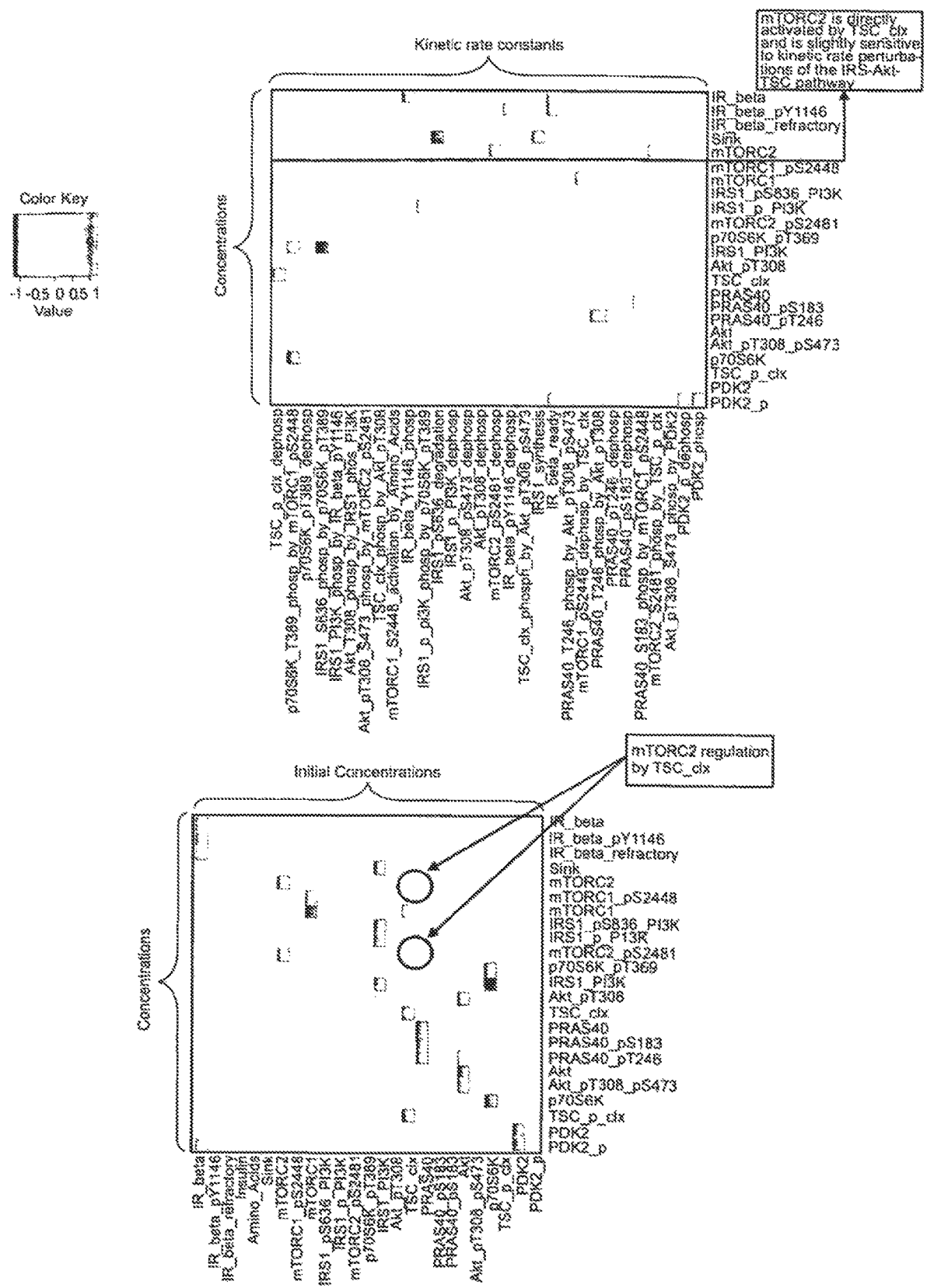
FIG. 19: Sensitivity analysis for TSC1/TSC2-dependent hypothesis (hypothesis No. 1)

In FIG. 19 a sensitivity analysis for Hypothesis 1: TSC1/TSC2-dependent mTORC2 regulation is shown. The sensitivity analyses of the three hypotheses (see FIGS. 21 and 23) showed a similar sensitivity analysis excluding the sensitivity for the parameters characterizing each specific hypothesis. This provided evidence that the proposed general model (common to the three hypotheses) behaved in a consistent manner following introduction of the three hypothetical models and, therefore, the three models were comparable. See FIG. 16 for details of the top and bottom plots.

Figure 20:
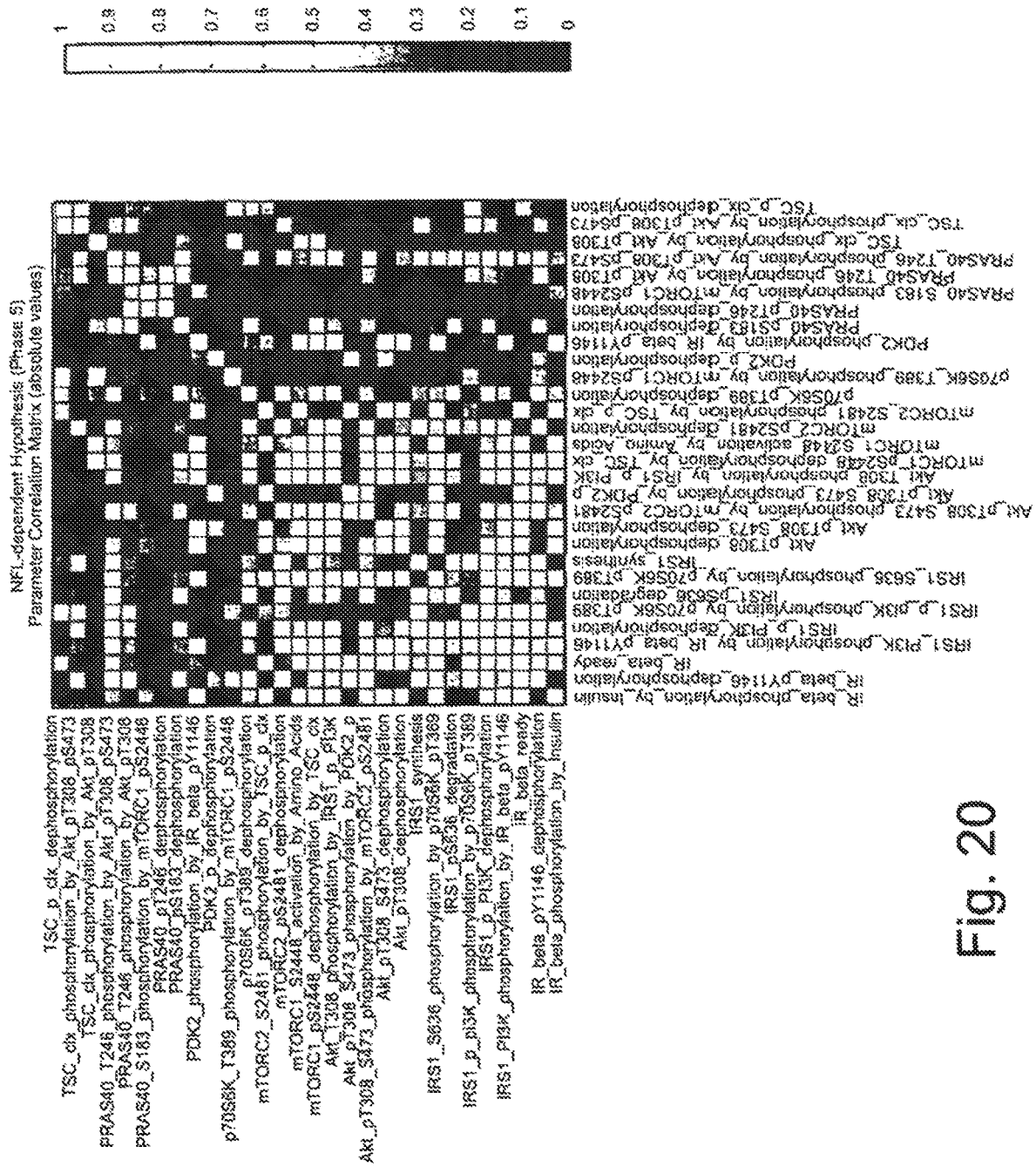
FIG. 20: Identifiability analysis for negative-feedback-dependent hypothesis (hypothesis No. 2)

FIG. 20 shows an identifiability analysis for Hypothesis 2: NFL-dependent mTORC2 regulation. Parameter correlation matrix for NFL-dependent hypothesis is shown. See FIG. 15 for details.

Figure 21:
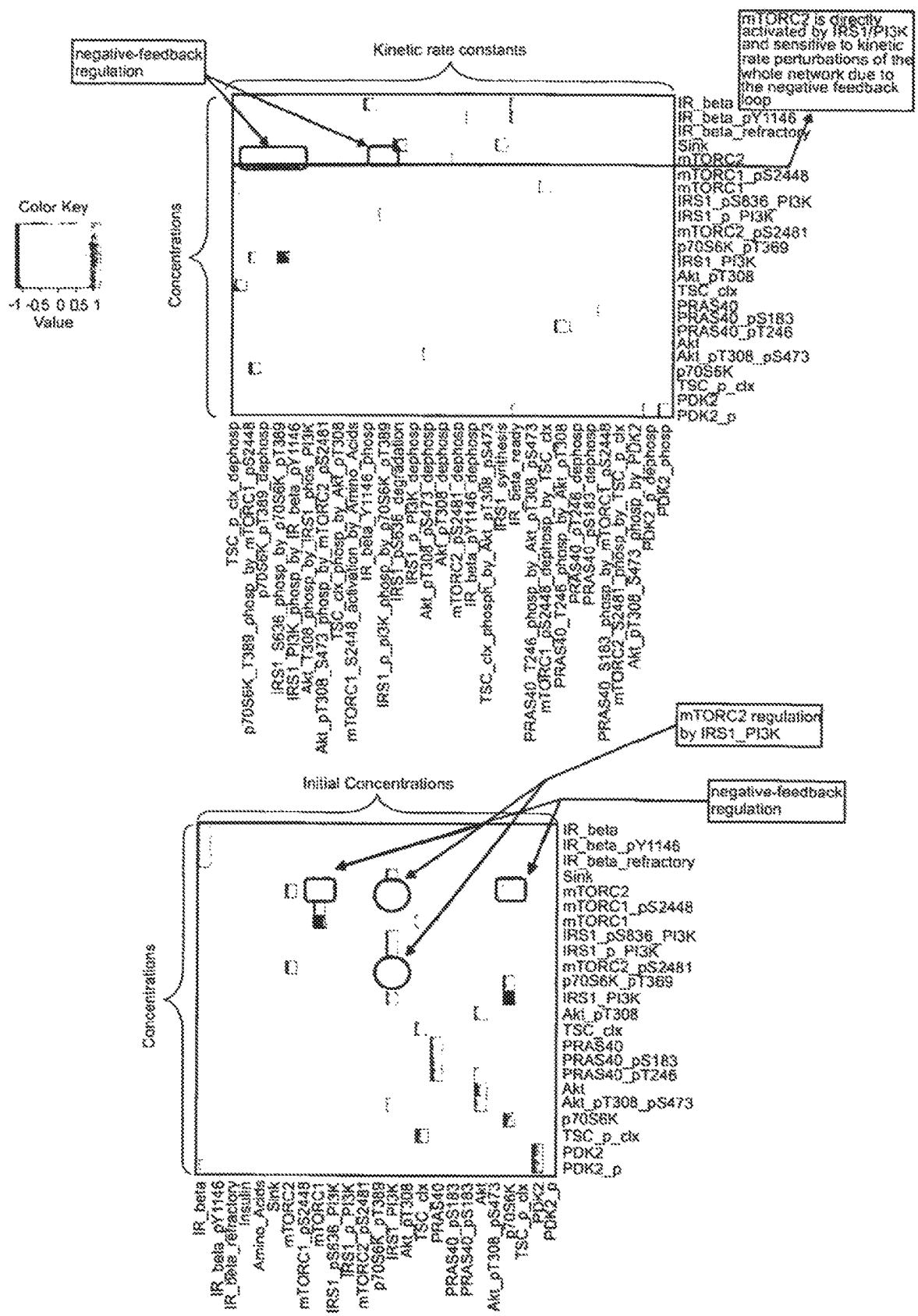
FIG. 21: Sensitivity analysis for negative-feedback-dependent hypothesis (hypothesis No. 2)

In FIG. 21 a sensitivity analysis for Hypothesis 2: NFL-dependent mTORC2 regulation is shown. Sensitivity analysis for the initial concentrations and the kinetic rates parameters for the NFL-dependent hypothesis is shown. See FIG. 16 for details of the top and bottom plots.

Figure 22:
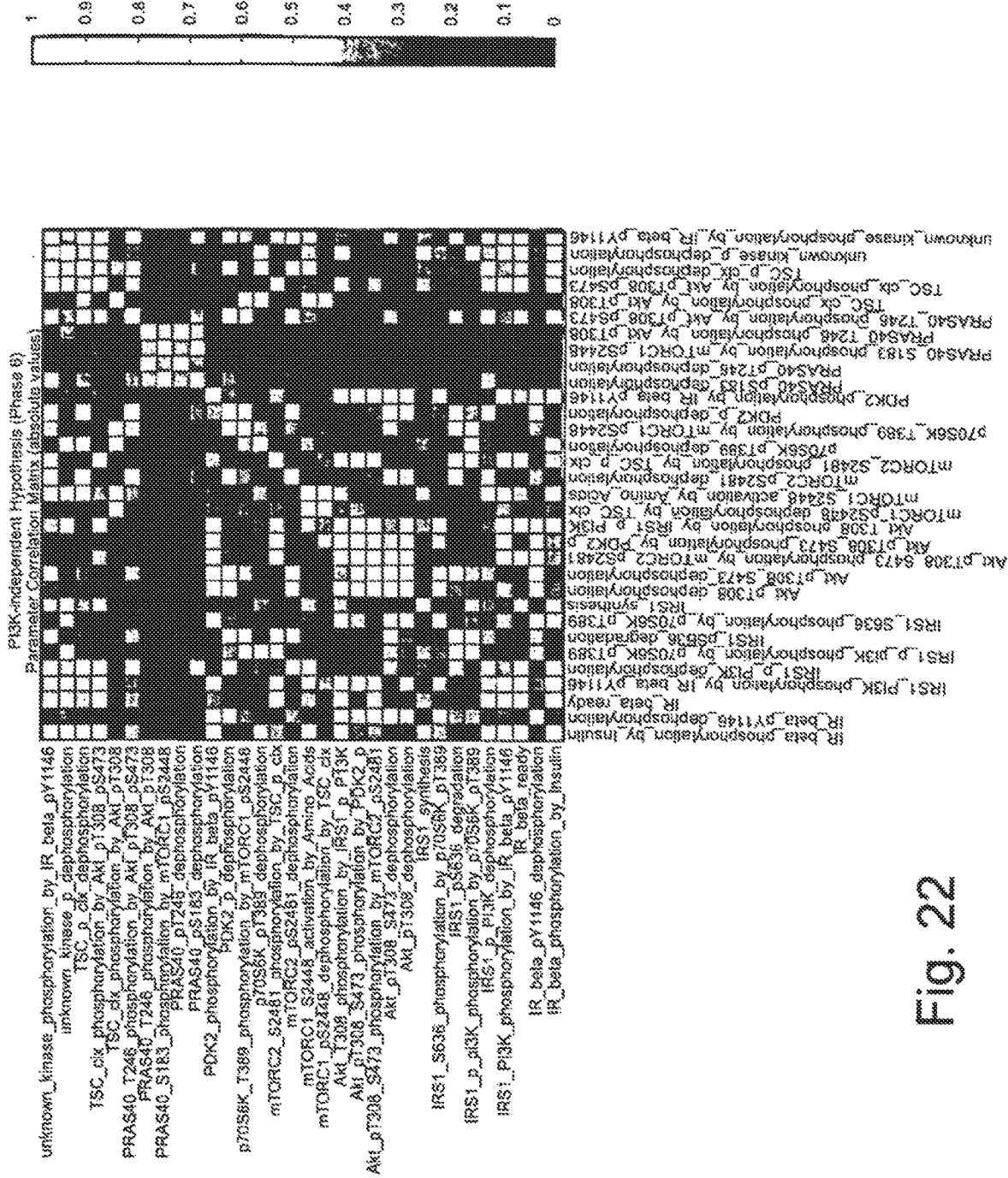
FIG. 22: Identifiability analysis for PI3K-independent hypothesis (hypothesis No. 3)

FIG. 22 shows an identifiability analysis for Hypothesis 3: PI3K-independent mTORC2 regulation. Parameter correlation matrix for PI3K-independent hypothesis is shown. See FIG. 15 for details.

Figure 23:
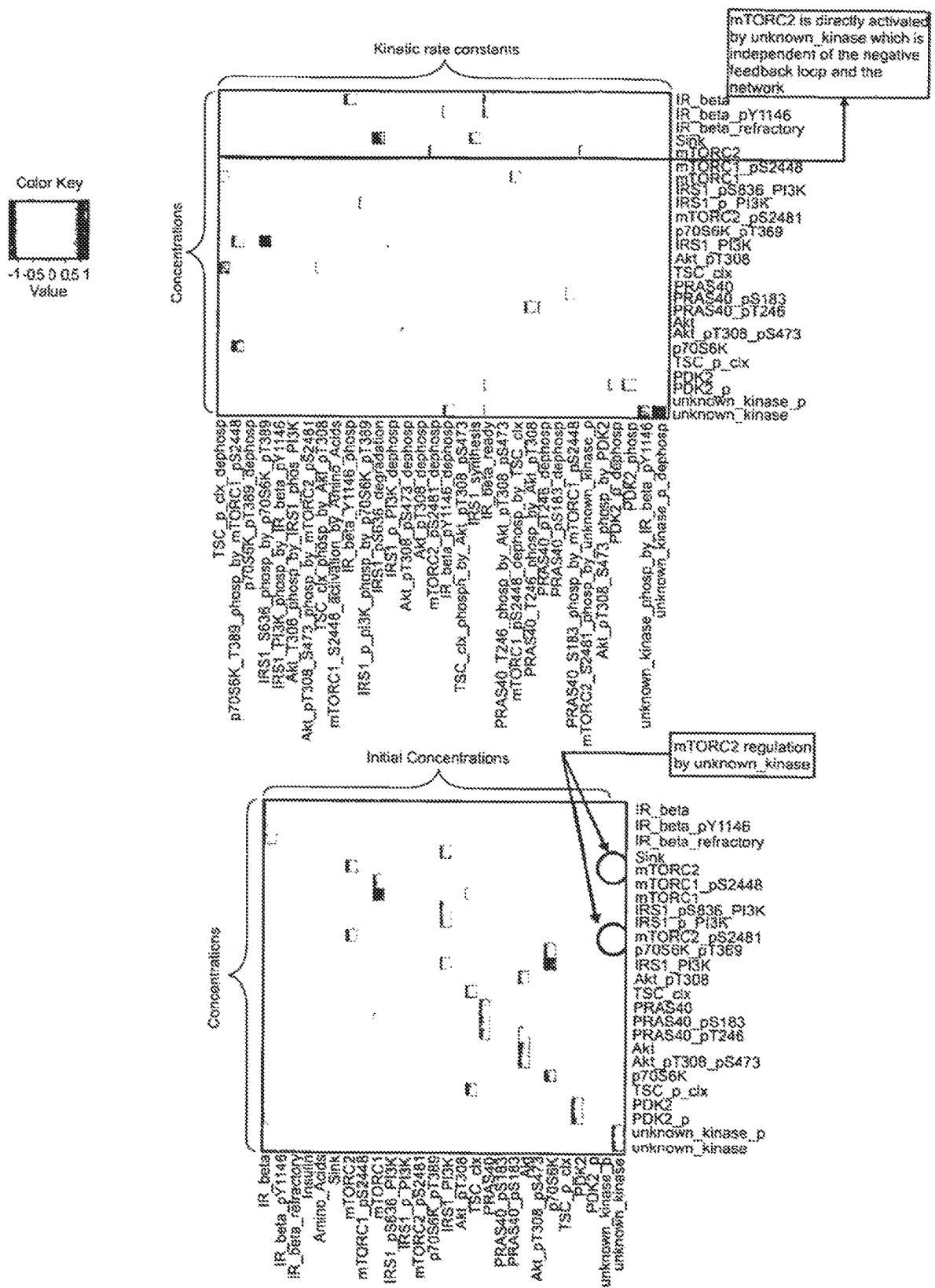
FIG. 23: Sensitivity analysis for PI3K-independent hypothesis (hypothesis No. 3)

In FIG. 23 a sensitivity analysis for Hypothesis 3: PI3K-independent mTORC2 regulation is shown. Sensitivity analysis for the initial concentrations and the kinetic rates parameters for the PI3K-independent hypothesis is shown. See FIG. 16 for details of the top and bottom plots.

Figure 24:
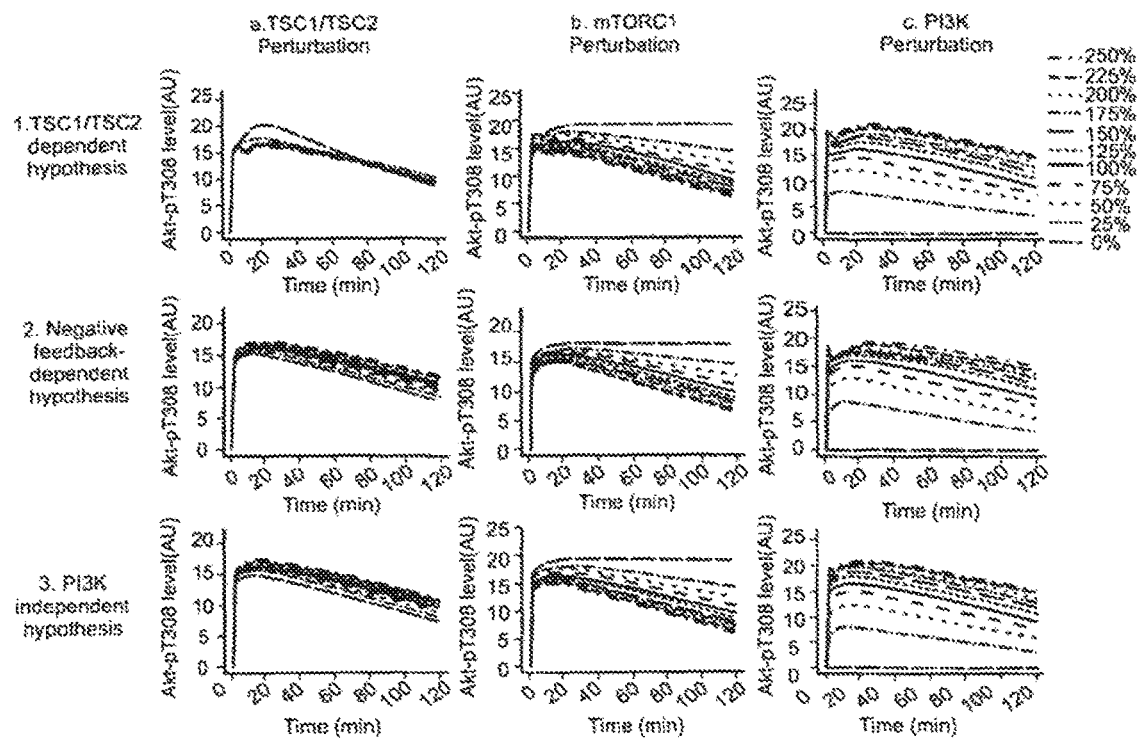
FIG. 24: The influence of perturbations of TSC1/TSC2, mTORC1 and PI3K on the Akt-T308 readout for the three hypotheses.

FIG. 24 shows the influence of perturbations of TSC1/TSC2, mTORC1, or PI3K on the phosphorylation of Akt-T308 for the three hypotheses. The three hypotheses did not show any difference in the dynamics of Akt-T308 phosphorylation when varying the amounts of PI3K and mTORC1. A small difference was observed for TSC1/TSC2 perturbation where the TSC1/TSC2-dependent hypothesis showed a slight increase in Akt-T308 phosphorylation when TSC1/TSC2 activity was reduced. In the TSC1/TSC2-dependent hypothesis, the mTORC2 activity is reduced when the amount of TSC1/TSC2 is reduced.

Figure 25:
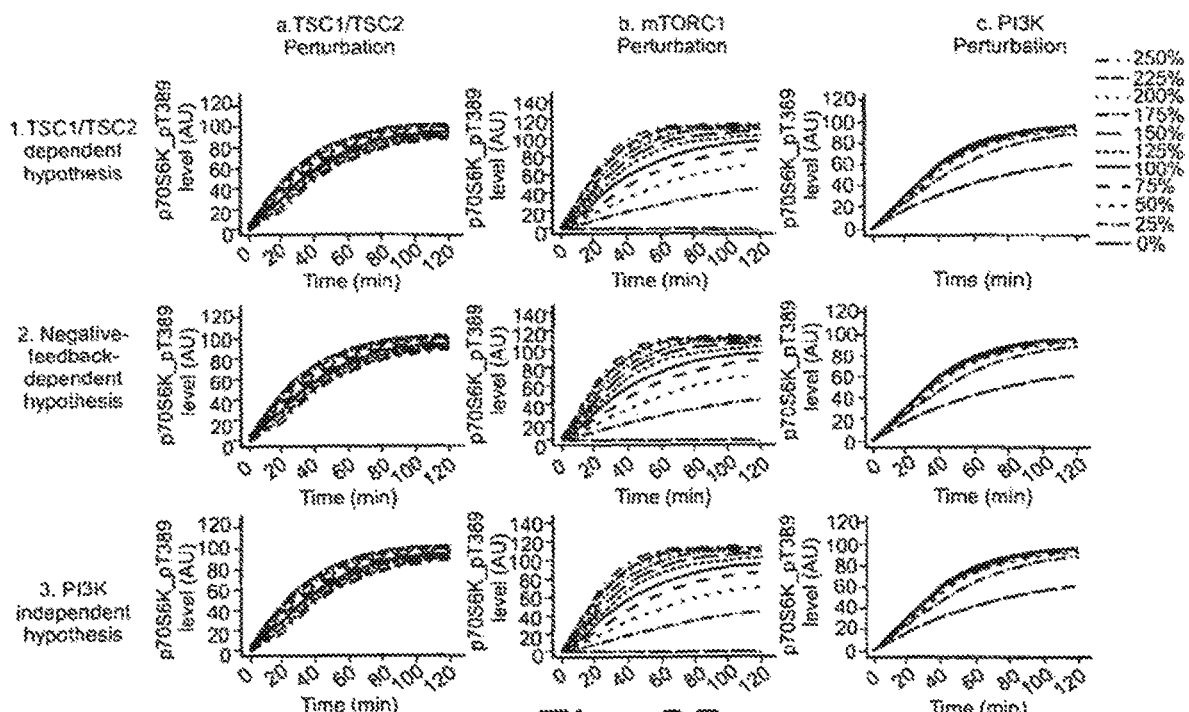
FIG. 25: The influence of perturbations of TSC1/TSC2, mTORC1 and PI3K on the p70-S6K-T389 readout for the three hypotheses.

FIG. 25 shows the influence of perturbations of TSC1/TSC2, mTORC1, or PI3K on the phosphorylation of p70-S6K-T389 for the three hypotheses. The effect of each perturbation on the networks representing each hypothesis for the phosphorylation of p70-S6K-T389, which is a readout for mTORC1 activity, is shown.

In FIGS. 26A-26B a simulation and perturbations for the new network structure based on Hypothesis 4: PI3K-dependent, NFL-independent regulation of mTORC2 is shown.

FIG. 26A shows a comparison between the simulated and experimental time courses for Hypothesis 4 shows that the simulated time courses match the experimental readouts.

FIG. 26B shows a the influence of perturbations of TSC1/TSC2, mTORC1, or PI3K on the dynamics of phosphorylation of Akt-T308 and p70-S6K-T389 for Hypothesis 4.

Figure 27:
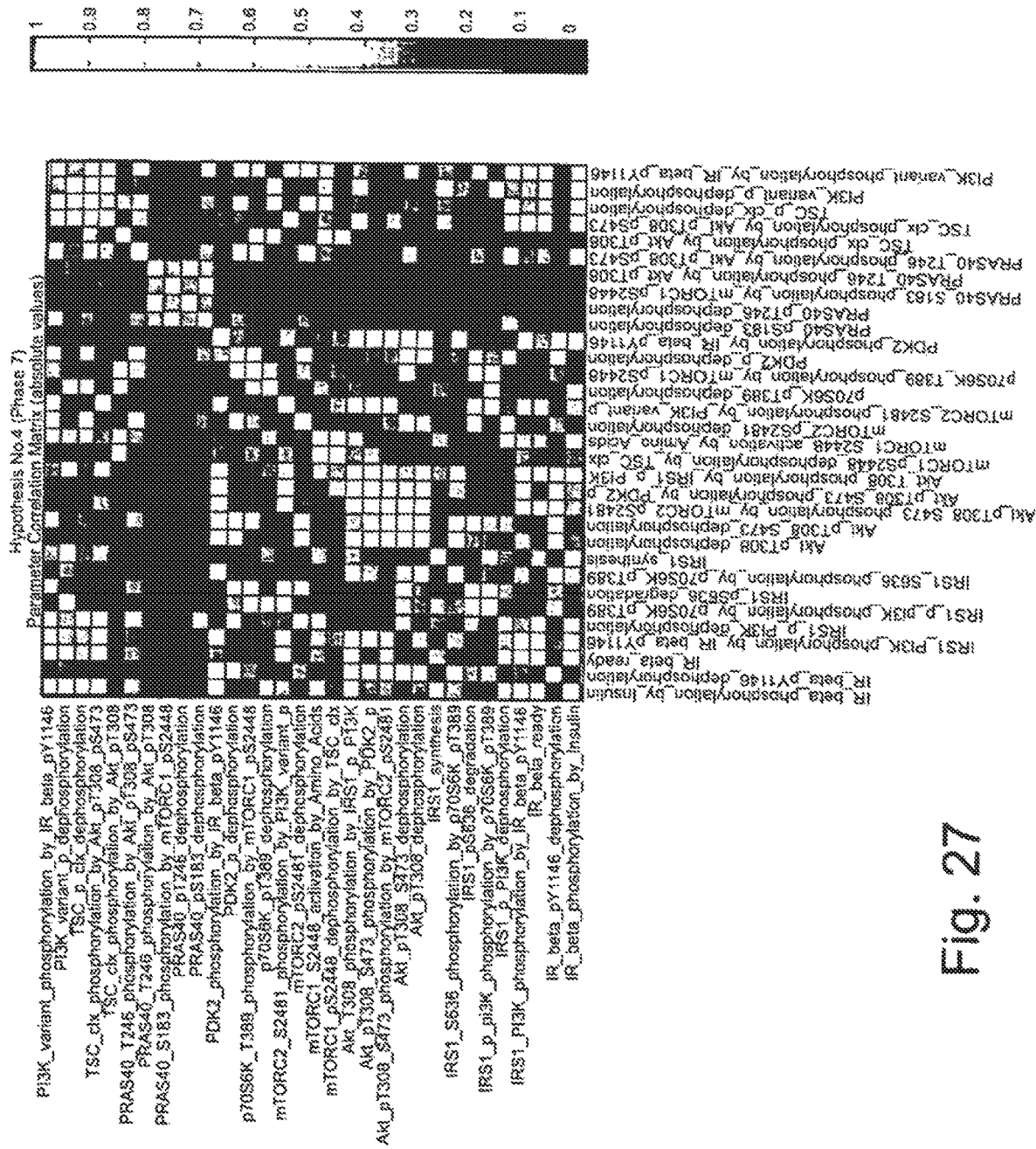
FIG. 27: Identifiability analysis for hypothesis No. 4.

FIG. 27 shows an identifiability analysis for Hypothesis 4: PI3K-dependent, NFL-independent regulation of mTORC2. Parameter correlation matrix for Hypothesis 4 is shown. See FIG. 15 for details.

Figure 28:
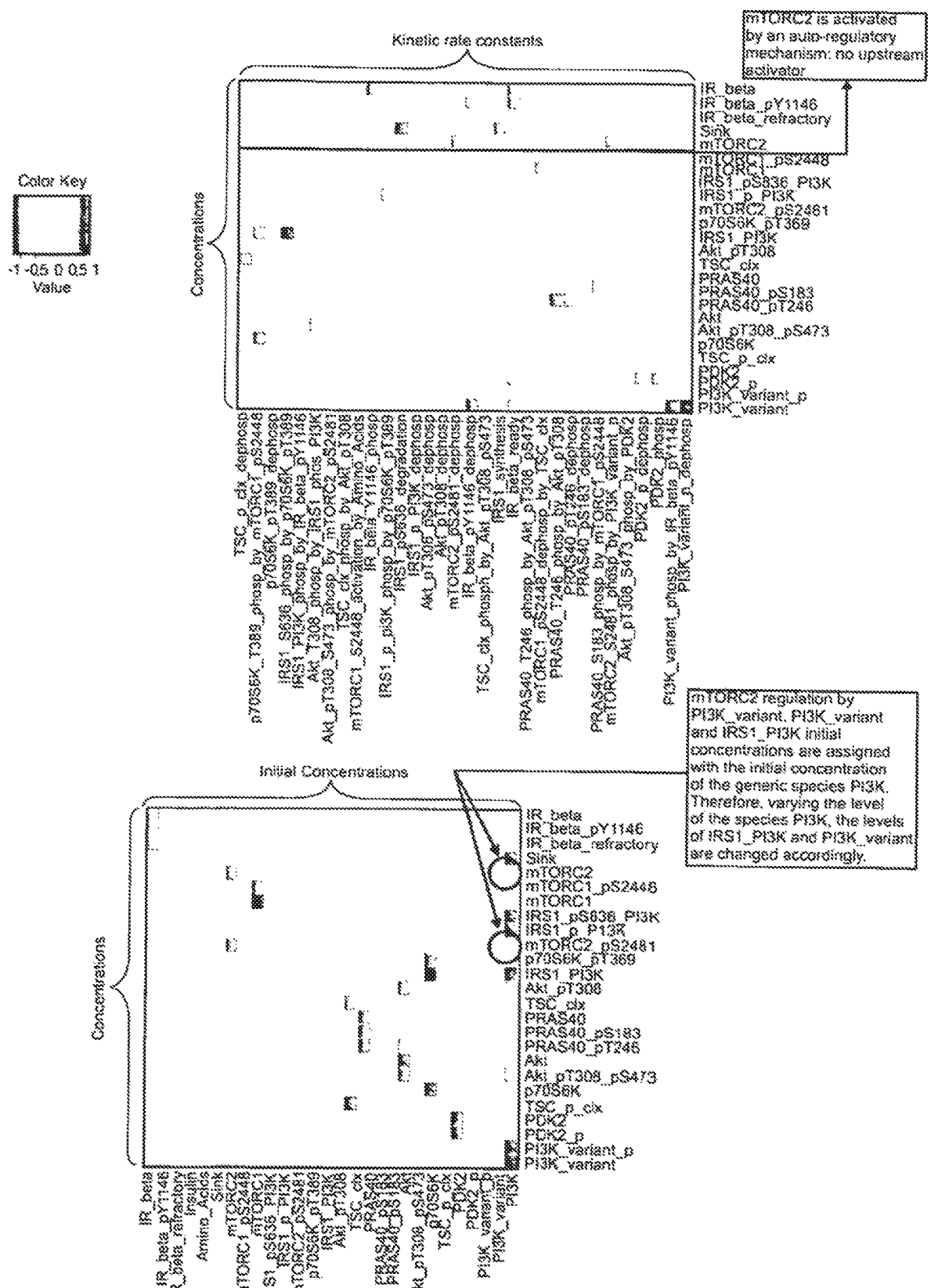
FIG. 28: Sensitivity analysis for hypothesis No. 4.

FIG. 28 shows a sensitivity analysis for Hypothesis 4: PI3K-dependent, NFL-independent regulation of mTORC2. Sensitivity analysis for the initial concentrations and the kinetic rates parameters for Hypothesis 4 is shown. See FIG. 16 for details of the top and bottom plots.

Figure 29:
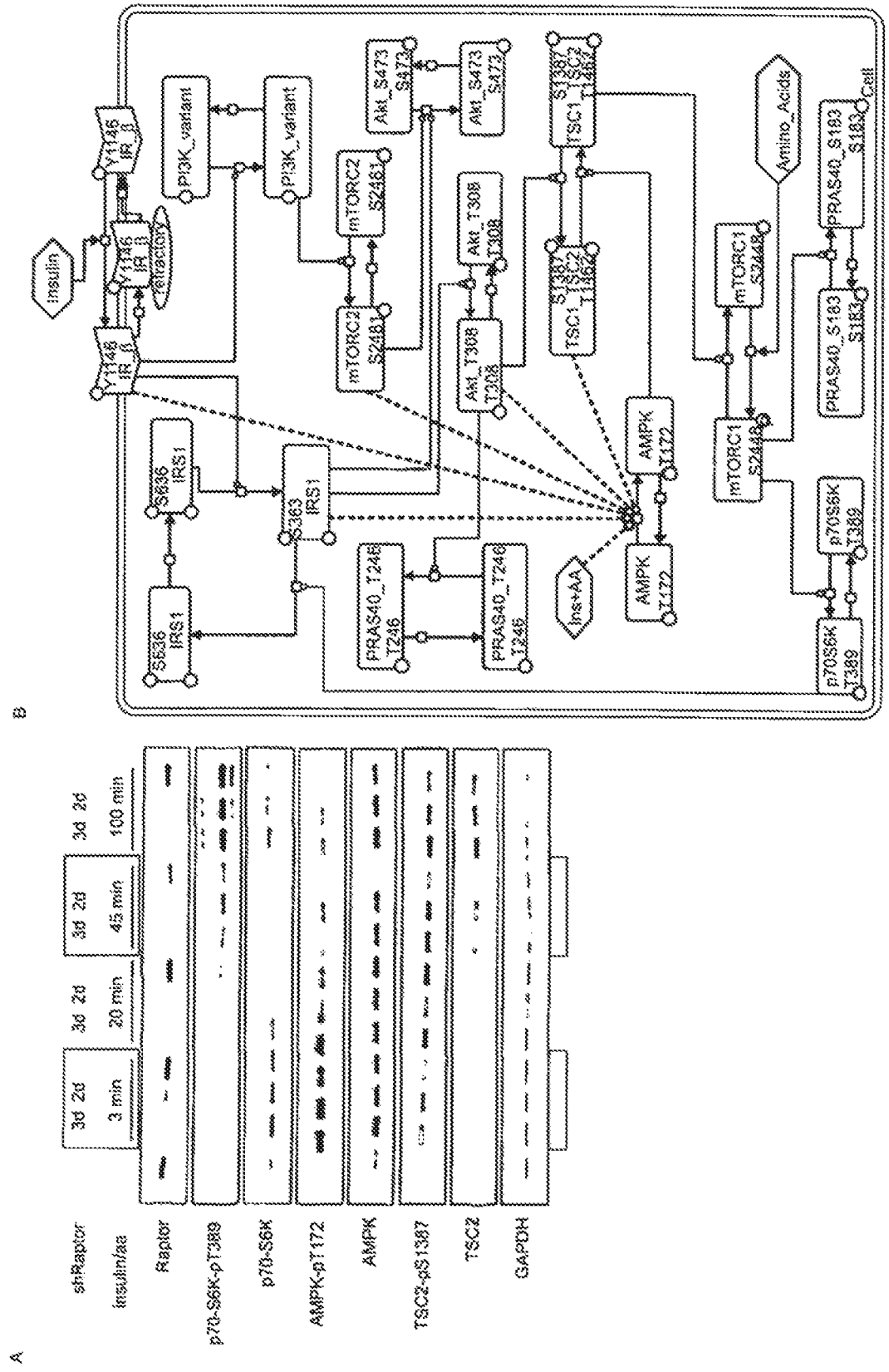
FIGS. 29A-29B: Setup of an AMPK module.

FIGS. 29A-29B show a setup of an AMPK module.

FIG. 29A shows AMPK is induced upon insulin induction. A gradual Raptor knock down was induced in HeLa cells by doxycyline treatment for the indicated times. Cells were serum/aa starved for 16 h and restimulated with aa and 100 nM insulin (ins) for 3, 20, 45, or 100 min.

FIG. 29B shows a graphical insulin-mTOR-AMPK model. This model integrates our previous insulin-mTOR model with AMPK regulation. Six hypotheses of AMPK activation are investigated (blue dotted lines). Except for the Insulin- and IR-beta-induced AMPK hypotheses, all the others implicitly assume AMPK being dependent on the p70-S6K-negative feedback loop.

FIGS. 30A-30B show an identifiability analysis for IRS1-induced AMPK model (hypothesis 3).

FIG. 30A shows a structural identifiability analysis was performed with the software GenSSI a priori. In the reduced identifiability tableau, blue circles indicate the parameters detected directly as structurally globally identifiable at the first order tableau, whereas magenta circles highlight the parameters detected as structurally globally identifiable at the second order tableau after computing the symbolic solution.

FIG. 30B shows a MOTA identifiability analysis was executed using the 50% of the best fits of the calibration fits sequence. A correlation among a set of parameters is indicated by the tuple of correlated parameters, their correlation coefficient (r2), coefficient of variation (CV) and the number of times this correlation is identified by varying the parameters of the tuple (#). Even though there are high correlations among some parameters, the corresponding coefficient of variation was lower than 0.002, which can be explained as numeric approximation error in the fit sequence calibration process. (*) r2>0.9 & CV>0.1 (**) r2>0.9 & CV>0.1 & #>1.

Figure 31:
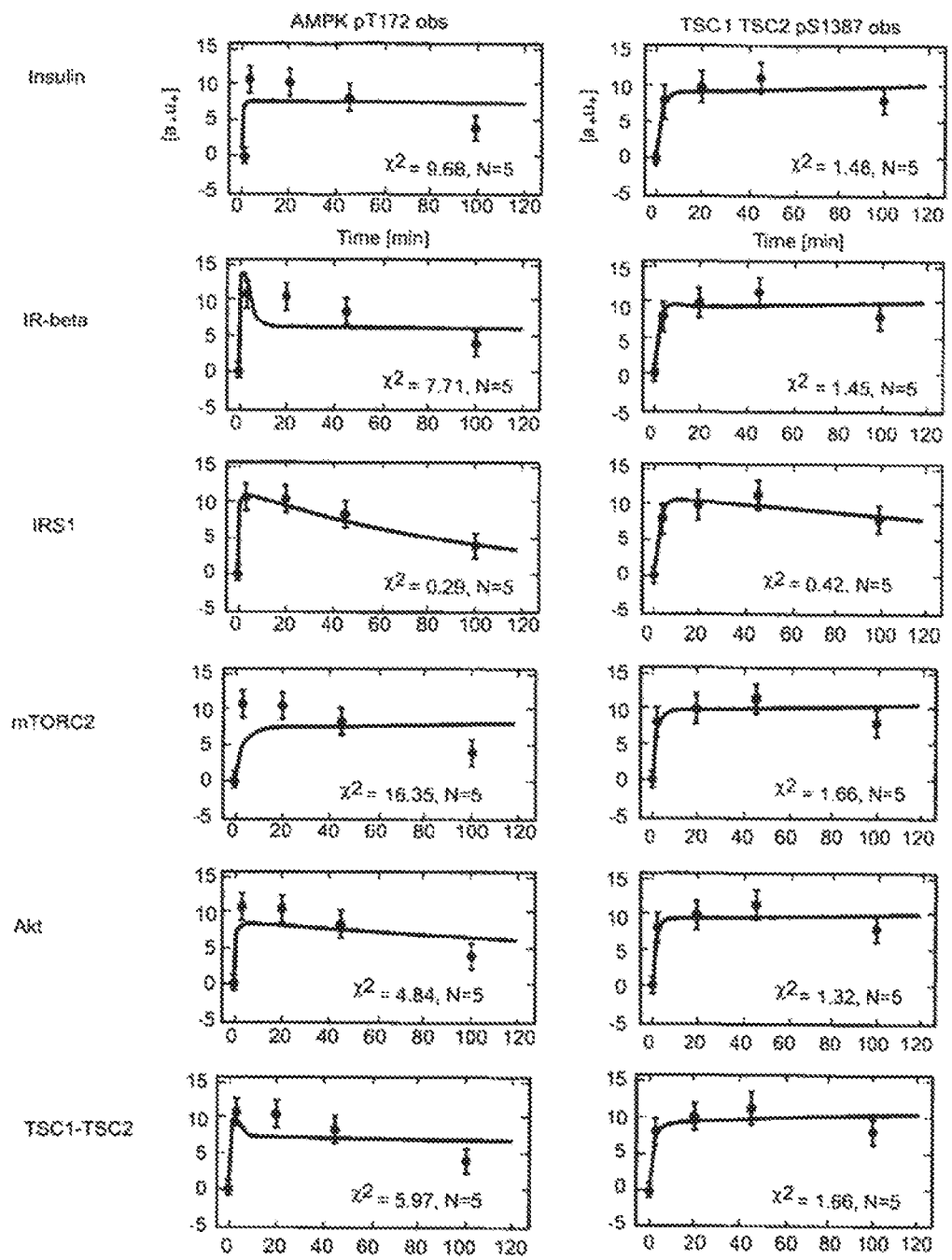
FIG. 31: Prediction: intersection of insulin and AMPK signalling at the level of IRS1.

FIG. 31 shows a prediction: intersection of insulin and AMPK signalling at the level of IRS1. Simulated time courses (red lines) versus experimental data (blue points) for AMPK-pT172 and TSC1-TSC2-pS1387 (columns) shown for the six hypotheses: Insulin-, IR-beta-, IRS-, mTORC2-, Akt-, TSC1-TSC2-induced AMPK (rows). These predictions suggest that AMPK could be regulated by kinases downstream of the insulin receptor. The IRS-induced AMPK model fitted our experimental data best. Experimental data error bars indicate standard error of the mean (SEM) calculated over 3 repetitions. The attached SBML model reproduces the AMPK induction by IRS1.

FIGS. 32A-32F show an experimental testing: IRS induces AMPK.

Figure 32:
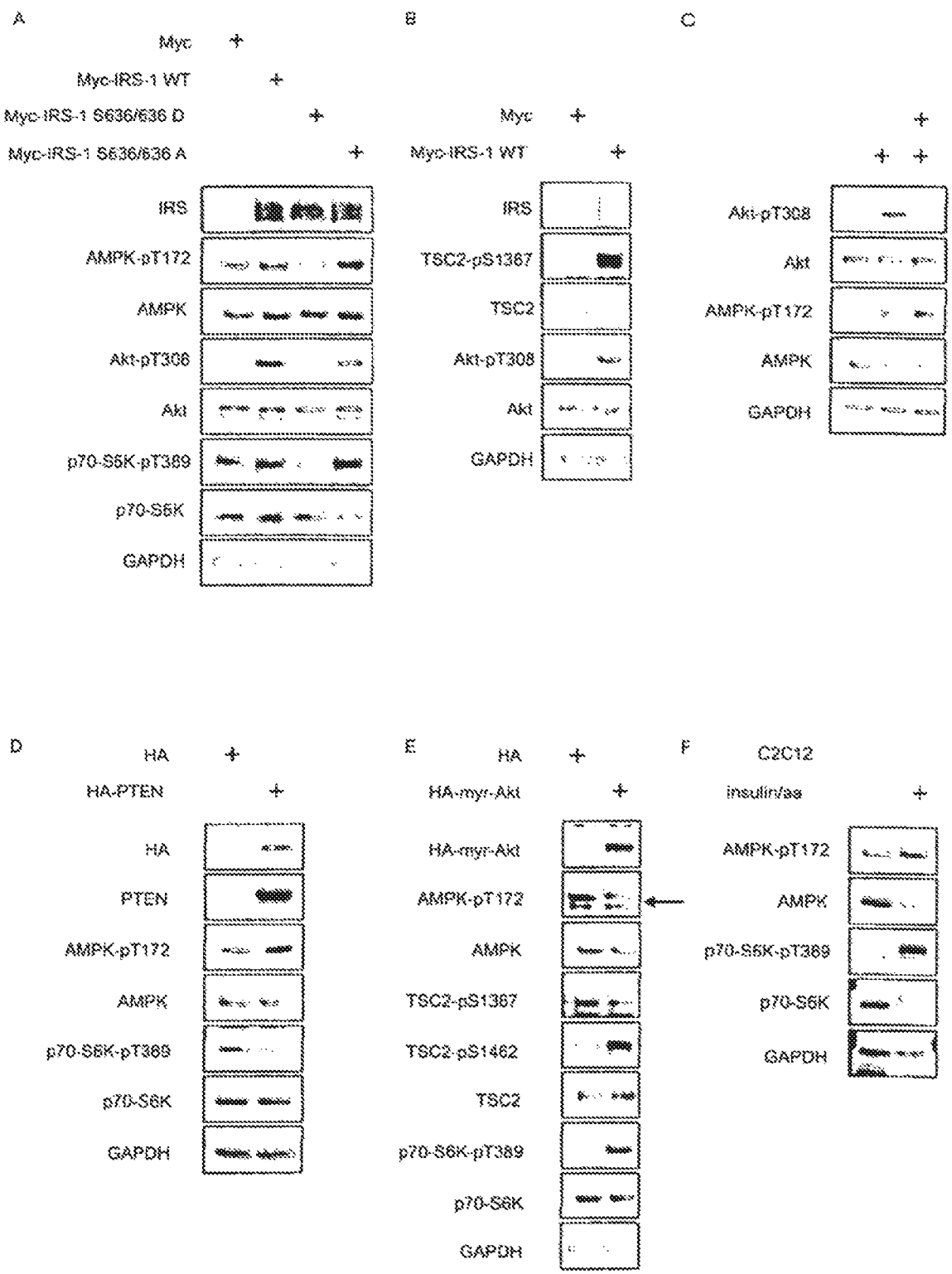
FIGS. 32A-32F: Experimental testing: IRS induces AMPK.

FIG. 32A shows an IRS overexpression induces AMPK. HeLa cells were harvested 24 h after transfection with the indicated IRS-1 constructs. The mutagenised Myc-IRS-1 S6367639 D construct mimics the constitutive phosphorylation by S6K, whereas Myc-IRS-1 S6367639 A resembles constitutively unphosphorylated IRS and cannot be inhibited by S6K and the NFL.

FIG. 32B shows an IRS overexpression induces TSC2 phosphorylation by AMPK. HeLa cells were harvested 24 h after transfection with Myc-IRS-1 WT.

FIG. 32C shows a PI3K inhibitor Wortmannin induces AMPK. HeLa cells were starved and treated with 100 nM Wortmannin or carrier prior to insulin/aa restimulation.

FIG. 32D shows an overexpression of the PI3K antagonist PTEN induces AMPK. HeLa cells were transfected 24 h prior to harvest. Cells were serum/aa starved prior to insulin/aa restimulation.

FIG. 32E shows a constitutively active Akt inhibits AMPK. HeLa cells were harvested 24 h after transfection with myristoylated Akt (HA-myr-Akt).

FIG. 32F shows Insulin/aa induces AMPK in LKB1 positive C2C12 myocytes.

FIGS. 33A-33B shoe a new model structure: IRS is required for AMPK induction by insulin.

FIG. 33A shows a schematic representation of the insulin induced mTORC1 pathway, including IRS dependent AMPK induction. Importantly, the negative feedback loop (NFL) via IRS targets not only PI3K but also AMPK. Wmn=Wortmannin.

FIG. 33B shows an Insulin-mTOR-AMPK model describing IRS as regulator of AMPK.

FIGS. 34A-34C show an identifiability and parameter estimation for the IR-beta-induced AMPK model (hypothesis No. 6).

FIG. 34A shows an identifiability analysis for the IR-beta-induced AMPK model indicated non identifiability issues for the parameters regulating AMPK dynamics (p7, p8).

FIG. 34B shows a correlation plot between the two parameters (p7, p8) confirms non-identifiability of the parameters.

FIG. 34C shows the first round of the parameter estimation reported a standard deviation percentage higher than 5% for the two parameters. P8 was further recalibrated in a second round in which it was correctly identified.

FIGS. 35A-35B show a sensitivity analysis for the IRS1-induced AMPK model (hypothesis No. 7).

FIG. 35A shows a 2-dimensional sensitivity analysis between the estimated kinetic rate constants versus the protein concentrations. The table shows that all the parameters are essential for describing the model and the IRS1-p regulation is the most important as it mediates the insulin signalling as well as the p70-S6K-negative feedback loop. Shading indicate sensitivity levels.

FIG. 35B shows a 3-dimensional sensitivity analysis as normalized in [0,1]. Shading different estimated kinetic rate constant parameters.

FIGS. 36A-36B show an additional simulated versus experimental time courses for IRS1-induced AMPK model (hypothesis No. 7).

FIG. 36A shows main data set used for parameter estimation. Simulated (red lines) versus experimental data (blue points) are plotted for nine wild type (WT) readouts along the insulin-TOR network upon insulin/aa induction.

FIG. 36B shows an additional data set used for parameter estimation. Experimental data for seven readouts for a Raptor knock down (KD) upon insulin/aa induction. Experimental mean+/−SEM calculated from four repetitions. Goodness-of-fit $\chi 2$ is reported for each plot along with the number of measured time points.

Figure 37:
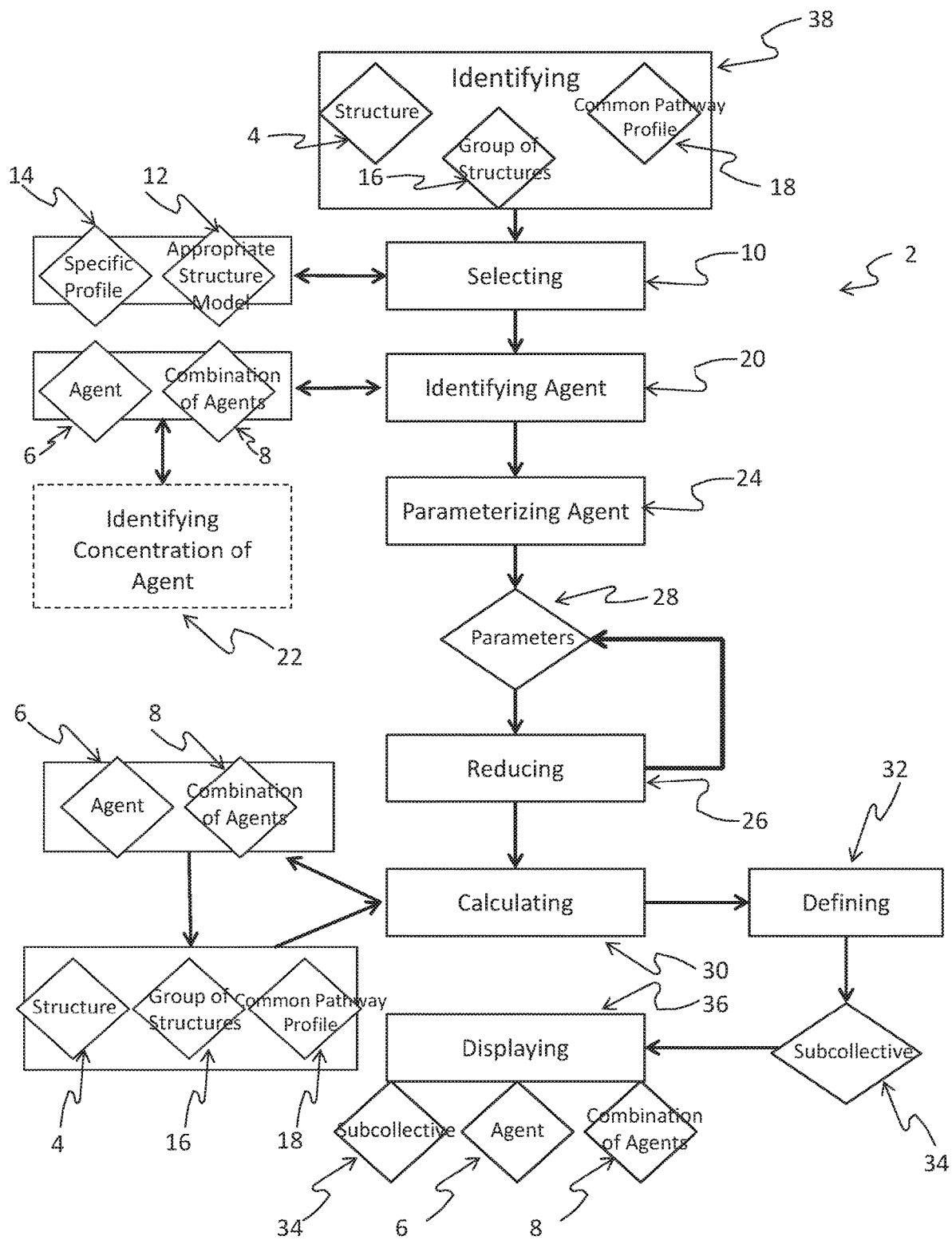
FIG. 37: a schematic view of a first embodiment of the model.

FIG. 37 shows a schematic view of a first embodiment of a method 2 for modelling, optimizing, parameterizing, testing and/or validating a dynamic network or network perturbations, for predicting the response of a structure 4 as a result of a perturbation, in particular to an agent 6 or a combination of agents 8, e.g. a kinase inhibitor/activator, and/or for predicting of effects of specific profiles, in particular mutational or metabolic or inhibitor/activator profiles on system behaviour, in particular cellular growth or clinical outcome.

The method 2 comprises a step of selecting 10 at least one appropriate structure model 12 or specific profile model 14 of the at least one structure 4, of a group of structures 16 and/or of the network profile 18.

Subsequently, a step of identifying 20 of the at least one agent 6 and/or at least one combination of agents 8 is realised. If it is necessary a step of identifying 22 the concentration of each agent 6 or of each combination of agents 8 can be applied.

After identifying 20 of the at least one agent 6 and/or the at least one combination of agents 8 a step of parameterization 24 of the at least one structure profile and/or of at least one combination of structure profiles is carried out, whereby the structure profile and/or the combination of structure profiles use at least a dynamic network model, in particular an insulin-TOR kinase model;

In a following step 26 the number of parameters 28, in particular the parameters 28 defined for 24 the at least one structure profile and/or the at least one combination of structure profiles of the dynamic network model to generate a reduced dynamic network model, is reduced;

After that a step of calculating 30 the reaction of each structure 4, of the group of structures 18 and/or of the network profile 20 caused by the agent 6 and/or combination of agents 8 is carried out.

Dependent from the calculated reaction of each structure 4, of the group of structures 18 and/or of the network profile 20 the next step 32 defines at least one subcollective 34 of pathway profiles of the structure, of the group of structures and/or of a common network profile characterised by reaction with the best outcome;

Finally the method 2 provides a step of displaying 36 at least the subcollective 34, the corresponding agent 6 and/or the combination of agents 8.

Prior to the step 10 of selecting, a step of identifying 38 at least one structure 4, one group of structures 16 and/or one network profile 18 can be carried out if necessary or advantageous, in particular by uploading from a database and/or by experimental determination. Table S1 shows an preferred ordinary differential equations of the general model and the models representing Hypothesis 1, 2, and 3 for mTORC2 activation. List of kinetic rate constants and ordinary differential equations (ODEs) for the general model. (A) and the Hypotheses 1, 2, and 3 (B). Each hypothesis is derived from the general model by replacing the mTORC2 ODEs, shown in the box, with those corresponding to the hypothesis.

Table S2 shows preferred parameter values of the general model. The general model was fully parameterized by three steps. Phase 1, three kinetic rate constants of the insulin receptor (IR-beta) were determined. Phase 2, the general model without PDK2 was obtained by parameterizing 24 kinetic rate constants. In this phase, Akt-S473 activation is modelled as autoregulation, independent of mTORC2 and PDK2. Phase 3, PDK2 dynamics were added to the system and the three parameters regulating Akt-S473 phosphorylation were calibrated by substituting the previously introduced autoregulatory mechanism (parameters values shown in red) of Akt. For each phase, 350 independent calibrations, starting from random initial configurations of the parameters, were executed and the best solution set fitting the data was selected. Phase 1 and 3 converged to a single solution set. Phase 2 converged to two solutions sets of which one was discarded as inconsistent with the experimental data (shown for phosphorylated Akt-S473 and IRS1-S636 readouts). For each phase, the mean and standard deviation of the estimated parameters were computed from the selected solution set. The solution closest to the centroid of the selected solution cluster was chosen for fixing the parameter values.

Table S3 shows preferred parameter values of Hypotheses 1, 2, and 3. For each hypothesis, the estimated parameters were calibrated using the same protocol provided in table S2. For each hypothesis, all the corresponding calibrations converged to a single solution set.

Table S4 shows a summary of model goodness-of-fit. The total chi-square and Akaike Information Criterion (AIC) measures are reported for the general model and the four hypotheses. Both the measures slightly penalize the TSC1/TSC2-dependent hypothesis. AIC also penalizes the PI3K-independent and the fourth hypotheses due to the higher number of parameters in these two models. However, these differences are not statistically significant for rejection of any model.

Table S5 shows a preferred parameter table for the IRS1-induced AMPK model (hypothesis 3).

The estimated kinetic rate constants together with the species concentrations are provided. The mean, standard deviations and percent of standard deviation over the mean, computed over the 50% of the best fits, are also indicated. These statistics shows that all the 24 estimated parameter could be fixed at the first round of calibration. Scaling factor parameters and observable variables are also indicated. The attached SBML model is configured with these parameter values.

Table S6 shows a Statistical ranking of the models according to the invention.

Quality of fitting measures were used to determine a ranking of the investigated models. IRS1-induced AMPK model showed the lowest $\chi 2$ value, indicating that this model was the most probable. AIC, AICc and BIC values are reported as additional measures.

The features of the present invention disclosed in the description above, in the claims and in the drawings can be used for implementing the invention in its different embodiments both individually and in every possible combination thereof.

REFERENTIAL NUMBERS

2 Method
4 Structure
6 Agent
8 Combination of agents
10 Step of selecting
12 Appropriate structure model
14 Specific profile
16 Group of structures
18 Common pathway profile
20 Step of identifying agent
22 Step of identifying concentration of agent
24 Step of parameterizing at least the agent
26 Step of reducing
28 Parameters
30 Step of calculating
32 Step of defining
34 Subcollective
36 Step of displaying
38 Step of identifying

ADDITIONAL REFERENCES

1. R. Zoncu, A. Efeyan, D. M. Sabatini, mTOR: from growth signal integration to cancer, diabetes and ageing. Nat Rev Mol Cell Biol 12, 21 (2011).
2. J. J. Howell, B. D. Manning, mTOR couples cellular nutrient sensing to organismal metabolic homeostasis. Trends Endocrinol Metab 22, 94 (2011).
3. C. Garcia-Echeverria, Blocking the mTOR pathway: a drug discovery perspective. Biochem Soc Trans 39, 451 (2011).

4. P. Polak, M. N. Hall, mTOR and the control of whole body metabolism. Curr Opin Cell Biol 21, 209 (2009).
5. N. Cybulski, M. N. Hall, TOR complex 2: a signaling pathway of its own. Trends Biochem Sci 34, 620 (2009).
6. M. E. Feldman, K. M. Shokat, New inhibitors of the PI3K-Akt-mTOR pathway: insights into mTOR signaling from a new generation of Tor Kinase Domain Inhibitors (TORKinibs). Curr Top Microbiol Immunol 347, 241 (2010).
7. S. Sengupta, T. R. Peterson, D. M. Sabatini, Regulation of the mTOR complex 1 pathway by nutrients, growth factors, and stress. Mol Cell 40, 310 (2010).
8. Y. Sancak, L. Bar-Peled, R. Zoncu, A. L. Markhard, S. Nada, D. M. Sabatini, Ragulator-Rag complex targets mTORC1 to the lysosomal surface and is necessary for its activation by amino acids. Cell 141, 290 (2010).
9. Y. Sancak, D. M. Sabatini, Rag proteins regulate amino-acid-induced mTORC1 signalling. Biochem Soc Trans 37, 289 (2009).
10. J. Avruch, X. Long, Y. Lin, S. Ortiz-Vega, J. Rapley, A. Papageorgiou, N. Oshiro, U. Kikkawa, Activation of mTORC1 in two steps: Rheb-GTP activation of catalytic function and increased binding of substrates to raptor. Biochem Soc Trans 37, 223 (2009).
11. K. Thedieck, M. N. Hall, in The Handbook of Cell Signaling, R. B. a. E. Dennis, Ed. (2009), vol. 3, chap. 274, pp. 2285-2293.
12. E. Vander Haar, S. I. Lee, S. Bandhakavi, T. J. Griffin, D. H. Kim, Insulin signalling to mTOR mediated by the Akt/PKB substrate PRAS40. Nat. Cell Biol. 9, 316 (2007).
13. K. Thedieck, P. Polak, M. L. Kim, K. D. Molle, A. Cohen, P. Jeno, C. Arrieumerlou, M. N. Hall, PRAS40 and PRR5-like protein are new mTOR interactors that regulate apoptosis. PLoS One 2, e1217 (2007).
14. Y. Sancak, C. C. Thoreen, T. R. Peterson, R. A. Lindquist, S. A. Kang, E. Spooner, S. A. Carr, D. M. Sabatini, PRAS40 is an insulin-regulated inhibitor of the mTORC1 protein kinase. Mol. Cell 25, 903 (2007).
15. L. Wang, T. E. Harris, R. A. Roth, J. C. Lawrence, Jr., PRAS40 regulates mTORC1 kinase activity by functioning as a direct inhibitor of substrate binding. J. Biol. Chem. 282, 20036 (2007).
16. B. D. Fonseca, E. M. Smith, V. H. Lee, C. MacKintosh, C. G. Proud, PRAS40 is a target for mammalian target of rapamycin complex 1 and is required for signaling downstream of this complex. J Biol Chem 282, 24514 (2007).
17. N. Oshiro, R. Takahashi, K. Yoshino, K. Tanimura, A. Nakashima, S. Eguchi, T. Miyamoto, K. Hara, K. Takehana, J. Avruch, U. Kikkawa, K. Yonezawa, The proline-rich Akt substrate of 40 kDa (PRAS40) is a physiological substrate of mammalian target of rapamycin complex 1. J. Biol. Chem. 282, 20329 (2007).
18. L. Wang, T. E. Harris, J. C. Lawrence, Jr., Regulation of proline-rich Akt substrate of 40 kDa (PRAS40) function by mammalian target of rapamycin complex 1 (mTORC1)-mediated phosphorylation. J Biol Chem 283, 15619 (2008).
19. E. Jacinto, R. Loewith, A. Schmidt, S. Lin, M. A. Ruegg, A. Hall, M. N. Hall, Mammalian TOR complex 2 controls the actin cytoskeleton and is rapamycin insensitive. Nat. Cell Biol 6, 1122 (2004).
20. I. Tato, R. Bartrons, F. Ventura, J. L. Rosa, Amino acids activate mammalian target of rapamycin complex 2 (mTORC2) via PI3K/Akt signaling. J Biol Chem 286, 6128 (2011).
21. D. D. Sarbassov, D. A. Guertin, S. M. Ali, D. M. Sabatini, Phosphorylation and regulation of Akt/PKB by the rictor-mTOR complex. Science 307, 1098 (2005).
22. E. Jacinto, V. Facchinetti, D. Liu, N. Soto, S. Wei, S. Y. Jung, Q. Huang, J. Qin, B. Su, SIN1/MIP1 maintains rictor-mTOR complex integrity and regulates Akt phosphorylation and substrate specificity. Cell 127, 125 (2006).
23. C. Shiota, J. T. Woo, J. Lindner, K. D. Shelton, M. A. Magnuson, Multiallelic disruption of the rictor gene in mice reveals that mTOR complex 2 is essential for fetal growth and viability. Dev Cell 11, 583 (2006).
24. R. C. Hresko, M. Mueckler, mTOR.RICTOR is the Ser473 kinase for Akt/protein kinase B in 3T3-L1 adipocytes. J Biol Chem 280, 40406 (2005).
25. J. M. Garcia-Martinez, D. R. Alessi, mTOR complex 2 (mTORC2) controls hydrophobic motif phosphorylation and activation of serum- and glucocorticoid-induced protein kinase 1 (SGK1). Biochem J 416, 375 (2008).
26. D. D. Sarbassov, S. M. Ali, D. H. Kim, D. A. Guertin, R. R. Latek, H. Erdjument-Bromage, P. Tempst, D. M. Sabatini, Rictor, a novel binding partner of mTOR, defines a rapamycin-insensitive and raptor-independent pathway that regulates the cytoskeleton. Curr. Biol 14, 1296 (2004).
27. L. R. Pearce, D. Komander, D. R. Alessi, The nuts and bolts of AGC protein kinases. Nat Rev Mol Cell Biol 11, 9 (2010).
28. E. Jacinto, A. Lorberg, TOR regulation of AGC kinases in yeast and mammals. Biochem J 410, 19 (2008).
29. E. Fayard, G. Xue, A. Parcellier, L. Bozulic, B. A. Hemmings, Protein kinase B (PKB/Akt), a key mediator of the PI3K signaling pathway. Curr Top Microbiol Immunol 346, 31 (2010).
30. K. Inoki, M. N. Corradetti, K. L. Guan, Dysregulation of the TSC-mTOR pathway in human disease. Nat. Genet. 37, 19 (2005).
31. J. Huang, C. C. Dibble, M. Matsuzaki, B. D. Manning, The TSC1-TSC2 complex is required for proper activation of mTOR complex 2. Mol Cell Biol 28, 4104 (2008).
32. J. Huang, B. D. Manning, A complex interplay between Akt, TSC2 and the two mTOR complexes. Biochem Soc Trans 37, 217 (2009).
33. J. Huang, S. Wu, C. L. Wu, B. D. Manning, Signaling events downstream of mammalian target of rapamycin complex 2 are attenuated in cells and tumors deficient for the tuberous sclerosis complex tumor suppressors. Cancer Res 69, 6107 (2009).
34. W. van Veelen, S. E. Korsse, L. van de Laar, M. P. Peppelenbosch, The long and winding road to rational treatment of cancer associated with LKB1/AMPK/TSC/mTORC1 signaling. Oncogene, (2011).
35. Q. Yang, K. Inoki, E. Kim, K. L. Guan, TSC1/TSC2 and Rheb have different effects on TORC1 and TORC2 activity. Proc Natl Acad Sci USA 103, 6811 (2006).
36. E. A. Goncharova, D. A. Goncharov, H. Li, W. Pimtong, S. Lu, I. Khavin, V. P. Krymskaya, mTORC2 is Required for Proliferation and Survival of TSC2-Null Cells. Mol Cell Biol, (2011).
37. Y. Kamimura, Y. Xiong, P. A. Iglesias, O. Hoeller, P. Bolourani, P. N. Devreotes, PIP3-independent activation of TorC2 and PKB at the cell's leading edge mediates chemotaxis. Curr Biol 18, 1034 (2008).
38. S. Lee, Z. Shen, D. N. Robinson, S. Briggs, R. A. Firtel, Involvement of the cytoskeleton in controlling leading-edge function during chemotaxis. Mol Biol Cell 21, 1810 (2010).

39. P. G. Charest, Z. Shen, A. Lakoduk, A. T. Sasaki, S. P. Briggs, R. A. Firtel, A Ras signaling complex controls the RasC-TORC2 pathway and directed cell migration. Dev Cell 18, 737 (2010).
40. H. Cai, S. Das, Y. Kamimura, Y. Long, C. A. Parent, P. N. Devreotes, Ras-mediated activation of the TORC2-PKB pathway is critical for chemotaxis. J Cell Biol 190, 233 (2010).
41. G. S. Worthen, N. Avdi, A. M. Buhl, N. Suzuki, G. L. Johnson, FMLP activates Ras and Raf in human neutrophils. Potential role in activation of MAP kinase. J Clin Invest 94, 815 (1994).
42. L. Zheng, J. Eckerdal, I. Dimitrijevic, T. Andersson, Chemotactic peptide-induced activation of Ras in human neutrophils is associated with inhibition of p120-GAP activity. J Biol Chem 272, 23448 (1997).
43. Y. Kamada, Y. Fujioka, N. N. Suzuki, F. Inagaki, S. Wullschleger, R. Loewith, M. N. Hall, Y. Ohsumi, Tor2 directly phosphorylates the AGC kinase Ypk2 to regulate actin polarization. Mol Cell Biol 25, 7239 (2005).
44. E. Caron, S. Ghosh, Y. Matsuoka, D. Ashton-Beaucage, M. Therrien, S. Lemieux, C. Perreault, P. P. Roux, H. Kitano, A comprehensive map of the mTOR signaling network. Mol Syst Biol 6, 453 (2010).
45. A. R. Sedaghat, A. Sherman, M. J. Quon, A mathematical model of metabolic insulin signaling pathways. Am J Physiol Endocrinol Metab 283, E1084 (2002).
46. G. Wang, G. R. Krueger, Computational analysis of mTOR signaling pathway: bifurcation, carcinogenesis, and drug discovery. Anticancer Res 30, 2683 (2010).
47. P. K. Vinod, K. V. Venkatesh, Quantification of the effect of amino acids on an integrated mTOR and insulin signaling pathway. Mol Biosyst 5, 1163 (2009).
48. P. Jain, U.S. Bhalla, Signaling logic of activity-triggered dendritic protein synthesis: an mTOR gate but not a feedback switch. PLoS Comput Biol 5, e1000287 (2009).
49. G. R. Smith, D. P. Shanley, Modelling the Response of FOXO Transcription Factors to Multiple Post-Translational Modifications Made by Ageing-Related Signalling Pathways. PLoS One 5, e11092 (2010).
50. C. Brannmark, R. Palmer, S. T. Glad, G. Cedersund, P. Stralfors, Mass. and information feedbacks through receptor endocytosis govern insulin signaling as revealed using a parameter-free modeling framework. J Biol Chem 285, 20171 (2010).
51. D. Ruths, M. Muller, J. T. Tseng, L. Nakhleh, P. T. Ram, The signaling petri net-based simulator: a non-parametric strategy for characterizing the dynamics of cell-specific signaling networks. PLoS Comput Biol 4, e1000005 (2008).
52. N. Borisov, E. Aksamitiene, A. Kiyatkin, S. Legewie, J. Berkhout, T. Maiwald, N. P. Kaimachnikov, J. Timmer, J. B. Hoek, B. N. Kholodenko, Systems-level interactions between insulin-EGF networks amplify mitogenic signaling. Mol Syst Biol 5, 256 (2009).
53. G. Cedersund, J. Roll, E. Ulfhielm, A. Danielsson, H. Tidefelt, P. Stralfors, Model-based hypothesis testing of key mechanisms in initial phase of insulin signaling. PLoS Comput Biol 4, e1000096 (2008).
54. V. V. Kiselyov, S. Versteyhe, L. Gauguin, P. De Meyts, Harmonic oscillator model of the insulin and IGF1 receptors' allosteric binding and activation. Mol Syst Biol 5, 243 (2009).
55. D. Faratian, A. Goltsov, G. Lebedeva, A. Sorokin, S. Moodie, P. Mullen, C. Kay, I. H. Um, S. Langdon, I. Goryanin, D. J. Harrison, Systems biology reveals new strategies for personalizing cancer medicine and confirms the role of PTEN in resistance to trastuzumab. Cancer Res 69, 6713 (2009).
56. L. Kuepfer, M. Peter, U. Sauer, J. Stelling, Ensemble modeling for analysis of cell signaling dynamics. Nat Biotechnol 25, 1001 (2007).
57. S. Nelander, W. Wang, B. Nilsson, Q. B. She, C. Pratilas, N. Rosen, P. Gennemark, C. Sander, Models from experiments: combinatorial drug perturbations of cancer cells. Mol Syst Biol 4, 216 (2008).
58. J. A. Papin, T. Hunter, B. O. Palsson, S. Subramaniam, Reconstruction of cellular signalling networks and analysis of their properties. Nat Rev Mol Cell Biol 6, 99 (2005).
59. N. Le Novere, M. Hucka, H. Mi, S. Moodie, F. Schreiber, A. Sorokin, E. Demir, K. Wegner, M. I. Aladjem, S. M. Wimalaratne, F. T. Bergman, R. Gauges, P. Ghazal, H. Kawaji, L. Li, Y. Matsuoka, A. Villeger, S. E. Boyd, L. Calzone, M. Courtot, U. Dogrusoz, T. C. Freeman, A. Funahashi, S. Ghosh, A. Jouraku, S. Kim, F. Kolpakov, A. Luna, S. Sahle, E. Schmidt, S. Watterson, G. Wu, I. Goryanin, D. B. Kell, C. Sander, H. Sauro, J. L. Snoep, K. Kohn, H. Kitano, The Systems Biology Graphical Notation. Nat Biotechnol 27, 735 (2009).
60. M. A. Bruhn, R. B. Pearson, R. D. Hannan, K. E. Sheppard, Second AKT: the rise of SGK in cancer signalling. Growth Factors 28, 394 (2010).
61. R. T. Peterson, P. A. Beal, M. J. Comb, S. L. Schreiber, FKBP12-rapamycin-associated protein (FRAP) autophosphorylates at serine 2481 under translationally repressive conditions. J Biol Chem 275, 7416 (2000).
62. H. A. Acosta-Jaquez, J. A. Keller, K. G. Foster, B. Ekim, G. A. Soliman, E. P. Feener, B. A. Ballif, D.C. Fingar, Site-specific mTOR phosphorylation promotes mTORC1-mediated signaling and cell growth. Mol Cell Biol 29, 4308 (2009).
63. J. Copp, G. Manning, T. Hunter, TORC-specific phosphorylation of mammalian target of rapamycin (mTOR): phospho-Ser2481 is a marker for intact mTOR signaling complex 2. Cancer Res 69, 1821 (2009).
64. G. A. Soliman, H. A. Acosta-Jaquez, E. A. Dunlop, B. Ekim, N. E. Maj, A. R. Tee, D.C. Fingar, mTOR Ser-2481 autophosphorylation monitors mTORC-specific catalytic activity and clarifies rapamycin mechanism of action. J Biol Chem 285, 7866 (2010).
65. M. E. Feldman, B. Apsel, A. Uotila, R. Loewith, Z. A. Knight, D. Ruggero, K. M. Shokat, Active-site inhibitors of mTOR target rapamycin-resistant outputs of mTORC1 and mTORC2. PLoS Biol 7, e38 (2009).
66. C. C. Thoreen, S. A. Kang, J. W. Chang, Q. Liu, J. Zhang, Y. Gao, L. J. Reichling, T. Sim, D. M. Sabatini, N. S. Gray, An ATP-competitive mammalian target of rapamycin inhibitor reveals rapamycin-resistant functions of mTORC1. J Biol Chem 284, 8023 (2009).
67. C. C. Thoreen, D. M. Sabatini, Rapamycin inhibits mTORC1, but not completely. Autophagy 5, 725 (2009).
68. F. Heidebrecht, A. Heidebrecht, I. Schulz, S. E. Behrens, A. Bader, Improved semiquantitative Western blot technique with increased quantification range. J Immunol Methods 345, 40 (2009).
69. W. W. Chen, M. Niepel, P. K. Sorger, Classic and contemporary approaches to modeling biochemical reactions. Genes Dev 24, 1861 (2010).
70. C. G. Moles, P. Mendes, J. R. Banga, Parameter estimation in biochemical pathways: a comparison of global optimization methods. Genome Res 13, 2467 (2003).

71. C. Zhan, L. F. Yeung, Parameter estimation in systems biology models using spline approximation. BMC Syst Biol 5, 14 (2011).
72. R. D. Polakiewicz, S. M. Schieferl, A. C. Gingras, N. Sonenberg, M. J. Comb, mu-Opioid receptor activates signaling pathways implicated in cell survival and translational control. J Biol Chem 273, 23534 (1998).
73. A. D. Kohn, F. Takeuchi, R. A. Roth, Akt, a pleckstrin homology domain containing kinase, is activated primarily by phosphorylation. J Biol Chem 271, 21920 (1996).
74. B. N. Kholodenko, Cell-signalling dynamics in time and space. Nat Rev Mol Cell Biol 7, 165 (2006).
75. G. von Dassow, E. Meir, E. M. Munro, G. M. Odell, The segment polarity network is a robust developmental module. Nature 406, 188 (2000).
76. T.-R. Xu, V. Vyshemirsky, A. Gormand, A. von Kriegsheim, M. Girolami, G. S. Baillie, D. Ketley, A. J. Dunlop, G. Milligan, M. D. Houslay, W. Kolch, Inferring Signaling Pathway Topologies from Multiple Perturbation Measurements of Specific Biochemical Species. Sci. Signal. 3, ra20 (2010).
77. L. Bozulic, B. Surucu, D. Hynx, B. A. Hemmings, PKBalpha/Akt1 acts downstream of DNA-PK in the DNA double-strand break response and promotes survival. Mol Cell 30, 203 (2008).
78. J. Feng, J. Park, P. Cron, D. Hess, B. A. Hemmings, Identification of a PKB/Akt hydrophobic motif Ser-473 kinase as DNA-dependent protein kinase. J Biol Chem 279, 41189 (2004).
79. A. A. Troussard, N. M. Mawji, C. Ong, A. Mui, R. St-Arnaud, S. Dedhar, Conditional knock-out of integrin-linked kinase demonstrates an essential role in protein kinase B/Akt activation. J Biol Chem 278, 22374 (2003).
80. J. G. Viniegra, N. Martinez, P. Modirassari, J. H. Losa, C. Parada Cobo, V. J. Lobo, C. I. Luquero, L. Alvarez-Vallina, S. Ramon y Cajal, J. M. Rojas, R. Sanchez-Prieto, Full activation of PKB/Akt in response to insulin or ionizing radiation is mediated through ATM. J Biol Chem 280, 4029 (2005).
81. M. J. Rane, P. Y. Coxon, D. W. Powell, R. Webster, J. B. Klein, W. Pierce, P. Ping, K. R. McLeish, p38 Kinase-dependent MAPKAPK-2 activation functions as 3-phosphoinositide-dependent kinase-2 for Akt in human neutrophils. J Biol Chem 276, 3517 (2001).
82. Y. Kawakami, H. Nishimoto, J. Kitaura, M. Maeda-Yamamoto, R. M. Kato, D. R. Littman, M. Leitges, D. J. Rawlings, T. Kawakami, Protein kinase C betaII regulates Akt phosphorylation on Ser-473 in a cell type- and stimulus-specific fashion. J Biol Chem 279, 47720 (2004).
83. C. Partovian, M. Simons, Regulation of protein kinase B/Akt activity and Ser473 phosphorylation by protein kinase Calpha in endothelial cells. Cell Signal 16, 951 (2004).
84. K. Mao, S. Kobayashi, Z. M. Jaffer, Y. Huang, P. Volden, J. Chernoff, Q. Liang, Regulation of Akt/PKB activity by P21-activated kinase in cardiomyocytes. J Mol Cell Cardiol 44, 429 (2008).
85. A. Toker, A. C. Newton, Akt/protein kinase B is regulated by autophosphorylation at the hypothetical PDK-2 site. J Biol Chem 275, 8271 (2000).
86. Y. Yu, S. O. Yoon, G. Poulogiannis, Q. Yang, X. M. Ma, J. Villen, N. Kubica, G. R. Hoffman, L. C. Cantley, S. P. Gygi, J. Blenis, Phosphoproteomic analysis identifies Grb10 as an mTORC1 substrate that negatively regulates insulin signaling. Science 332, 1322 (2011).
87. P. P. Hsu, S. A. Kang, J. Rameseder, Y. Zhang, K. A. Ottina, D. Lim, T. R. Peterson, Y. Choi, N. S. Gray, M. B. Yaffe, J. A. Marto, D. M. Sabatini, The mTOR-regulated phosphoproteome reveals a mechanism of mTORC1-mediated inhibition of growth factor signaling. Science 332, 1317 (2011).
88. G. J. Brunn, J. Williams, C. Sabers, G. Wiederrecht, J. C. Lawrence, Jr., R. T. Abraham, Direct inhibition of the signaling functions of the mammalian target of rapamycin by the phosphoinositide 3-kinase inhibitors, wortmannin and LY294002. EMBO J 15, 5256 (1996).
89. M. R. Williams, J. S. Arthur, A. Balendran, J. van der Kaay, V. Poli, P. Cohen, D. R. Alessi, The role of 3-phosphoinositide-dependent protein kinase 1 in activating AGC kinases defined in embryonic stem cells. Curr Biol 10, 439 (2000).
90. M. G. Myers, Jr., T. C. Grammer, L. M. Wang, X. J. Sun, J. H. Pierce, J. Blenis, M. F. White, Insulin receptor substrate-1 mediates phosphatidylinositol 3'-kinase and p70S6k signaling during insulin, insulin-like growth factor-1, and interleukin-4 stimulation. J Biol Chem 269, 28783 (1994).
91. F. Peruzzi, M. Prisco, M. Dews, P. Salomoni, E. Grassilli, G. Romano, B. Calabretta, R. Baserga, Multiple signaling pathways of the insulin-like growth factor 1 receptor in protection from apoptosis. Mol Cell Biol 19, 7203 (1999).
92. D. J. Van Horn, M. G. Myers, Jr., J. M. Backer, Direct activation of the phosphatidylinositol 3'-kinase by the insulin receptor. J Biol Chem 269, 29 (1994).
93. B. Vanhaesebroeck, J. Guillermet-Guibert, M. Graupera, B. Bilanges, The emerging mechanisms of isoform-specific PI3K signalling. Nat Rev Mol Cell Biol 11, 329 (2010).
94. X. Gan, J. Wang, B. Su, D. Wu, Evidence for Direct Activation of mTORC2 Kinase Activity by Phosphatidylinositol 3,4,5-Trisphosphate. J Biol Chem 286, 10998 (2011).
95. V. Zinzalla, D. Stracka, W. Oppliger, M. N. Hall, Activation of mTORC2 by association with the ribosome. Cell 144, 757 (2011).
96. M. Wiznerowicz, D. Trono, Conditional suppression of cellular genes: lentivirus vector-mediated drug-inducible RNA interference. J Virol 77, 8957 (2003).
97. A. Funahashi, M. Morohashi, H. Kitano, N. Tanimura, CellDesigner: a process diagram editor for gene-regulatory and biochemical networks. BIOSILICO 1, 159 (2003).
98. S. Hoops, S. Sahle, R. Gauges, C. Lee, J. Pahle, N. Simus, M. Singhal, L. Xu, P. Mendes, U. Kummer, COPASI—a COmplex PAthway SImulator. Bioinformatics 22, 3067 (2006).
99. A. Corana, M. Marchesi, C. Martini, S. Ridella, Minimizing multimodal functions of continuous variables with the "simulated annealing" algorithm. ACM Trans. Math. Softw. 13, 262 (1987).
100. S. Kirkpatrick, C. D. Gelatt, Jr., M. P. Vecchi, Optimization by simulated annealing. Science 220, 671 (1983).
101. H. Schmidt, M. Jirstrand, Systems Biology Toolbox for MATLAB: a computational platform for research in systems biology. Bioinformatics 22, 514 (2006).
102. S. M. Keating, B. J. Bornstein, A. Finney, M. Hucka, SBMLToolbox: an SBML toolbox for MATLAB users. Bioinformatics 22, 1275 (2006).
103. M. Hucka, A. Finney, H. M. Sauro, H. Bolouri, J. C. Doyle, H. Kitano, A. P. Arkin, B. J. Bornstein, D. Bray, A. Cornish-Bowden, A. A. Cuellar, S. Dronov, E. D. Gilles, M. Ginkel, V. Gor, Goryanin, II, W. J. Hedley, T. C. Hodgman, J. H. Hofineyr, P. J. Hunter, N. S. Juty, J. L. Kasberger, A. Kremling, U. Kummer, N. Le Novere, L. M. Loew, D. Lucio, P. Mendes, E. Minch, E. D. Mjolsness, Y. Nakayama, M. R. Nelson, P. F. Nielsen, T. Sakurada, J. C. Schaff, B. E. Shapiro, T. S. Shimizu, H. D. Spence, J. Stelling, K. Takahashi, M. Tomita, J. Wagner, J. Wang, The systems biology markup language (SBML): a medium for representation and exchange of biochemical network models. Bioinformatics 19, 524 (2003).

104. R. Development Core Team, A language and environment for statistical computing. (R Foundation for Statistical Computing, Vienna, Austria, 2005), vol. Version 2.12.1.

105. H. Akaike, A New Look at the Statistical Model Identification. IEEE Trans. Automat. Contr. AC 19, 716 (1974).

The invention claimed is:

1. A computerized method for treating an mTOR-related tumor disease with kinase inhibitors comprising the steps of:
   a. selecting network profile of a biological system based on a dynamic network model of insulin-mammalian Target Of Rapamycin (mTOR) kinase, wherein said biological system comprises a biological cell, and wherein said dynamic network profile comprises a set of biochemical reactions including mTOR kinase and kinetic rate constants and initial concentrations of reactants thereof;
   b. parameterizing the dynamic network model by (i) experimentally modifying at least one species of said dynamic network of said biological system containing mTOR, thereby modifying the dynamic behavior and generating observed time course data of changes of the species constituting said dynamic network model, and (ii) introducing the same modification of at least one species to the dynamic network model thereby generating simulated time course data for changes of the species constituting said dynamic network model;
   (iii) parameterizing, using a dedicated deterministic software mathematical application tool, the dynamic network model by assigning value to at least one species of said at dynamic network model, wherein said parameterizing comprises (iv) varying the values for kinetic reaction rates and/or initial concentrations of species to produce a plurality of simulated time course data of changes in species of said dynamic network model, (v) comparing said observed time course data of changes in said species with said plurality of simulated time course data, (vi) preferentially selecting the parameter sets producing simulated time course data most similar to the observed time course data and (vii) repeating steps (iv)-(vi) until no further increase in similarity beyond a predetermined threshold is achieved; and wherein a concentration of a species in the parameterized equations can be equal to zero, thereby producing a parameterized dynamic network model;
   c. stratifying patients with an mTOR-related tumor disease into a plurality of patient profiles characterized by different levels of at least one species of said at least one parametrized dynamic network model, thereby producing a plurality of parameterized dynamic network models representing the different patient profile characteristics;
   d. (i) selecting at least one drug intervention altering at least one kinetic reaction rate within at least one of said plurality of dynamic network models,
   (ii) simulating the drug intervention and the resulting changes in concentrations of species over time for said plurality of dynamic network models representing said different patient profiles,
   (iii) determining effective patient profile-drug intervention pairs according to the extent of inhibition of the target kinase of said drug intervention and the extent of activation of other species within the network,
   wherein inhibition of said target kinase is considered desirable and activation of other species within the network is undesirable, and;
   e. wherein said drug intervention is mTOR inhibition, assigning a patient to one of said patient profiles, and administering to said patient at least one drug intervention determined effective for said patient profile in step (d) (iii), wherein said drug intervention is selected from the group consisting of PI3K inhibitors; Akt inhibitors and mTORC1 inhibitors.

2. The computerized method according to claim 1, wherein said biochemical reactions are kinase reactions and said reactants and products are phosphorylated or de-phosphorylated species.

3. The computerized method according claim 1, wherein the dynamic time course model output is validated experimentally.

4. The computerized method of claim 1, wherein said biological cell is a tumor cell.

5. The computerized method of claim 1, wherein said mTOR-related tumor disease is breast cancer.

6. A computerized method for treating a mammalian Target Of Rapamycin (mTOR)-related tumor disease with kinase inhibitors comprising the steps of:
   a. (i) selecting a set of biochemical reactions including mTOR kinase and reactions, thereby defining a model of a dynamic network comprising biochemical kinetic reaction rate equations of which at least one contains mTOR;
   b. parameterizing the dynamic network model by (i) modifying experimentally at least one species of said dynamic network containing mTOR, thereby modifying the dynamic behavior and generating observed time course data of changes of the species constituting said dynamic network model, and (ii) introducing the same modification of at least one species to the dynamic network model thereby generating simulated time course data for changes of the species constituting said dynamic network model, (iii) parameterizing the set of biochemical kinetic reaction rate equations by (iv) varying the values for kinetic reaction rates and/or initial concentrations of species to produce a plurality of simulated time course data of changes in species of said dynamic network model, (v) comparing said observed time course data of changes in said species with said plurality of simulated time course data, (vi) preferentially selecting the parameter sets producing simulated time course data most similar to the observed time course data and (vii) repeating steps (iv)-(vi) until no further increase in similarity beyond a predetermined threshold is achieved; and wherein a concentration of a species in the parameterized equations can be equal to zero, thereby producing a parameterized dynamic network model;
   c. stratifying patients with an mTOR-related tumor disease into a plurality of patient profiles characterized by different levels of at least one species of said at least one parametrized dynamic network model, thereby producing a plurality of parameterized dynamic network models representing the different patient profile characteristics;
d. (i) selecting at least one drug intervention altering at least one kinetic reaction rate within at least one of said plurality of dynamic network models,
(ii) simulating the drug intervention and the resulting changes in concentrations of species over time for said plurality of dynamic network models representing said different patient profiles,
(iii) classifying the patient profile-drug intervention pairs according to the effectiveness of inhibition of the target of said intervention and the extent of activation of other species within the network,
wherein effectiveness of said inhibition of said target is considered a positive effect and activation of other species within the network is considered an adverse effect, and
e. wherein said drug intervention is mTOR inhibition, assigning a patient to one of said patient profiles, and administering to said patient at least one intervention predicted to be effective and to minimize ineffective and/or adverse effects for said patient profile in step (d)(iii), wherein said drug intervention is selected from the group consisting of EGFR inhibitors, PI3K inhibitors; Akt inhibitors, CDK4/6 inhibitors and mTORC1 inhibitors.

* * * * *